United States Patent
Duan et al.

(10) Patent No.: US 11,078,186 B2
(45) Date of Patent: Aug. 3, 2021

(54) ROR γ MODULATORS

(71) Applicant: BRISTOL-MYERS SQUIBB COMPANY, Princeton, NJ (US)

(72) Inventors: Jingwu Duan, Yardley, PA (US); Bin Jiang, Bryn Mawr, PA (US); T. G. Murali Dhar, Newtown, PA (US); Zhonghui Lu, King of Prussia, PA (US); Arun Kumar Gupta, Bangalore (IN); Ananta Karmakar, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/348,195

(22) PCT Filed: Nov. 8, 2017

(86) PCT No.: PCT/US2017/060507
§ 371 (c)(1),
(2) Date: May 8, 2019

(87) PCT Pub. No.: WO2018/089406
PCT Pub. Date: May 17, 2018

(65) Prior Publication Data
US 2020/0024257 A1  Jan. 23, 2020

Related U.S. Application Data

(60) Provisional application No. 62/433,425, filed on Dec. 13, 2016, provisional application No. 62/420,182, filed on Nov. 10, 2016.

(51) Int. Cl.

| | | |
|---|---|---|
| C07D 401/14 | (2006.01) | |
| C07D 207/06 | (2006.01) | |
| C07D 207/12 | (2006.01) | |
| C07D 207/16 | (2006.01) | |
| C07D 401/06 | (2006.01) | |
| C07D 403/04 | (2006.01) | |
| C07D 405/12 | (2006.01) | |
| C07D 413/06 | (2006.01) | |

(52) U.S. Cl.
CPC ......... *C07D 401/14* (2013.01); *C07D 207/06* (2013.01); *C07D 207/12* (2013.01); *C07D 207/16* (2013.01); *C07D 401/06* (2013.01); *C07D 403/04* (2013.01); *C07D 405/12* (2013.01); *C07D 413/06* (2013.01)

(58) Field of Classification Search
None
See application file for complete search history.

(56) References Cited

U.S. PATENT DOCUMENTS

| 2,852,526 A | * | 9/1958 | Villani | ................. | C07D 207/06 548/577 |
| 3,935,217 A | * | 1/1976 | Nakanishi et al. | .. | C07D 207/08 548/526 |

OTHER PUBLICATIONS

Davoren, Jennifer, et al., "Remarkable [3+2] Annulations of Electron-Rich Olefins with Unstabilized Azomethine Ylides", SYNLETT, 2010, No. 16, pp. 2490-2492.
Enyedy, Istvan J., et al., "Pharmacophore-Based Discovery of 3,4-Disubstituted Pyrrolidines as a Novel Class Monoamine Transporter Inhibitors", Biorganic and Medicinal Chemistry Letters 11, 2001, pp. 1113-1118.
Roussi, Georges, et al., "A 3+2 Cycloaddition Route to N—H Pyrrolidines Devoid of Electron-Withdrawing Groups", Tetrahedron Letters, 1988, vol. 29, No. 28, pp. 3481-3482.

* cited by examiner

*Primary Examiner* — Joseph R Kosack
(74) *Attorney, Agent, or Firm* — Elliott Korsen; Shrikant M. Kulkarni

(57) ABSTRACT

There are described RORγ modulators of the formula (I),

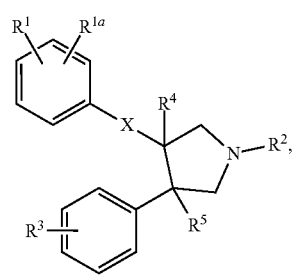

or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

4 Claims, No Drawings

ROR γ MODULATORS

CROSS-REFERENCE TO RELATED APPLICATIONS

This application claims the benefit of U.S. Provisional Application No. 62/420,182 filed Nov. 10, 2016 and U.S. Provisional Application No. 62/433,425 filed Dec. 13, 2016, the disclosures of which are incorporated herein by reference in their entirety.

FIELD OF THE INVENTION

This invention relates to modulators of the retinoid-related orphan receptor RORγ and methods for using such modulators. The compounds described herein can be particularly useful for diagnosing, preventing, or treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors RORα, RORβ, and RORγ play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γ6, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula,

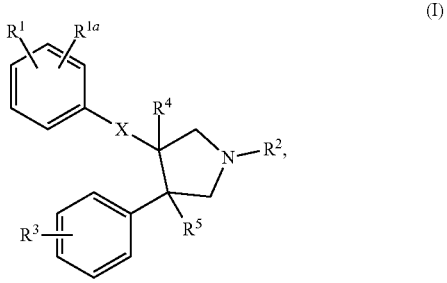

(I)

or pharmaceutically acceptable salts thereof, wherein all substituents are defined herein. The invention includes stereoisomers, tautomers, pharmaceutically acceptable salts, solvates, or prodrugs thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for antagonizing RORγ in a cell comprising contacting the cell with an effective amount of a compound according to formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

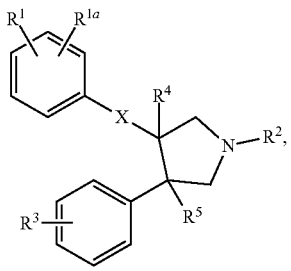

I or a stereoisomer or pharmaceutically-acceptable salt thereof,
wherein
X is a direct bond, C=O, CHOH, $CH_2$ or $SO_2$;
$R^1$ is selected from H, halo, $C_{1-6}$ alkyl substituted with 0-3 $R^{1a}$ and $-(CH_2)_r$-3-14 membered carbocycle substituted with 0-3 $R^{1a}$;
$R^{1a}$ is, independently at each occurrence, hydrogen, =O, halo, $OCF_3$, $OCHF_2$, $CF_3$, $CHF_2$, CN, $NO_2$, $-(CH_2)_rOR^b$, $-(CH_2)_rS(O)_pR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CH_2)_r$-3-14 membered carbocycle substituted with 0-3 $R^a$, or a $-(CH_2)_r$-5-10 membered heterocycle comprising carbon atoms and 1-4 heteroatoms selected from N, O, and $S(O)_p$ substituted with 0-3 $R^a$;
or $R^1$ and $R^{1a}$ may be taken together to form a carbocyclic ring, together with the phenyl ring they are attached to, resulting in either a naphthalene or tetrahydronaphthalene ring;
$R^2$ is selected from hydrogen, $-(CH_2)_rC(O)R^{2d}$, $-(CH_2)_rC(O)OR^{2b}$, $-(CH_2)_rC(O)NR^{11}R^{11}$, $-(CH_2)_rS(O)_2R^{2c}$, $C_{1-6}$ alkyl substituted with 0-3 $R^{2a}$, $C_{2-6}$ alkenyl substituted with 0-3 $R^{2a}$, $-(CH_2)_r$-3-10 membered carbocycle substituted with 0-3 $R^a$, and $-(CH_2)_r$-4-7 membered heterocycle comprising carbon atoms, and 1-4 heteroatoms selected from N, O, and $S(O)_p$ substituted with 0-3 $R^a$;
$R^{2a}$ is, independently at each occurrence, hydrogen, =O, halo, $OCF_3$, CN, $NO_2$, $-(CH_2)_rOR^b$, $-(CH_2)_rS(O)_pR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle substituted with 0-3 $R^a$, or $-(CH_2)_r$-5-7 membered heterocycle comprising carbon atoms, and 1-4 heteroatoms selected from N, O, and $S(O)_p$ substituted with 0-3 $R^a$;
$R^{2b}$ is, independently at each occurrence, hydrogen, $CF_3$, $-(CH_2)_rOR^b$, $-(CH_2)_qS(O)_pR^b$, $-(CH_2)_rC(O)R^{1d}$, $-(CH_2)_rC(O)OR^b$, $-(CH_2)_qC(O)R^b$, $-(CH_2)_qNR^{11}R^{11}$, $-(CH_2)_rC(O)NR^{11}R^{11}$, $-(CH_2)_qNR^bC(O)R^{1c}$, $(CH_2)_qNR^bC(O)OR^c$, $-(CH_2)_qNR^bC(O)NR^{11}R^{11}$, $-(CH_2)_qS(O)_2NR^{11}R^{11}$, $-(CH_2)_qNR^bS(O)_2R^c$, $C_{1-6}$ alkyl substituted with 0-2 $R^a$, $C_{1-6}$ haloalkyl, $-(CH_2)_r$-3-14 membered carbocycle substituted with 0-3 $R^a$, or $-(CH_2)_r$-5-7 membered heterocycle comprising carbon atoms and 1-4 heteroatoms selected from N, O, and $S(O)_p$ substituted with 0-2 $R^a$;
$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, a 5-10 membered heterocycle containing 1-4 heteroatoms selected from N, O, and S, substituted with 0-3 $R^a$, or $-(CH_2)_r$ 5-10 membered heterocycle containing 1-4 heteroatoms selected from N, O, and S, substituted with 0-3 $R^a$;
$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $C_{3-6}$ cycloalkyl substituted with 0-2 $R^d$, or $(CH_2)_r$-phenyl substituted with 0-2 $R^a$, a 5-10 membered heterocycle containing 1-4 heteroatoms selected from N, O, and S, substituted with 0-3 $R^a$;
$R^3$ is hydrogen, halo, $N_3$, CN, $OR^{3b}$, $-NH_2$, $NH(C_{1-6}$ alkyl), $N(C_{1-6}$ alkyl$)_2$, $C_{1-6}$ alkyl substituted with 0-3 $R^{3a}$, $C_{3-10}$ cycloalkyl substituted with 0-3 $R^{3a}$, phenyl substituted with 0-3 $R^{3a}$ or 5-6 membered heteroaryl substituted with 0-3 $R^{3a}$;
$R^{3a}$ is, independently at each occurrence, hydrogen, =O, halo, $CF_3$, $OCF_3$, CN, $NO_2$, $-(CH_2)_rOR^b$, $-(CH_2)_rS(O)_pR^b$, $-(CH_2)_rC(O)R^b$, $-(CH_2)_rC(O)OR^b$, $-(CH_2)_rOC(O)R^b$, $(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle substituted with 0-3 $R^a$, or $-(CH_2)_r$-5-7 membered heterocycle comprising carbon atoms, and 1-4 heteroatoms selected from N, O, and $S(O)_p$ substituted with 0-3 $R^a$;
$R^4$ is hydrogen, halogen, $C_{1-6}$ alkyl, halo $C_{1-6}$ alkyl, hydroxy $C_{1-6}$ alkyl or $C_{1-6}$ alkoxy;
$R^5$ is hydrogen or $C_{1-6}$ alkyl;
$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, $(CH_2)_r$-phenyl substituted with 0-3 $R^d$, or $-(CH_2)_r$-5-7 membered heterocycle comprising carbon atoms and 1-4 heteroatoms selected from N, O, and $S(O)_p$ substituted with 0-3 $R^d$;
or one $R^{11}$ and a second $R^{11}$, both attached to the same nitrogen atom, combine to form a heterocycle comprising carbon atoms and 1-4 heteroatoms selected from N, O, and S(O)$_p$ substituted with 0-3 R$^d$;

R$^a$ is, independently at each occurrence, hydrogen, =O, halo, OCF$_3$, CF$_3$, CHF$_2$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^b$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$ substituted with 0-3 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CH$_2$)$_r$-5-7 membered heterocycle comprising carbon atoms and 1-4 heteroatoms selected from N, O, and S(O)$_p$ substituted with 0-3 R$^f$, or (CH$_2$)$_r$-6-10 carbocycle substituted with 0-3 R$^d$;

R$^c$ is, independently at each occurrence, C$_{1-6}$ alkyl substituted with 0-3 R$^f$, (CH$_2$)$_r$—C$_{3-6}$ cycloalkyl substituted with 0-3 R$^f$, or (CH$_2$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CH$_2$)$_r$C(O)R$^c$, —NR$^e$R$^e$, —NR$^e$C(O)OR$^c$, C(O)NR$^e$R$^e$, —NR$^e$C(O)R$^c$, CO$_2$R$^c$, —NR$^e$SO$_2$R$^e$, SO$_2$R$^c$, C$_{1-6}$ alkyl substituted with 0-3 R$^f$, C$_{3-6}$ cycloalkyl substituted with 0-3 R$^f$, (CH$_2$)$_r$-phenyl substituted with 0-3 R$^f$ or —(CH$_2$)$_r$-5-7 membered heterocycle comprising carbon atoms and 1-4 heteroatoms selected from N, O, and S(O)$_p$ substituted with 0-3 R$^f$;

R$^e$ is, independently at each occurrence, selected from hydrogen, C(O)NR$^f$R$^f$, C$_{1-6}$ alkyl, C$_{3-6}$ cycloalkyl, or (CH$_2$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$ or O(C$_{1-6}$ alkyl);

or R$^f$ is, independently at each occurrence, an optionally substituted —(CH$_2$)$_r$-5-10 membered heterocycle comprising carbon atoms and 1-4 heteroatoms selected from N, O, and S(O)$_p$, phenyl or C$_{3-6}$ cycloalkyl, each group optionally substituted with halo, CN, CF$_3$, C$_{1-6}$ alkyl or O(C$_{1-6}$alkyl);

m and n are independently selected from 0, 1, 2 and 3;

p and q, independently at each occurrence, are 0, 1, or 2; and r is 0, 1, 2, 3, or 4.

In another aspect, there is provided a compound of Formula (I), or stereoisomers, tautomers, pharmaceutically acceptable salts, solvates, or prodrugs thereof, wherein:

R$^1$ is halo, phenyl substituted with 0-3 R$^{1a}$, or C$_{1-6}$ alkyl substituted with 0-3 R$^{1a}$; and R$^{1a}$ is, independently at each occurrence, hydrogen, CF$_3$, halo, C$_{1-6}$ alkyl substituted with 0-3 R$^a$, —(CH$_2$)$_r$OR$^b$, and (CH$_2$)$_r$-phenyl substituted with 0-3 R$^a$.

In another aspect, there is provided a compound of Formula (I), wherein:

R$^2$ is hydrogen, SO$_2$R$^{2c}$, C$_{1-6}$ alkyl substituted with 0-3 R$^{2a}$, CO$_2$R$^{2b}$, —C(O)R$^{2d}$, —C(O)NR$^{11}$R$^{11}$; or a 5-7 membered heterocycle comprising carbon atoms, and 1-4 heteroatoms selected from N, O, and S(O)$_p$ substituted with 0-3 R$^a$, R$^{2a}$ is hydrogen or C$_{1-6}$ alkyl substituted with 0-3 R$^a$;

R$^{2b}$ is hydrogen, C$_{1-6}$ alkyl substituted with 0-3 R$^a$, C$_{3-6}$ cycloalkyl substituted with 0-3 R$^a$, or —(CH$_2$)$_r$-5-7 membered heterocycle comprising carbon atoms and 1-4 heteroatoms selected from N, O, and S(O)$_p$ substituted with 0-3 R$^a$, or (CH$_2$)$_r$-phenyl substituted with 0-3 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or a —(CH$_2$)$_r$ 5-10 membered heterocycle containing 1-4 heteroatoms selected from N, O, and S, substituted with 0-3 R$^a$; and R$^{2d}$ is, independently at each occurrence, hydrogen, C$_{1-6}$ alkyl substituted with 0-3 R$^d$, C$_{1-6}$ haloalkyl, C(O)NR$^{11}$R$^{11}$, C$_{3-6}$ cycloalkyl substituted with 0-2 R$^d$, (CH$_2$)$_r$-phenyl substituted with 0-2 R$^a$, or a 5-10 membered heterocycle containing 1-4 heteroatoms selected from N, O, and S, substituted with 0-3 R$^a$ or a stereoisomer or pharmaceutically-acceptable salt thereof.

In another aspect, there is provided a compound of Formula (I), wherein:

R$^3$ is hydrogen, halo, N$_3$, CN, OR$^{3b}$, —NH$_2$, NH(C$_{1-6}$ alkyl), N(C$_{1-6}$ alkyl)$_2$, C$_{1-6}$ alkyl substituted with 0-3 R$^{3a}$, C$_{3-10}$ cycloalkyl substituted with 0-3 R$^{3a}$, phenyl substituted with 0-3 R$^{3a}$ or 5-6 membered heteroaryl substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CH$_2$)$_r$-3-14 membered carbocycle substituted with 0-3 R$^a$, or a —(CH$_2$)$_r$-5-10 membered heterocycle comprising carbon atoms and 1-4 heteroatoms selected from N, O, and S(O)$_p$ substituted with 0-3 R$^a$; and R$^{3b}$ is, independently at each occurrence, hydrogen, C$_{1-6}$ alkyl substituted with 0-3 R$^a$ or phenyl substituted with 0-3 R$^a$ or a stereoisomer or pharmaceutically-acceptable salt thereof.

In another aspect, there is provided a compound of formula II

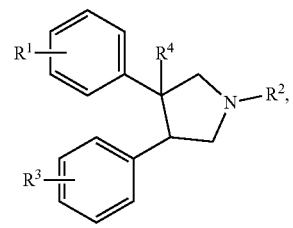

or a stereoisomer or pharmaceutically-acceptable salt thereof, wherein:

R$^1$ is halo, phenyl substituted with 0-3 R$^{1a}$, or C$_{1-6}$ alkyl substituted with 0-3 R$^{1a}$;

R$^{1a}$ is, independently at each occurrence, hydrogen, CF$_3$, halo, C$_{1-6}$ alkyl substituted with 0-3 R$^a$, —(CH$_2$)$_r$OR$^b$, and (CH$_2$)$_r$-phenyl substituted with 0-3 R$^a$;

R$^2$ is hydrogen, SO$_2$R$^{2c}$, C$_{1-6}$ alkyl substituted with 0-3 R$^{2a}$, CO$_2$R$^{2b}$, —C(O)R$^{2d}$, —C(O)NR$^{11}$R$^{11}$; or a 5-7 membered heterocycle comprising carbon atoms, and 1-4 heteroatoms selected from N, O, and S(O)$_p$ substituted with 0-3 R$^a$, $R^{2a}$ is hydrogen or $C_{1-6}$ alkyl substituted with 0-3 $R^a$, $R^{2b}$ is hydrogen, $C_{1-6}$ alkyl substituted with 0-3 $R^a$, $C_{3-6}$ cycloalkyl substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$, or $(CH_2)_r$-phenyl substituted with 0-3 $R^a$;

$R^{2c}$ is independently at each occurrence hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, a 5-10 membered heterocycle containing 1-4 heteroatoms selected from N, O, and S, substituted with 0-3 $R^a$, or a —$(CH_2)_r$ 5-10 membered heterocycle containing 1-4 heteroatoms selected from N, O, and S, substituted with 0-3 $R^a$;

$R^{2d}$ is, independently at each occurrence, hydrogen, $C_{1-6}$ alkyl substituted with 0-3 $R^d$, $C_{1-6}$ haloalkyl, $C(O)NR^{11}R^{11}$, $C_{3-6}$cycloalkyl substituted with 0-2 $R^d$, or $(CH_2)_r$-phenyl substituted with 0-2 $R^a$, a 5-10 membered heterocycle containing 1-4 heteroatoms selected from N, O, and S, substituted with 0-3 $R^a$;

$R^3$ is hydrogen, halo, $N_3$, CN, $OR^{3b}$, —$NH_2$, $NH(C_{1-6}$ alkyl), $N(C_{1-6}$ alkyl$)_2$, $C_{1-6}$ alkyl substituted with 0-3 $R^{3a}$, $C_{3-10}$ cycloalkyl substituted with 0-3 $R^{3a}$, phenyl substituted with 0-3 $R^{3a}$ or 5-6 membered heteroaryl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $C_{1-6}$ alkyl substituted with 0-3 $R^a$ or phenyl substituted with 0-3 $R^a$;

$R^4$ is hydrogen, halogen, $C_{1-6}$ alkyl, halo $C_{1-6}$ alkyl, hydroxy $C_{1-6}$ alkyl or $C_{1-6}$ alkoxy;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, $(CH_2)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$;

or one $R^{11}$ and a second $R^{11}$, both attached to the same nitrogen atom, combine to form a heterocycle comprising carbon atoms and 1-4 heteroatoms selected from N, O, and $S(O)_p$ substituted with 0-3 $R^d$;

$R^d$ is, independently at each occurrence, hydrogen, =O, halo, $OCF_3$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle, or —$(CH_2)_r$-5-7 membered heterocycle comprising carbon atoms and 1-4 heteroatoms selected from N, O, and $S(O)_p$ substituted with 0-3 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CH_2)_r$-5-7 membered heterocycle comprising carbon atoms and 1-4 heteroatoms selected from N, O, and $S(O)_p$ substituted with 0-3 $R^f$, or $(CH_2)_r$-6-10 carbocycle substituted with 0-3 $R^d$;

$R^c$ is, independently at each occurrence, $C_{1-6}$ alkyl substituted with 0-3 $R^f$, $(CH_2)_r$—$C_{3-6}$ cycloalkyl substituted with 0-3 $R^f$, or $(CH_2)_r$-phenyl substituted with 0-3 $R^f$, or $R^d$ is, independently at each occurrence, hydrogen, =O, halo, $OCF_3$, $CF_3$, CN, $NO_2$, —$OR^e$, —$(CH_2)_rC(O)R^c$, —$NR^eR^e$, —$NR^eC(O)OR^c$, $C(O)NR^eR^e$, —$NR^eC(O)R^c$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, $(CH_2)_r$-phenyl substituted with 0-3 $R^f$ or —$(CH_2)_r$-5-7 membered heterocycle comprising carbon atoms and 1-4 heteroatoms selected from N, O, and $S(O)_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, and $(CH_2)_r$-phenyl substituted with 0-3 $R^f$;

$R^f$ is, independently at each occurrence, hydrogen, =O, halo, CN, $NH_2$, $NH(C_{1-6}$alkyl), $N(C_{1-6}$alkyl$)_2$, $SO_2(C_{1-6}$alkyl), $CO_2H$, $CO_2(C_{1-6}$ alkyl), OH, $C_{3-6}$ cycloalkyl, $CF_3$, or $O(C_{1-6}$ alkyl);

or $R^f$ is, independently at each occurrence, an optionally substituted —$(CH_2)_r$-5-10 membered heteroaryl comprising carbon atoms and 1-4 heteroatoms selected from N, O, and S(O), phenyl or $C_{3-6}$ cycloalkyl, each group optionally substituted with halo, CN, $CF_3$, $C_{1-6}$ alkyl or $O(C_{1-6}$ alkyl);

m and n are independently selected from 0, 1, and 2;

p and q, independently at each occurrence, are 0, 1, or 2; and r is 0, 1, or 2.

In another aspect, there is provided a compound of Formula (I), or stereoisomers, tautomers, pharmaceutically acceptable salts, solvates, or prodrugs thereof, wherein $R^3$ is

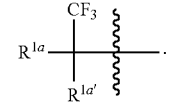

In another aspect, there is provided a compound of Formula (I), or stereoisomers, tautomers, pharmaceutically acceptable salts, solvates, or prodrugs thereof, wherein $R^3$ is $CF_3$ or $CF_3$

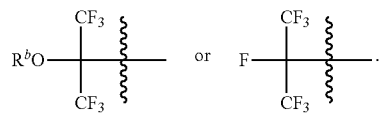

In another aspect, there is provided a compound of Formula (I), or stereoisomers, tautomers, pharmaceutically acceptable salts, solvates, or prodrugs thereof, wherein $R^2$ is $CO_2R^{2b}$, —$C(O)R^{2d}$, or $C(O)NR^{11}R^{11}$ In another aspect, there is provided a compound of formula (II)

wherein $R^1$ is hydrogen, halo, $N_3$, CN, —O(phenyl), —$NH_2$, $NH(C_{1-6}$ alkyl), $N(C_{1-6}$ alkyl$)_2$, $C_{1-6}$ alkyl or $C_{3-6}$ cycloalkyl.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group

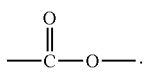

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl(C$_{0-4}$)alkyl includes a substituted lower alkyl having at least one aryl substituent and also includes an aryl directly bonded to another group, i.e., aryl(C$_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—C$_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. C$_{3-7}$ cycloalkyl is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

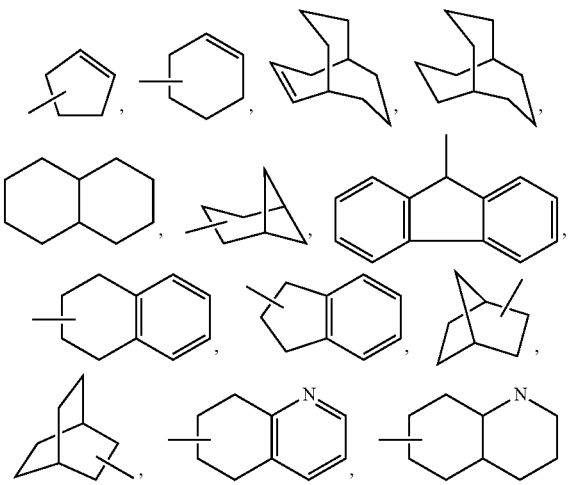

and the like, which optionally may be substituted at any available atoms of the ring(s). Preferred cycloalkyl groups include cyclopropyl, cyclopentyl, cyclohexyl, and

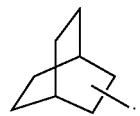

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes OCF$_3$.

Thus, examples of aryl groups include:

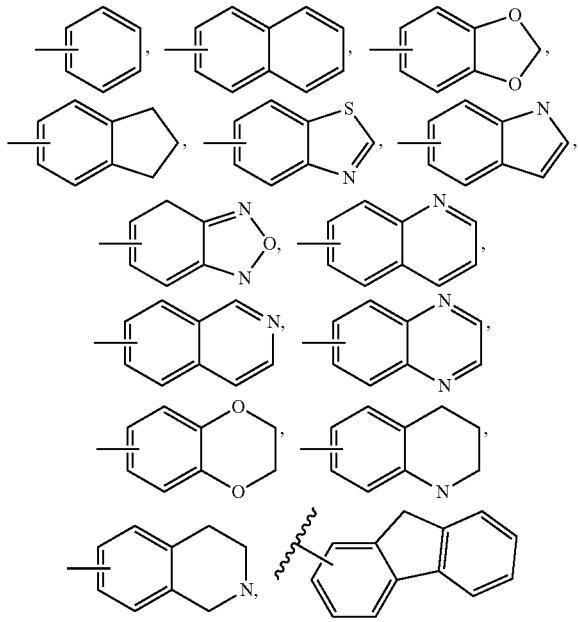

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

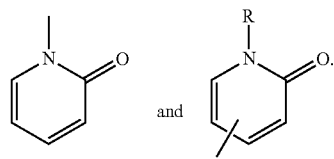

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

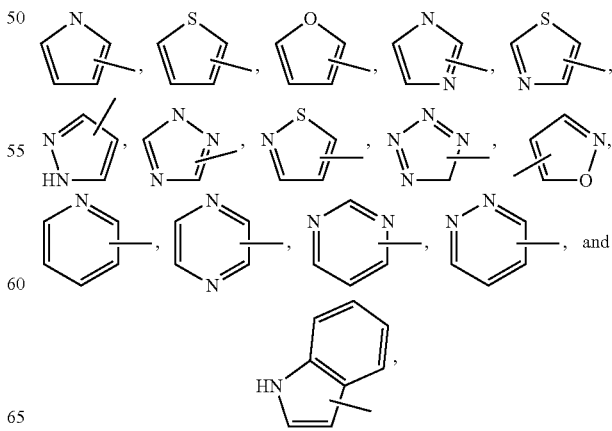

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle, carbocyclyl or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., Methods in Enzymology, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol Metab.*, preprint available online Jul. 11, 2012 at http://www.sciencedirect.com/science/article/pii/S1043276012000926; M. S. Maddur et al., "Th117 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.*, 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2):159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," *Gastroenterology,* 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.*, 2012 August; 42(8): 1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.*, 2012 Jun. 1; 122(6):2252-6; and S. P. Raychaudhuri, "Role of IL-17 in Psoriasis and Psoriatic Arthritis," *Clin. Rev. Allergy Immunol.*, preprint available online Feb. 24, 2012 at http://rd.springer.com/article/10.1007/s12016-012-8307-1 (PubMed PMID: 22362575), each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factorT-bet and RORγt in mice," *Blood,* 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.*, 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. *Nat. Med.*, 2012 July: 18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2)

inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease. As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

METHODS OF PREPARATION

The compounds of the present invention may be synthesized by many methods available to those skilled in the art of organic chemistry. Examples of compounds of the present invention are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

Examples

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

HPLC Conditions

Analytical HPLC Method A:
Column: Waters XBridge C18, 4.6×150 mm, 3.5-μm particles; Mobile Phase A: 5:95 acetonitrile:water with 0.05% TFA; Mobile Phase B: 95:5 acetonitrile:water with 0.05% TFA; Gradient: 0-100% B over 30 minutes; Flow: 1 mL/min.
Analytical HPLC Method B:
Column: Waters Sunfire C18, 3.0×150 mm, 3.5-μm particles; Mobile Phase A: 5:95 acetonitrile:water with 0.05% TFA; Mobile Phase B: 95:5 acetonitrile:water with 0.05% TFA; Gradient: 10-100% B over 10 minutes, then a 5-minute hold at 100% B; Flow: 1 mL/min.
Analytical HPLC Method C:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.
Analytical HPLC Method D:
Column: YMC CombiScreen ODS-A S5, 4.6×50 mm; Mobile Phase A: 10:90 methanol:water with 0.2% H3PO4; Mobile Phase B: 90:10 methanol:water with 0.2% H3PO4; Gradient: 0-100% B over 4 minutes, then a 1-minute hold at 100% B; Flow: 4 mL/min.
Analytical HPLC Method E:
Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Gradient: 0-95% B over 2 minutes, then a 0.75-minute hold at 100% B; Flow: 1 mL/min.
Analytical HPLC Method F:
Column: Luna C18 (4.6×30) mm, 3 μm; Mobile Phase A: 10:90 acetonitrile:water with 10 mM ammonium acetate; Mobile Phase B: 90:10 acetonitrile:water with 10 mM ammonium acetate; Gradient: 0-95% B over 2 minutes; Flow: 4 mL/min.
Analytical HPLC Method G:
Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Intermediate 1 rac-(3S,4S)-tert-butyl 4-(4-bromophenyl)-3-(4-fluorophenyl)-3-methylpyrrolidine-1-carboxylate

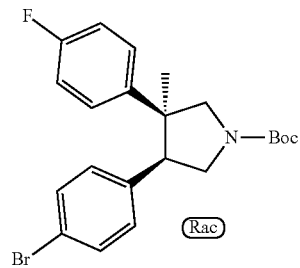 [SMILES: CC(C)(C)OC(=O)N1C[C@@H](c2ccc(Br)cc2)[C@@](C)(c2ccc(F)cc2)C1]

Step A: Ethyl 3-(4-bromophenyl)-2-(4-fluorophenyl)-4-nitrobutanoate

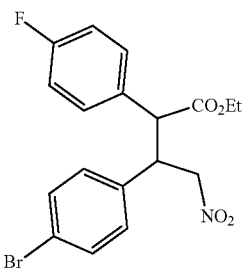 [SMILES: CCOC(=O)C(c1ccc(F)cc1)C(C[N+](=O)[O-])c1ccc(Br)cc1]

To a tetrahydrofuran (30 mL) solution of ethyl 2-(4-fluorophenyl)acetate (1.4 g, 7.67 mmol) under nitrogen atmosphere was added LDA (4.99 mL, 9.98 mmol, 2 M solution) at −78° C. and stirred for 40 min. A tetrahydrofuran (20 mL) solution of (E)-1-bromo-4-(2-nitrovinyl)benzene (1.75 g, 7.67 mmol) was then added slowly at −78° C. The resulting mixture was stirred for 3 h and the temperature was gradually brought to 0° C. The reaction mixture was quenched with saturated ammonium chloride solution (50 mL) and extracted with ethyl acetate (2×50 mL). Combined organic layer was dried over sodium sulfate, filtered and concentrated under reduced pressure. The crude material was purified by silica gel column chromatography, eluting with 10% ethyl acetate in hexanes. Desired fractions were concentrated to yield ethyl 3-(4-bromophenyl)-2-(4-fluorophenyl)-4-nitrobutanoate (2.0 g, 64% yield) as brown oil. MS (ES): m/z=426.5 [M+18].

Step B: ethyl 4-amino-3-(4-bromophenyl)-2-(4-fluorophenyl)butanoate

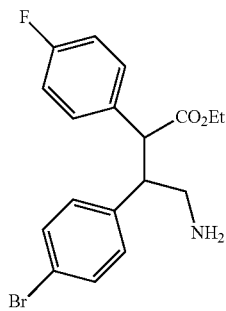 [SMILES: CCOC(=O)C(c1ccc(F)cc1)C(CN)c1ccc(Br)cc1]

To a solution of ethyl 3-(4-bromophenyl)-2-(4-fluorophenyl)-4-nitrobutanoate (2 g, 4.88 mmol) in ethanol (25 mL) and acetic acid (2 mL) was added zinc (1.275 g, 19.50 mmol). The mixture was stirred at room temperature overnight, filtered through celite and washed with EtOH (2×15 mL). Combined filtrate was concentrated under reduced pressure. The residue was taken in ethyl acetate (50 mL) and washed with 10% sodium bicarbonate (2×30 mL). Organic layer was dried over sodium sulfate, filtered and concentrated under reduced pressure to yield ethyl 4-amino-3-(4-bromophenyl)-2-(4-fluorophenyl)butanoate (2.0 g) as brown oil. The crude material was taken to the next step without further purification. MS (ES): m/z=381.5 [M+18].

Step C: rac-(3R,4R)-4-(4-Bromophenyl)-3-(4-fluorophenyl)pyrrolidin-2-one

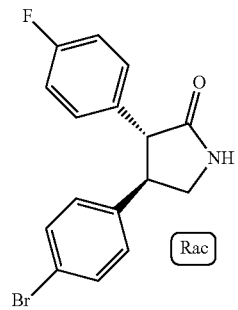 [SMILES: O=C1NC[C@@H](c2ccc(Br)cc2)[C@@H]1c1ccc(F)cc1]

Ethyl 4-amino-3-(4-bromophenyl)-2-(4-fluorophenyl)butanoate (6.8 g, 17.88 mmol) was taken in DMF (25 mL) under nitrogen atmosphere and heated to 80° C. overnight. The reaction mixture was concentrated under reduced pressure to remove most of the DMF. To the residue was added water (200 mL) and the mixture was extracted with ethyl acetate (2×150 mL). The combined organic layer was again washed with water (100 mL) and brine (100 mL), dried over sodium sulfate and concentrated. Crude product mixture was purified by silica gel column chromatography, eluting with 80-85% ethyl acetate in hexanes. Desired fractions were collected and concentrated to yield rac-(3R,4R)-4-(4-bromophenyl)-3-(4-fluorophenyl)pyrrolidin-2-one (2.8 g, 47% yield) as off-white semi-solid. MS (ES): m/z=335.5 [M+1]; $^1$H NMR (400 MHz, DMSO-d6): δ 8.01 (s, 1H), 7.47 (d, J=8.4 Hz, 2H), 7.31 (d, J=8.4 Hz, 2H), 7.20-7.16 (m, 2H), 7.12-7.06 (m, 2H), 3.84 (d, J=11.2 Hz, 1H), 3.72-3.63 (m, 1H), 3.62-3.55 (m, 1H), 3.30-3.25 (m, 1H).

Step D: rac-(3R,4R)-tert-butyl 4-(4-bromophenyl)-3-(4-fluorophenyl)-2-oxopyrrolidine-1-carboxylate and rac-(3R,4S)-di-tert-butyl 4-(4-bromophenyl)-3-(4-fluorophenyl)-2-oxopyrrolidine-1,3-dicarboxylate

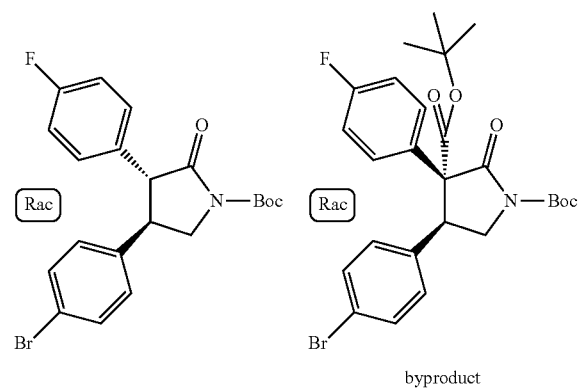 [SMILES: CC(C)(C)OC(=O)N1C[C@@H](c2ccc(Br)cc2)[C@H](c2ccc(F)cc2)C1=O ; CC(C)(C)OC(=O)N1C[C@@H](c2ccc(Br)cc2)[C@@](C(=O)OC(C)(C)C)(c2ccc(F)cc2)C1=O]

byproduct

To a dichloromethane (200 mL) solution of 4-(4-bromophenyl)-3-(4-fluorophenyl)pyrrolidin-2-one (16.22 g, 48.5 mmol) was added triethylamine (20.29 mL, 146 mmol), DMAP (5.93 g, 48.5 mmol) and Boc$_2$O (19.25 g, 88 mmol) at 0° C. The resulting mixture was stirred at ambient temperature for 1 h then concentrated. Silica gel column purification, eluting with 0-40% ethyl acetate in hexanes, gave desired rac-(3R,4R)-tert-butyl 4-(4-bromophenyl)-3-(4-fluorophenyl)-2-oxopyrrolidine-1-carboxylate (8.26 g, 39% yield) as off white gummy solid. MS (ES): m/z=377.9, 379.9 [M−55]; $^1$H NMR (400 MHz, CDCl$_3$): δ 7.48-7.43 (m, 2H), 7.12-7.04 (m, 4H), 7.02-6.96 (m, 2H), 4.21 (dd, J=10.9, 8.0 Hz, 1H), 3.82 (d, J=11.9 Hz, 1H), 3.72 (t, J=10.7 Hz, 1H), 3.57-3.46 (m, 1H), 1.57 (s, 9H). The undesired byproduct rac-(3R,4S)-di-tert-butyl 4-(4-bromophenyl)-3-(4-fluorophenyl)-2-oxopyrrolidine-1,3-dicarboxylate (10.09 g, 39% yield) was obtained as white solid and is used in Intermediate 24 synthesis. MS (ES): m/z=421.9, 423.9 [M−111]; $^1$H NMR (400 MHz, CDCl$_3$): δ 7.30-7.27 (m, 2H), 6.88-6.82 (m, 2H), 6.80-6.75 (m, 2H), 6.70 (d, J=8.6 Hz, 2H), 4.45 (t, J=7.7 Hz, 1H), 4.04 (dd, J=11.0, 7.3 Hz, 1H), 3.69 (dd, J=10.9, 8.0 Hz, 1H), 1.60 (s, 9H), 1.45 (s, 9H).

Step E: rac-(3S,4S)-tert-butyl 4-(4-bromophenyl)-3-(4-fluorophenyl)-3-methyl-2-oxopyrrolidine-1-carboxylate

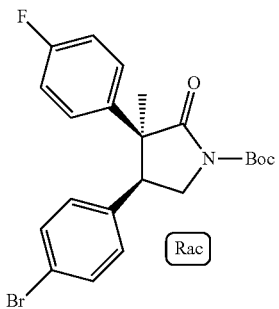 [SMILES: CC(C)(C)OC(=O)N1C[C@@H](c2ccc(Br)cc2)[C@@](C)(c2ccc(F)cc2)C1=O]

To a tetrahydrofuran (100 mL) solution of rac-(3R,4R)-tert-butyl 4-(4-bromophenyl)-3-(4-fluorophenyl)-2-oxopyrrolidine-1-carboxylate (1.5 g, 3.45 mmol) at −78° C. under nitrogen atmosphere was added LHMDS (5.18 mL, 5.18 mmol, 1 M solution) slowly and the resulting solution was stirred for 30 min. Iodomethane (0.648 mL, 10.36 mmol) was added to the above reaction mixture at −78° C. and the mixture was stirred for additional 3 h (during this time temperature was gradually raised to room temperature). The reaction was quenched with saturated ammonium chloride solution (50 mL), extracted with ethyl acetate (2×50 mL). The combined organic layer was dried over sodium sulfate, filtered and concentrated. The crude material was purified by silica gel column purification, eluting with 10% ethyl acetate in hexanes, to yield rac-(3S,4S)-tert-butyl 4-(4-bromophenyl)-3-(4-fluorophenyl)-3-methyl-2-oxopyrrolidine-1-carboxylate (1.0 g, 65% yield) as off-white gummy solid. $^1$H NMR (400 MHz, DMSO-d6): δ 7.34 (d, J=11.2 Hz, 2H), 7.02 (t, J=12 Hz, 2H), 6.80-6.70 (m, 4H), 3.99 (dd, J=14.4, 10 Hz, 1H), 3.73 (t, J=14 Hz, 1H), 3.68-3.64 (m, 1H), 1.53 (s, 12H).

Step F: rac-(3S,4S)-tert-butyl 4-(4-bromophenyl)-3-(4-fluorophenyl)-3-methylpyrrolidine-1-carboxylate

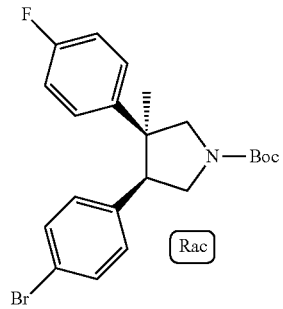

To a tetrahydrofuran (20 mL) solution of rac-(3S,4S)-tert-butyl 4-(4-bromophenyl)-3-(4-fluorophenyl)-3-methyl-2-oxopyrrolidine-1-carboxylate (600 mg, 1.338 mmol) under nitrogen atmosphere was added lithium triethylborohydride (1.606 mL, 1.606 mmol, 1 M solution) at −78° C. The reaction mixture was stirred at −78° C. for 30 min, allowed to reach ambient temperature and quenched with saturated sodium bicarbonate solution (15 mL). The mixture was cooled to 0° C. Hydrogen peroxide (0.5 mL, 30 wt %) was added. The solution was stirred at 0° C. for another 20 min then concentrated under reduced pressure to remove tetrahydrofuran. The aqueous residue was further diluted with water (10 mL) and dichloromethane (20 mL). Organic layer was separated. Remaining aqueous layer was extracted with dichloromethane (2×15 mL). Combined organic layer was dried and concentrated under high vacuum to produce off-white gummy solid (625 mg). The resulting solid was taken in dichloromethane (20 mL), to that was added triethylsilane (0.428 mL, 2.676 mmol). After cooling to −78° C. Boron trifluoride diethyl etherate (0.374 mL, 2.944 mmol) was added. The reaction mixture was stirred at −78° C. for 3 h, allowed to reach ambient temperature, quenched with saturated sodium bicarbonate solution (20 mL) and extracted with dichloromethane (3×20 mL). Combined organic layer was dried over sodium sulfate, filtered and concentrated under reduced pressure to obtain pale brown oil. The crude material was purified by preparative HPLC (Column: Symmetry C-18, 19×250 mm, 7-μm particles; Mobile Phase A: 10 mM ammonium acetate/acetic acid/water pH 4.5 buffer; Mobile Phase B: acetonitrile; Gradient: 40-90% B over 10 minutes; Flow: 17 mL/min) to yield rac-(3S,4S)-tert-butyl 4-(4-bromophenyl)-3-(4-fluorophenyl)-3-methylpyrrolidine-1-carboxylate (240 mg, 41% yield) as off-white solid. MS (ES): m/z=377.9, 379.9 [M−55]; $^1$H NMR (400 MHz, CDCl$_3$): δ 7.27-7.22 (m, 2H), 6.90-6.75 (m, 4H), 6.55-6.50 (m, 2H), 4.08 (dd, J=36, 11.6 Hz, 1H), 3.85-3.72 (m, 1H), 3.56-3.37 (m, 2H), 3.26 (q, J=8.8 Hz, 1H), 1.53 (m, 9H), 1.45 (d, J=4 Hz, 3H).

Intermediate 2 rac-(3R,4R)-tert-butyl 3-(4-bromophenyl)-4-phenylpyrrolidine-1-carboxylate

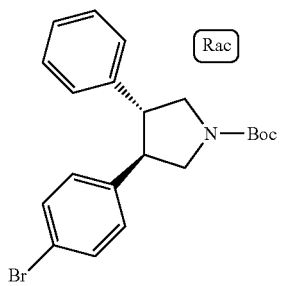

Steps A-D: rac-(3R,4R)-tert-butyl 4-(4-bromophenyl)-2-oxo-3-phenylpyrrolidine-1-carboxylate

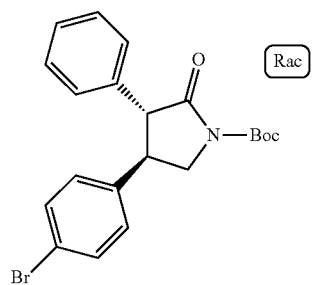 [SMILES: CC(C)(C)OC(=O)N1C[C@@H](c2ccc(Br)cc2)[C@H](c2ccccc2)C1=O]

Similar to the sequence from steps A to D in Intermediate 1 synthesis, ethyl 2-phenylacetate (5.76 g, 35.1 mmol) and (E)-1-bromo-4-(2-nitrovinyl)benzene (8.0 g, 35.1 mmol) were converted to rac-(3R,4R)-tert-butyl 4-(4-bromophenyl)-2-oxo-3-phenylpyrrolidine-1-carboxylate (2.4 g, 16% yield over 4 steps). MS (ES): m/z=360 [M−55]; $^1$H NMR (400 MHz, DMSO-d6): δ 7.47 (d, J=11.2 Hz, 2H), 7.38-7.22 (m, 3H), 7.18-7.02 (m, 4H), 7.23 (dd, J=10.8, 8.1 Hz, 1H), 3.85 (d, J=11.7 Hz, 1H), 3.74 (t, J=10.2 Hz, 1H), 3.78-3.55 (m, 1H), 1.57 (s, 9H).

Step E: rac-(3R,4R)-tert-butyl 3-(4-bromophenyl)-4-phenylpyrrolidine-1-carboxylate

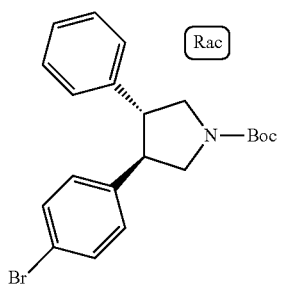 [SMILES: CC(C)(C)OC(=O)N1C[C@@H](c2ccccc2)[C@H](c2ccc(Br)cc2)C1]

Similar to step F of Intermediate 1 synthesis, rac-(3R,4R)-tert-butyl 4-(4-bromophenyl)-2-oxo-3-phenylpyrrolidine-1-carboxylate (1.0 g, 2.402 mmol) was converted to rac-(3R,4R)-tert-butyl 3-(4-bromophenyl)-4-phenylpyrrolidine-1-carboxylate (400 mg, 41% yield). MS (ES): m/z=348 [M−55]; $^1$H NMR (300 MHz, CDCl$_3$): δ 7.38 (d, J=8.1 Hz, 2H), 7.29-7.13 (m, 5H), 7.04 (d, J=8.2 Hz, 2H), 4.10-3.89 (m, 2H), 3.55-3.35 (m, 4H), 1.50 (s, 9H).

Intermediate 3 rac-(3S,4S)-tert-butyl 4-(4-bromophenyl)-3-ethyl-3-phenylpyrrolidine-1-carboxylate

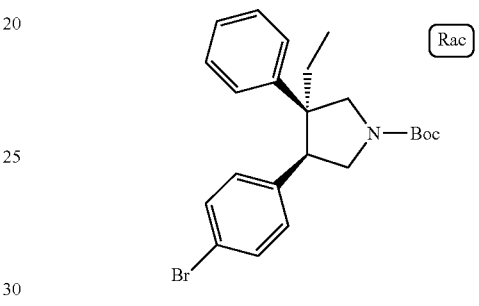

Step A: rac-(3S,4S)-tert-butyl 4-(4-bromophenyl)-3-ethyl-2-oxo-3-phenylpyrrolidine-1-carboxylate

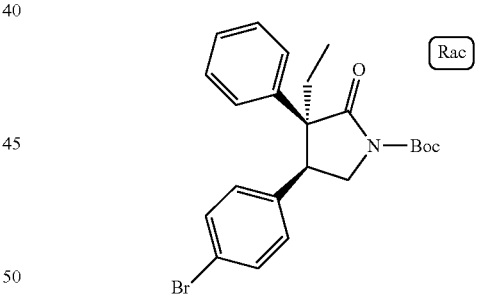

Similar to step E of Intermediate 1 synthesis, rac-(3R,4R)-tert-butyl 4-(4-bromophenyl)-2-oxo-3-phenylpyrrolidine-1-carboxylate (1.2 g, 2.88 mmol, from step D of Intermediate 1) was reacted with iodoethane (0.699 mL, 8.65 mmol) to give rac-(3S,4S)-tert-butyl 4-(4-bromophenyl)-3-ethyl-2-oxo-3-phenylpyrrolidine-1-carboxylate (550 mg, 43% yield). $^1$H NMR (400 MHz, CDCl$_3$): δ 7.26-7.23 (m, 2H), 7.16-7.13 (m, 3H), 6.71-6.67 (m, 2H), 6.55 (dd, J=6.4, 1.6 Hz, 2H), 3.96 (dd, J=10.4, 7.2 Hz, 1H), 3.66 (t, J=10.4 Hz, 1H), 3.56 (dd, J=10.4, 7.2 Hz, 1H), 2.13-1.98 (m, 2H), 1.60 (s, 9H), 1.08 (t, J=7.2 Hz, 3H).

Step B: rac-(3S,4S)-tert-butyl 4-(4-bromophenyl)-3-ethyl-3-phenylpyrrolidine-1-carboxylate

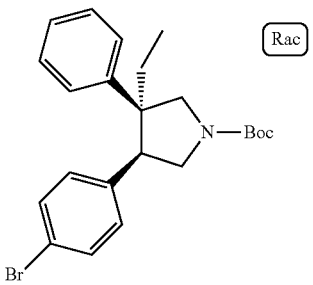 [SMILES: CC[C@]1(c2ccccc2)CN(C(=O)OC(C)(C)C)C[C@H]1c1ccc(Br)cc1]

Similar to the step F of Intermediate 1 synthesis, rac-(3S, 4S)-tert-butyl 4-(4-bromophenyl)-3-ethyl-2-oxo-3-phenylpyrrolidine-1-carboxylate (113 mg, 0.254 mmol) was converted to rac-(3S,4S)-tert-butyl 4-(4-bromophenyl)-3-ethyl-3-phenylpyrrolidine-1-carboxylate (65 mg, 59% yield). MS (ES): m/z=374 [M−55]; $^1$H NMR (400 MHz, CDCl$_3$): δ 7.27-7.14 (m, 5H), 6.77-6.73 (m, 2H), 6.48 (t, J=7.2 Hz, 2H), 4.13 (dd, J=36, 11.6 Hz, 1H), 3.84-3.65 (m, 1H), 3.56-3.20 (m, 3H), 2.22-2.15 (m, 1H), 1.70-1.61 (m, 1H), 1.60-1.48 (m, 9H), 0.74-0.66 (m, 3H).

Intermediate 4 rac-(3S,4R)-1-benzyl-3-(4-bromophenyl)-4-(naphthalen-1-ylmethyl)pyrrolidine

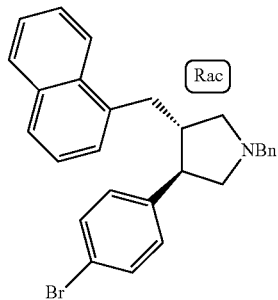 [SMILES: Brc1ccc([C@@H]2CN(Cc3ccccc3)C[C@H]2Cc2cccc3ccccc23)cc1]

Step A: (E)-3-(4-bromophenyl)-1-(naphthalen-1-yl)prop-2-en-1-one

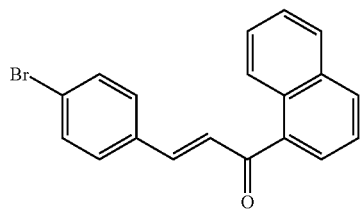 [SMILES: O=C(/C=C/c1ccc(Br)cc1)c1cccc2ccccc12]

To an ethanol (80 mL) solution of 4-bromobenzaldehyde (2.0 g, 10.81 mmol) at 0° C. was added 1-(naphthalen-1-yl)ethanone (1.840 g, 10.81 mmol) and KOH (0.303 mL, 16.21 mmol). The reaction mixture was stirred at room temperature for 12 h then filtered. The solid was washed with methanol (10 mL) and dried under vacuum to yield (E)-3-(4-bromophenyl)-1-(naphthalen-1-yl)prop-2-en-1-one (2 g, 55% yield) as a yellow solid. m/z=339 [M+1]; $^1$H NMR (400 MHz, CDCl$_3$): δ 8.33-8.31 (m, 1H), 8.02-7.99 (d, J=12 Hz, 1H), 7.92-7.90 (m, 1H), 7.78-7.76 (d, J=8.0, 7.2 Hz, 1H), 7.59-7.52 (m, 6H), 7.45-7.43 (m, 2H), 7.31-7.25 (m, 1H).

Step B: rac-((3S,4R)-1-benzyl-4-(4-bromophenyl)pyrrolidin-3-yl)(naphthalen-1-yl)methanone

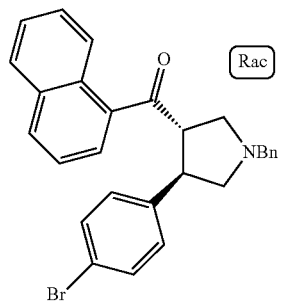 [SMILES: O=C(c1cccc2ccccc12)[C@@H]1CN(Cc2ccccc2)C[C@H]1c1ccc(Br)cc1]

To a dichloromethane (50 mL) solution of (E)-3-(4-bromophenyl)-1-(naphthalen-1-yl)prop-2-en-1-one (1.0 g, 2.97 mmol) at 0° C. was added a dichloromethane solution (10 mL) of N-benzyl-1-methoxy-N-((trimethylsilyl)methyl)methanamine (1.408 g, 5.93 mmol). After stirring for 5 min, trifluoroacetic acid (0.114 mL, 1.483 mmol) was added. After stirring at room temperature for 12 h, the mixture was washed with saturated sodium bicarbonate solution (2×20 mL) and brine (30 mL). The organic layer was dried over anhydrous sodium sulfate, filtered and concentrated under reduced pressure to give dark brown oil. The crude material was purified by silica gel column chromatography, eluting with 10% ethyl acetate in hexanes to yield rac-((3S,4R)-1-benzyl-4-(4-bromophenyl)pyrrolidin-3-yl)(naphthalen-1-yl)methanone (1.3 g, 93% yield). MS (ES): m/z=472 [M+1]; $^1$H NMR (400 MHz, CDCl$_3$): δ 8.45 (d, J=8.0 Hz, 1H), 7.92 (d, J=8.0 Hz, 1H), 7.85 (d, J=8.0 Hz, 1H), 7.59-7.49 (m, 3H), 7.37-7.17 (m, 10H), 4.01-3.89 (m, 1H), 3.88-3.83 (m, 1H), 3.68 (q, J=8.4 Hz, 2H), 3.16 (t, J=8.8 Hz, 1H), 3.02 (t, J=9.2 Hz, 1H), 2.88-2.83 (m, 2H).

Step C: rac-((3R,4S)-1-benzyl-4-(4-bromophenyl)pyrrolidin-3-yl)(naphthalen-1-yl)methanol

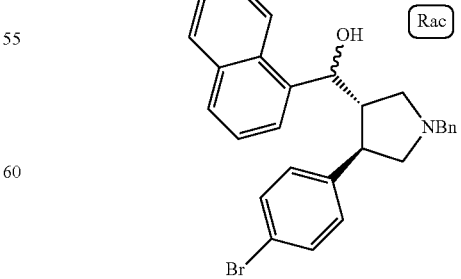

To a methanol (10 mL) solution of rac-((3S,4R)-1-benzyl-4-(4-bromophenyl)pyrrolidin-3-yl)(naphthalen-1-yl)methanone (500 mg, 1.063 mmol) at 0° C. was added NaBH₄ (80 mg, 2.126 mmol) in three equal portion over 15 min and stirred at room temperature for overnight. Reaction mixture was quenched with cold water (5 mL) and concentrated to remove methanol. The resulting brown residue was diluted with water (20 mL) and extracted with ethyl acetate (2×20 mL). Combined organic layer was washed with brine (30 mL), dried over anhydrous sodium sulfate, filtered and concentrated under reduced pressure to give dark brown oil of diastereomeric mixture of rac-((3R,4S)-1-benzyl-4-(4-bromophenyl)pyrrolidin-3-yl)(naphthalen-1-yl)methanol (0.45 g). The crude material was used in the next step without further purification. MS (ES): m/z=472 [M+1].

Step D: rac-(3R,4S)-1-benzyl-3-(4-bromophenyl)-4-(naphthalen-1-ylmethyl)pyrrolidine

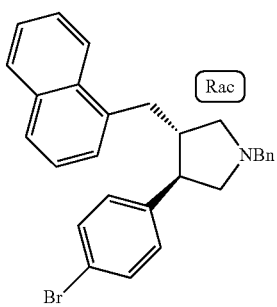 [SMILES: Brc1ccc([C@@H]2CN(Cc3ccccc3)C[C@H]2Cc2cccc3ccccc23)cc1]

The diastereomeric mixture of rac-((3R,4S)-1-benzyl-4-(4-bromophenyl)pyrrolidin-3-yl)(naphthalen-1-yl)methanol (1.4 g, 2.96 mmol) was taken in dichloromethane (40 mL), cooled to 0° C. Trifluoroacetic acid (0.457 mL, 5.93 mmol) and triethylsilane (0.947 mL, 5.93 mmol) were slowly added to the reaction mixture at 0° C. After stirring for 12 h at room temperature, the reaction mixture was concentrated under vacuum. The crude residue was taken in ethyl acetate (100 mL), washed with cold sodium bicarbonate solution (2×50 mL) and brine (50 mL). The organic layer was dried over anhydrous sodium sulfate, filtered and concentrated under reduced pressure to give dark brown oil. The crude was purified by preparative HPLC (Column: Symmetry C-8, 19×300 mm, 7-μm particles; Mobile Phase A: 0.1% TFA in water; Mobile Phase B: acetonitrile; Gradient: 30-60% B over 8 minutes, isocratic at 60% B for 7 minutes then 60-100% B over 11 minutes; Flow: 16 mL/min) to yield rac-(3R,4S)-1-benzyl-3-(4-bromophenyl)-4-(naphthalen-1-ylmethyl)pyrrolidine (1.2 g, 87% yield) as light brown solid. MS (ES): m/z=456 [M+1]; ¹H NMR (400 MHz, CDCl₃): δ 7.84 (d, J=8.0 Hz, 1H), 7.69 (m, 2H), 7.43-7.30 (m, 11H), 7.22-7.06 (m, 2H), 3.65 (dd, J=35.6, 13.2 Hz, 2H), 3.32-3.27 (m, 1H), 3.10-2.92 (m, 3H), 2.83-2.77 (m, 1H), 2.69-2.61 (m, 2H), 2.56-2.52 (m, 1H).

Intermediates 5 and 6

(3S,4R)-3-(2',6'-difluorobiphenyl-4-yl)-4-(naphthalen-1-ylmethyl)pyrrolidine and (3R,4S)-3-(2',6'-difluorobiphenyl-4-yl)-4-(naphthalen-1-ylmethyl)pyrrolidine

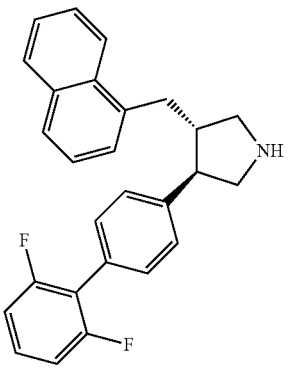

enantiomers 1 and 2

Step A: rac-(3R,4S)-1-benzyl-3-(2',6'-difluorobiphenyl-4-yl)-4-(naphthalen-1-ylmethyl)pyrrolidine

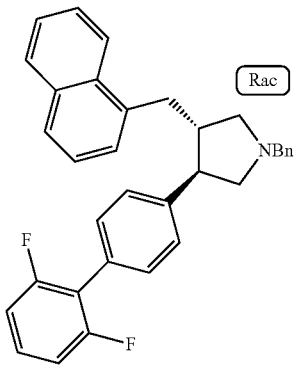 [SMILES: Fc1cccc(F)c1-c1ccc([C@@H]2CN(Cc3ccccc3)C[C@H]2Cc2cccc3ccccc23)cc1]

rac-(3R,4S)-1-benzyl-3-(4-bromophenyl)-4-(naphthalen-1-ylmethyl)pyrrolidine (Intermediate 4, 300 mg, 0.657 mmol) was dissolved in dioxane (3 mL) and to that was added 2,6-difluorophenylboronic acid (208 mg, 1.315 mmol) and potassium phosphate tribasic (349 mg, 1.643 mmol). The mixture was purged with nitrogen for 10 min. Water (0.3 mL) and second Generation XPhos precatalyst (15.51 mg, 0.020 mmol, Aldrich, CAS 131058-14-5) were added and the mixture purged for another 10 min. The reaction vial was sealed and heated in microwave at 90° C. for 2 h. Additional (2,6-difluorophenyl)boronic acid (208 mg, 1.315 mmol), potassium phosphate tribasic (349 mg, 1.643 mmol) and 2nd generation XPhos precatalyst (7.55 mg, 0.010 mmol) were added. The mixture was heated in microwave at 90° C. for additional 2 h. The mixture was diluted with ethyl acetate (50 mL), washed with water (20 mL) and brine (20 mL), dried over sodium sulfate and concentrated under vacuum. Crude compound was purified by silica gel column chromatography, eluting with 10% ethyl acetate in hexanes to yield rac-(3R,4S)-1-benzyl-3-(2', 6'-difluorobiphenyl-4-yl)-4-(naphthalen-1-ylmethyl)pyrrolidine (160 mg, 50% yield) as light brown solid. MS (ES): m/z=490.2 [M+1]. $^1$H NMR (400 MHz, DMSO-d6): δ 7.85 (d, J=1.2 Hz, 1H), 7.72 (d, J=8.4 Hz, 2H), 7.49-7.42 (m, 2H), 7.38-7.29 (m, 11H), 7.23-7.18 (m, 3H), 3.63 (q, J=15.2 Hz, 2H), 3.30-3.01 (m, 4H), 2.80-2.68 (m, 2H), 2.67-2.42 (m, 2H).

Step B: rac-(3R,4S)-3-(2',6'-difluorobiphenyl-4-yl)-4-(naphthalen-1-ylmethyl)pyrrolidine

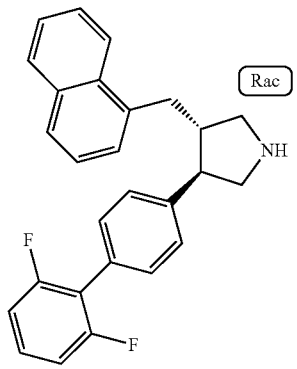 [SMILES: Fc1cccc(F)c1-c1ccc([C@@H]2CNC[C@H]2Cc2cccc3ccccc23)cc1]

To a solution of rac-(3R,4S)-1-benzyl-3-(2',6'-difluorobiphenyl-4-yl)-4-(naphthalen-1-ylmethyl)pyrrolidine (160 mg, 0.327 mmol) in toluene (10 mL) was added 1-chloroethyl chloroformate (0.088 mL, 0.817 mmol). The reaction mixture was stirred at 100° C. for 1 h, cooled to room temperature and concentrated under reduced pressure. The residue was taken in methanol (5 mL), heated at 85° C. for 30 min and concentrated under vacuum. The crude mixture was purified by preparative HPLC (Column: X-select HSS cyano, 19×250 mm, 5-μm particles; Mobile Phase A: 0.1% TFA in water; Mobile Phase B: acetonitrile; Gradient: 30-90% B over 20 minutes, 90-100% B over 1 minute then isocratic at 100% B for 4 minutes; Flow: 17 mL/min) to produce rac-(3R,4S)-3-(2',6'-difluorobiphenyl-4-yl)-4-(naphthalen-1-ylmethyl)pyrrolidine (120 mg, 92% yield) as light yellow solid.

Step C: (3S,4R)-3-(2',6'-difluorobiphenyl-4-yl)-4-(naphthalen-1-ylmethyl)pyrrolidine and (3R,4S)-3-(2',6'-difluorobiphenyl-4-yl)-4-(naphthalen-1-ylmethyl)pyrrolidine

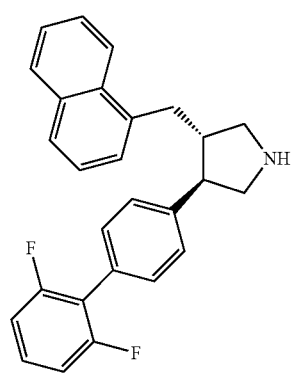

enantiomers 1 and 2

Two enantiomers of rac-(3R,4S)-3-(2',6'-difluorobiphenyl-4-yl)-4-(naphthalen-1-ylmethyl)pyrrolidine (120 mg) were separated by preparative chiral SFC (Chiralcel OJ-H 21×250 mm, 5 m particles, 40% methanol in CO$_2$ with 0.25% DEA, 60 mL/min) to afford the first eluent (50 mg) off the column as Intermediate 5 and the second eluent (40 mg) as Intermediate 6.

Analytical Data for the Enantiomer 1 (Intermediate 5):
Chiral HPLC retention time: 1.72 min, 99.13% pure (Chiralcel OJ-H 4.6×250 mm, 5 m particles, 40% methanol in CO$_2$ with 0.3% diethyl amine, 4 mL/min); MS (ES): m/z=400.0 [M+1]; $^1$H NMR (400 MHz, DMSO-d6): δ 7.87 (d, J=8.0 Hz, 1H), 7.75-7.66 (m, 2H), 7.55-7.27 (m, 10H), 7.22 (t, J=8.0 Hz, 2H), 3.35-3.15 (m, 3H), 3.10-2.92 (m, 3H), 2.86 (dd, J=10.4, 8.0 Hz, 1H), 2.71 (dd, 10.4, 7.2 Hz, 1H)

Analytical Data for the Enantiomer 2 (Intermediate 6):
Chiral HPLC retention time: 2.76 min, 98.38% pure (Chiralcel OJ-H 4.6×250 mm, 5 μm particles, 40% methanol in CO$_2$ with 0.3% diethyl amine, 4 mL/min); MS (ES): m/z=400.0 [M+1]; $^1$H NMR (400 MHz, DMSO-d6): δ 7.87 (d, J=8.0 Hz, 1H), 7.75-7.66 (m, 2H), 7.55-7.27 (m, 10H), 7.22 (t, J=8.0 Hz, 2H), 3.35-3.15 (m, 3H), 3.10-2.92 (m, 3H), 2.86 (dd, J=10.4, 8.0 Hz, 1H), 2.71 (dd, 10.4, 7.2 Hz, 1H).

Intermediate 7 rac-1,1,1,3,3,3-hexafluoro-2-(4-((3R,4S)-4-(naphthalen-1-ylmethyl)pyrrolidin-3-yl)phenyl)propan-2-ol

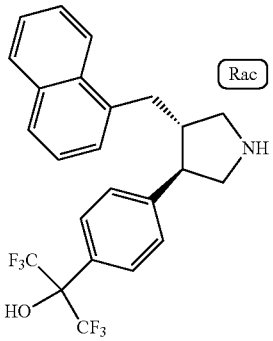 [SMILES: OC(c1ccc([C@@H]2CNC[C@H]2Cc2cccc3ccccc23)cc1)(C(F)(F)F)C(F)(F)F]

Step A: rac-2-(4-((3R,4S)-1-benzyl-4-(naphthalen-1-ylmethyl)pyrrolidin-3-yl)phenyl)-1,1,1,3,3,3-hexafluoropropan-2-ol

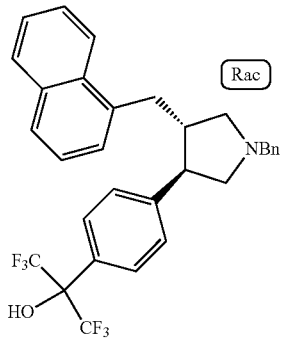 [SMILES: OC(c1ccc([C@@H]2CN(Cc3ccccc3)C[C@H]2Cc2cccc3ccccc23)cc1)(C(F)(F)F)C(F)(F)F]

A 1.7 M pentane solution of tert-tutyllithium (1.651 mL, 2.81 mmol) was added dropwise to a tetrahydrofuran (15 mL) solution of Intermediate 4 (0.5124 g, 1.123 mmol) under nitrogen at −78° C. The resulting yellow solution was stirred for 8 min. Anhydrous hexafluoroacetone gas was condensed (10 drops) in a Dewar condenser with acetone-dry ice and added dropwise to the prepared lithium intermediate at −78° C. After another 40 min at −78° C., the mixture was quenched with saturated ammonium chloride (8 mL) and extracted with ethyl acetate (8 mL). The organic extract was concentrated. The resulting residue was purified by silica gel column chromatography, eluting with 0-40% ethyl acetate in hexanes, gave rac-2-(4-((3R,4S)-1-benzyl-4-(naphthalen-1-ylmethyl)pyrrolidin-3-yl)phenyl)-1,1,1,3,3,3-hexafluoropropan-2-ol (0.4208 g, 69% yield) as colorless oil. MS (ES): m/z=544.2 [M+1]; $^1$H NMR (400 MHz, CDCl$_3$) δ 7.77 (d, J=8.2 Hz, 1H), 7.65 (d, J=8.2 Hz, 1H), 7.60 (d, J=8.7 Hz, 1H), 7.55 (d, J=8.2 Hz, 2H), 7.41 (t, J=6.9 Hz, 1H), 7.36-7.28 (m, 6H), 7.25-7.21 (m, 3H), 3.81-3.70 (m, 2H), 3.30 (dd, J=14.2, 4.8 Hz, 1H), 3.20-3.04 (m, 4H), 2.98-2.91 (m, 1H), 2.81-2.75 (m, 2H).

Step B: rac-1,1,1,3,3,3-hexafluoro-2-(4-((3R,4S)-4-(naphthalen-1-ylmethyl)pyrrolidin-3-yl)phenyl)propan-2-ol

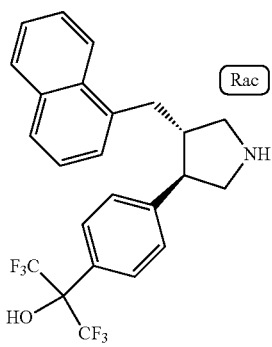 [SMILES: OC(c1ccc([C@@H]2CNC[C@H]2Cc2cccc3ccccc23)cc1)(C(F)(F)F)C(F)(F)F]

Similar to Step B of Intermediates 5 and 6 synthesis, rac-2-(4-((3R,4S)-1-benzyl-4-(naphthalen-1-ylmethyl)pyrrolidin-3-yl)phenyl)-1,1,1,3,3,3-hexafluoropropan-2-ol (276.8 mg, 0.509 mmol) was converted to rac-1,1,1,3,3,3-hexafluoro-2-(4-((3R,4S)-4-(naphthalen-1-ylmethyl)pyrrolidin-3-yl)phenyl)propan-2-ol (75.6 mg, 30% yield). MS (ES): m/z=454.2 [M+1]; $^1$H NMR (400 MHz, 1:1 mixture of CDCl$_3$-CD3OD) δ 7.81-7.61 (m, 4H), 7.50-7.19 (m, 7H), 3.77-3.68 (m, 1H), 3.41 (dd, J=11.6, 7.6 Hz, 1H), 3.36-3.26 (m, 4H), 3.20 (t, J=11.0 Hz, 1H), 3.06-2.95 (m, 1H), 2.94-2.80 (m, 1H).

Intermediate 8 rac-1,1,1,3,3,3-hexafluoro-2-(4-((3R,4S)-4-((5,6,7,8-tetrahdronaphthalen-1-yl)methyl)pyrrolidin-3-yl)phenyl)propan-2-ol

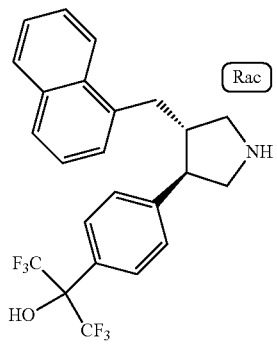 [SMILES: OC(c1ccc([C@@H]2CNC[C@H]2Cc2cccc3ccccc23)cc1)(C(F)(F)F)C(F)(F)F]

A methanol (6 mL) suspension of rac-2-(4-((3R,4S)-1-benzyl-4-(naphthalen-1-ylmethyl)pyrrolidin-3-yl)phenyl)-1,1,1,3,3,3-hexafluoropropan-2-ol (240 mg, 0.442 mmol from Step A of Intermediate 7), Pearlman's catalyst (110 mg, 0.157 mmol) and 4 M HCl in dioxane (120 μL, 0.480 mmol) was hydrogenated at room temperature under 50 psi hydrogen for 17 h. The mixture was filtered and the filtrate was concentrated to give crude rac-1,1,1,3,3,3-hexafluoro-2-(4-((3R,4S)-4-((5,6,7,8-tetrahydronaphthalen-1-yl)methyl)pyrrolidin-3-yl)phenyl)propan-2-ol (185.9 mg, ~80% purity) as brown oil. MS (ES): m/z=458.2 [M+1].

Intermediate 9 rac-(3S,4S)-4-(biphenyl-4-yl)-3-(4-fluorophenyl)-3-methylpyrrolidine

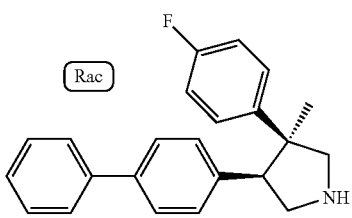 [SMILES: C[C@]1(c2ccc(F)cc2)CNC[C@H]1c1ccc(-c2ccccc2)cc1]

Step A: rac-(3S,4S)-tert-butyl 4-(biphenyl-4-yl)-3-(4-fluorophenyl)-3-methylpyrrolidine-1-carboxylate

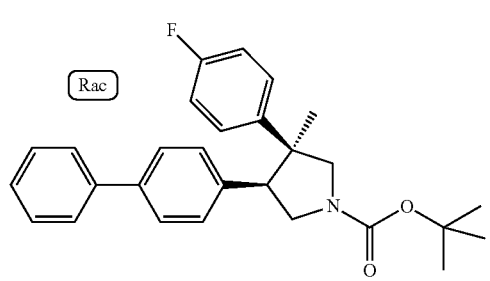 [SMILES: CC(C)(C)OC(=O)N1C[C@@H](c2ccc(-c3ccccc3)cc2)[C@@](C)(c2ccc(F)cc2)C1]

A mixture of Intermediate 1 (10 mg, 0.023 mmol), phenylboronic acid (5.61 mg, 0.046 mmol), Pd$_2$(dba)$_3$-CHCl$_3$ complex (2.108 mg, 2.302 μmol), X-Phos (2.195 mg, 4.60 μmol) and aqueous potassium phosphate tribasic (0.058 mL, 0.115 mmol, 2 M solution) was dissolved in dioxane (0.5 mL). The vial was degassed by vacuum-nitrogen refill cycle twice. The sealed tube was then heated at 90° C. for 90 min. The crude was purified by silica gel column chromatography, eluting with 0-20% ethyl acetate in hexanes, gave rac-(3S,4S)-tert-butyl 4-(biphenyl-4-yl)-3-(4-fluorophenyl)-3-methylpyrrolidine-1-carboxylate (11.7 mg) as yellow oil. $^1$H NMR (400 MHz, CDCl$_3$) δ 7.55 (d, J=7.5 Hz, 2H), 7.46-7.30 (m, 5H), 6.88-6.81 (m, 4H), 6.74 (dd, J=8.0, 5.8 Hz, 2H), 4.21-4.06 (m, 1H), 3.91-3.77 (m, 1H), 3.61-3.47 (m, 2H), 3.41-3.32 (m, 1H), 1.59-1.53 (m, 9H), 1.51 (m, 3H).

Step B: rac-(3S,4S)-4-(biphenyl-4-yl)-3-(4-fluorophenyl)-3-methylpyrrolidine

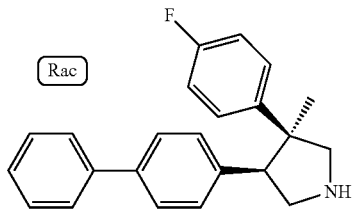 [SMILES: C[C@]1(c2ccc(F)cc2)CNC[C@H]1c1ccc(-c2ccccc2)cc1]

rac-(3S,4S)-tert-Butyl 4-(biphenyl-4-yl)-3-(4-fluorophenyl)-3-methylpyrrolidine-1-carboxylate (11.7 mg) was dissolved in dichloromethane (0.15 mL). To it was added trifluoroacetic acid (0.15 mL). The yellow solution was stirred at room temperature for 20 min. The crude was concentrated. The residue was dissolved in ethyl acetate (2 mL) and washed with saturated sodium bicarbonate (1 mL) and water (1 mL) respectively. The ethyl acetate layer was separated, dried over sodium sulfate and concentrated to give rac-(3S,4S)-4-(biphenyl-4-yl)-3-(4-fluorophenyl)-3-methylpyrrolidine (8 mg, 100% yield). MS (ES): m/z=332.3 [M+1]; $^1$H NMR (400 MHz, CDCl$_3$) δ 7.59-7.51 (m, 2H), 7.44-7.38 (m, 2H), 7.37-7.30 (m, 3H), 7.07-6.95 (m, 2H), 6.84 (t, J=8.7 Hz, 2H), 6.80-6.75 (m, 2H), 3.72 (d, J=10.9 Hz, 1H), 3.55-3.45 (m, 1H), 3.30 (d, J=10.9 Hz, 1H), 3.27-3.19 (m, 2H), 1.52 (s, 3H).

Intermediate 10 rac-4-(4-((3S,4S)-4-(4-fluorophenyl)-4-methylpyrrolidin-3-yl)phenyl)-3,5-dimethylisoxazole

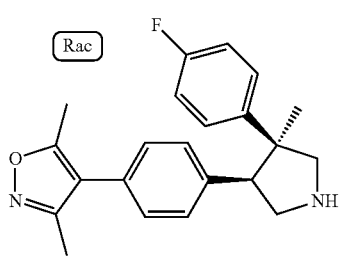 [SMILES: Cc1noc(C)c1-c1ccc([C@@H]2CNC[C@]2(C)c2ccc(F)cc2)cc1]

Similar to the Intermediate 9 synthesis, Intermediate 1 was converted to rac-4-(4-((3S,4S)-4-(4-fluorophenyl)-4-methylpyrrolidin-3-yl)phenyl)-3,5-dimethylisoxazole in two steps. MS (ES): m/z=351.3 [M+1]. $^1$H NMR (400 MHz, CDCl$_3$) δ 7.07 (br. s., 2H), 7.01-6.88 (m, 4H), 6.78 (br. s., 2H), 4.26 (br. s., 1H), 3.89 (br. s., 1H), 3.67-3.50 (m, 2H), 2.38 (br. s., 3H), 2.23 (s, 3H), 1.70 (br. s., 3H).

Intermediate 11 rac-1,1,1,3,3,3-hexafluoro-2-(4-((3S,4S)-4-(4-fluorophenyl)-4-methylpyrrolidin-3-yl)phenyl)propan-2-ol

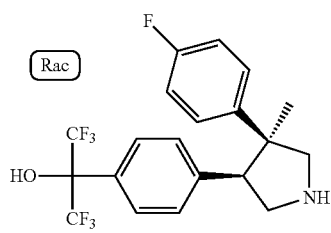 [SMILES: C[C@]1(c2ccc(F)cc2)CNC[C@H]1c1ccc(C(O)(C(F)(F)F)C(F)(F)F)cc1]

Trifluoroacetic acid (250 μL, 3.24 mmol) was added to a dichloromethane (0.5 mL) suspension of Example 5 (0.27 g, 0.518 mmol) and the mixture was stirred at ambient temperature for 16 h. The solvent was evaporated. The residue was triturated with ether (2 mL). The white solid was collected by filtration, washed with ether (2 mL) and dried under vacuum to give rac-1,1,1,3,3,3-hexafluoro-2-(4-((3S,4S)-4-(4-fluorophenyl)-4-methylpyrrolidin-3-yl)phenyl)propan-2-ol trifluoroacetic acid salt (218.5 mg, 79% yield). MS (ES): m/z=422.3 [M+1]; $^1$H NMR (400 MHz, CD3OD) δ 7.52 (d, J=8.4 Hz, 2H), 6.87-6.71 (m, 6H), 4.08 (d, J=12.5 Hz, 1H), 3.70 (dd, J=10.1, 5.5 Hz, 1H), 3.60-3.43 (m, 3H), 1.61 (s, 3H).

Similar to the synthesis of Intermediate 11, intermediates in Table 1 were prepared from their N-Boc protected precursors, the syntheses of which were described in Examples 6-13

TABLE 1

| Intermediate number | Structure | MS observed (M + 1) | HPLC ret. time (min.) | HPLC method |
|---|---|---|---|---|
| 12 | ![structure] | 390.0 | 0.81 | E |
| 13 | ![structure] | 418.2 | 0.81 | E |

TABLE 1-continued

| Intermediate number | Structure | MS observed (M + 1) | HPLC ret. time (min.) | HPLC method |
|---|---|---|---|---|
| 14 | Rac | 404.3 | 0.79 | E |
| 15 | Rac | 404.2 | 0.79 | E |
| 16 | 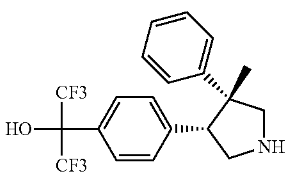 [SMILES: C[C@@]1(c2ccccc2)CNC[C@@H]1c1ccc(C(O)(C(F)(F)F)C(F)(F)F)cc1] | 404.1 | 0.82 | E |
| 17 | 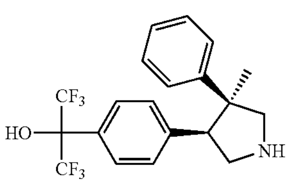 [SMILES: C[C@]1(c2ccccc2)CNC[C@H]1c1ccc(C(O)(C(F)(F)F)C(F)(F)F)cc1] | 404.1 | 0.78 | E |
| 18 | 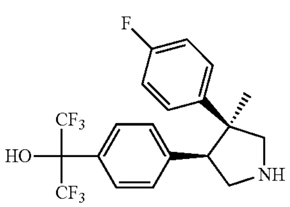 | 422.0 | 0.78 | E |
| 19 | 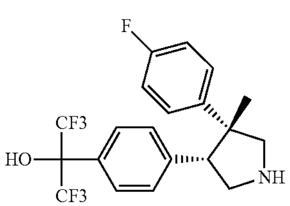 [SMILES: C[C@@]1(c2ccc(F)cc2)CNC[C@@H]1c1ccc(C(O)(C(F)(F)F)C(F)(F)F)cc1] | 422.0 | 0.78 | E |

Intermediate 20 rac-2-(4-((3R,4S)-4-benzylpyrrolidin-3-yl)phenyl)-1,1,1,3,3,3-hexafluoropropan-2-ol

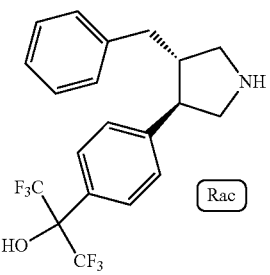 [SMILES: OC(c1ccc([C@@H]2CNC[C@H]2Cc2ccccc2)cc1)(C(F)(F)F)C(F)(F)F]

Step A: rac-2-(4-((3R,4S)-1,4-dibenzylpyrrolidin-3-yl)phenyl)-1,1,1,3,3,3-hexafluoropropan-2-ol

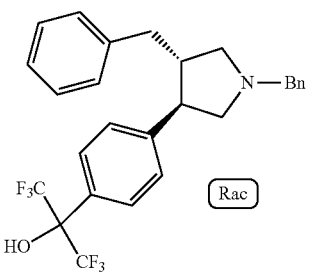 [SMILES: OC(c1ccc([C@@H]2CN(Cc3ccccc3)C[C@H]2Cc2ccccc2)cc1)(C(F)(F)F)C(F)(F)F]

Similar to step A of Intermediate 7 synthesis, Example 21 (620 mg, 1.526 mmol) was converted to rac-2-(4-((3R,4S)-1,4-dibenzylpyrrolidin-3-yl)phenyl)-1,1,1,3,3,3-hexafluoropropan-2-ol. Silica gel column chromatography, eluting with 5-40% ethyl acetate in hexanes, gave both pure (432 mg, 57% yield) and impure product (663 mg) as colorless viscous oil. MS (ES): m/z=494.4 [M+1]. $^1$H NMR (400 MHz, CDCl$_3$) δ 7.59 (d, J=8.2 Hz, 2H), 7.43-7.31 (m, 5H), 7.25-7.10 (m, 5H), 7.05-6.95 (m, 2H), 3.87 (s, 2H), 3.27 (dd, J=10.3, 7.9 Hz, 1H), 3.09 (td, J=10.4, 8.0 Hz, 2H), 2.95-2.73 (m, 3H), 2.69-2.53 (m, 2H).

Step B: rac-2-(4-((3R,4S)-4-benzylpyrrolidin-3-yl)phenyl)-1,1,1,3,3,3-hexafluoropropan-2-ol

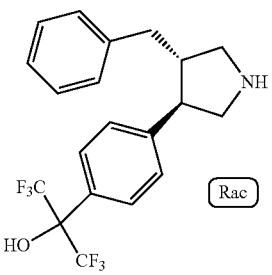 [SMILES: OC(c1ccc([C@@H]2CNC[C@H]2Cc2ccccc2)cc1)(C(F)(F)F)C(F)(F)F]

A methanol (20 mL) solution of impure rac-2-(4-((3R,4S)-1,4-dibenzylpyrrolidin-3-yl)phenyl)-1,1,1,3,3,3- hexafluoropropan-2-ol (753 mg, assuming 1.526 mmol), Pearlman's catalyst (268 mg, 0.382 mmol) and 1 M HCl (3.05 mL, 3.05 mmol) was hydrogenated under 40 psi hydrogen using a Parr Shaker for 3 h. The mixture was filtered to remove the solid catalyst. The filtrate was concentrated and dried under vacuum overnight to give the crude rac-2-(4-((3R,4S)-4-benzylpyrrolidin-3-yl)phenyl)-1,1,1,3,3,3-hexafluoropropan-2-ol HCl salt (632 mg) as purple solid. A fraction (18 mg) of the crude product was further purified by preparative HPLC (Column: Waters XBridge C18, 19×250 mm, 5-m particles; Mobile Phase A: 5:95 acetonitrile:water with 0.1% TFA; Mobile Phase B: 95:5 acetonitrile:water with 0.1% TFA. Flow: 20 mL/min) to give pure analytical sample. MS (ES): m/z=404.2 [M+1]. $^1$H NMR (500 MHz, DMSO-d6) δ 9.04 (br. s., 2H), 8.77 (s, 1H), 7.65 (d, J=7.3 Hz, 2H), 7.48 (d, J=7.3 Hz, 2H), 7.27-7.19 (m, 2H), 7.16 (d, J=6.7 Hz, 1H), 7.09 (d, J=7.3 Hz, 2H), 3.67 (br. s., 1H), 3.34 (br. s., 1H), 3.17 (d, J=9.2 Hz, 2H), 2.99 (br. s., 1H), 2.71-2.60 (m, 3H).

Intermediate 21 rac-(3S,4R)-3-benzyl-4-(2',6'-difluorobiphenyl-4-yl)pyrrolidine

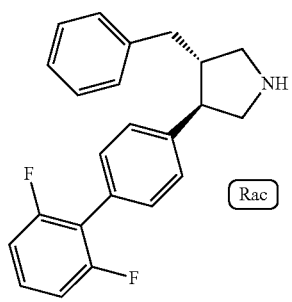 [SMILES: Fc1cccc(F)c1-c1ccc([C@@H]2CNC[C@H]2Cc2ccccc2)cc1]

Step A: rac-(3S,4R)-1,3-dibenzyl-4-(2',6'-difluorobiphenyl-4-yl)pyrrolidine

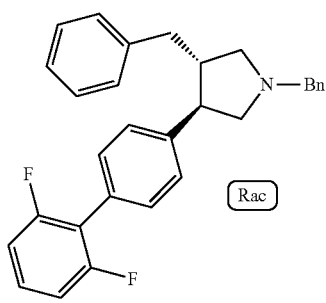 [SMILES: Fc1cccc(F)c1-c1ccc([C@@H]2CN(Cc3ccccc3)C[C@H]2Cc2ccccc2)cc1]

A dioxane (20 mL) solution of Example 21 (500 mg, 1.230 mmol), 2,6-difluorophenylboronic acid (583 mg, 3.69 mmol) and 2 M potassium phosphate tribasic solution (1.846 mL, 3.69 mmol) was pumped under vacuum and backfilled with nitrogen three times. PdCl$_2$(dppf)-CH$_2$Cl$_2$ (201 mg, 0.246 mmol) was quickly added. The mixture was immediately pumped under vacuum and backfilled with nitrogen three times, and stirred at 100° C. under nitrogen for 3 h. Additional 2,6-difluorophenylboronic acid (583 mg), 2 M potassium phosphate tribasic solution (1.846 mL) and PdCl$_2$(dppf)-CH$_2$Cl$_2$ (201 mg) were added with the same degas procedure. The mixture was stirred at 100° C. under nitrogen for additional 3.5 h. The crude mixture was concentrated. The residue was taken up in ethyl acetate (200 mL), washed with water (2×50 mL), brine (50 mL), dried (magnesium sulfate) and concentrated. Silica gel chromatography, eluting with 5-25% ethyl acetate in hexanes, gave rac-(3S,4R)-1,3-dibenzyl-4-(2',6'-difluorobiphenyl-4-yl)pyrrolidine (364.5 mg, 67% yield) as tan viscous liquid. MS (ES): m/z=440.4 [M+1].

$^1$H NMR (400 MHz, CD3OD) δ 7.39-7.28 (m, 9H), 7.27-7.22 (m, 1H), 7.21-7.14 (m, 2H), 7.13-7.01 (m, 5H), 3.77-3.60 (m, 2H), 3.13-3.02 (m, 2H), 2.90-2.73 (m, 3H), 2.71-2.51 (m, 3H).

Step B: rac-(3S,4R)-3-benzyl-4-(2',6'-difluorobiphenyl-4-yl)pyrrolidine

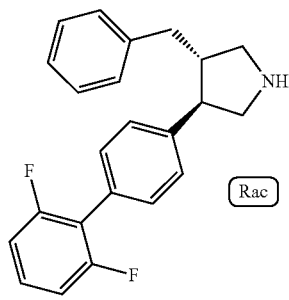 [SMILES: Fc1cccc(F)c1-c1ccc([C@@H]2CNC[C@H]2Cc2ccccc2)cc1]

Similar to Step B of Intermediate 20 synthesis, rac-(3S,4R)-1,3-dibenzyl-4-(2',6'-difluorobiphenyl-4-yl)pyrrolidine (452 mg, 1.028 mmol) was converted to rac-(3S,4R)-3-benzyl-4-(2',6'-difluorobiphenyl-4-yl)pyrrolidine HCl salt (346 mg, 87% yield) as off-white solid. MS (ES): m/z=350.3 [M+1]. $^1$H NMR (400 MHz, CD3OD) δ 7.53-7.35 (m, 5H), 7.30-7.22 (m, 2H), 7.21-7.01 (m, 5H), 3.77 (dd, J=11.4, 7.9 Hz, 1H), 3.47 (dd, J=11.6, 7.4 Hz, 1H), 3.39-3.34 (m, 1H), 3.28-3.20 (m, 1H), 3.14 (t, J=11.0 Hz, 1H), 2.95-2.86 (m, 1H), 2.85-2.76 (m, 1H), 2.71-2.62 (m, 1H).

Intermediate 22

(3S,4S)-3-(4-fluorophenyl)-3-methyl-4-(4-(perfluoropropan-2-yl)phenyl)pyrrolidine

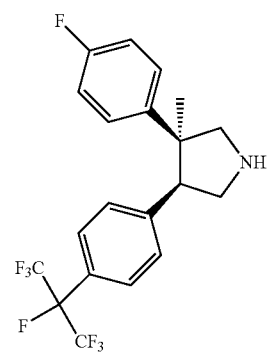 [SMILES: C[C@]1(c2ccc(F)cc2)CNC[C@H]1c1ccc(C(F)(C(F)(F)F)C(F)(F)F)cc1]

Step A: (3S,4S)-tert-butyl 3-(4-fluorophenyl)-3-methyl-4-(4-(perfluoropropan-2-yl)phenyl)pyrrolidine-1-carboxylate

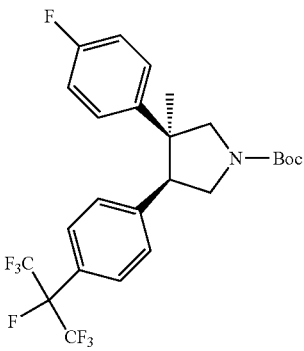 [SMILES: CC(C)(C)OC(=O)N1C[C@@H](c2ccc(C(F)(C(F)(F)F)C(F)(F)F)cc2)[C@@](C)(c2ccc(F)cc2)C1]

DAST (0.253 mL, 1.918 mmol) was added to a stirred dichloromethane (3 mL) solution of Example 6 (100 mg, 0.192 mmol) at room temperature. The mixture was heated to 50° C. in a sealed vial for 4 h. After cooled to room temperature, the crude mixture was slowly quenched with methanol (1 mL). The resulting solution was concentrated. Silica gel chromatography, eluting with 0-50% ethyl acetate in hexanes, gave (3S,4S)-tert-butyl 3-(4-fluorophenyl)-3-methyl-4-(4-(perfluoropropan-2-yl)phenyl)pyrrolidine-1-carboxylate (77 mg, 77% yield) as colorless oil. MS (ES): m/z=468.3 [M−55]. $^1$H NMR (400 MHz, CDCl$_3$) δ 7.37 (d, J=8.2 Hz, 2H), 6.85-6.78 (m, 4H), 6.77-6.71 (m, 2H), 4.18-4.04 (m, 1H), 3.92-3.79 (m, 1H), 3.62-3.47 (m, 2H), 3.41-3.33 (m, 1H), 1.59-1.48 (m, 12H).

Step B: (3S,4S)-3-(4-fluorophenyl)-3-methyl-4-(4-(perfluoropropan-2-yl)phenyl)pyrrolidine

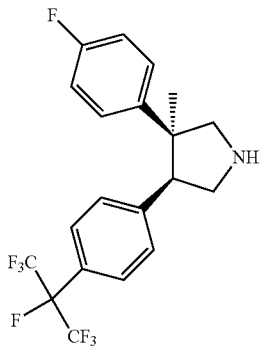

A 4 M dioxane solution of HCl (0.5 mL, 2.000 mmol) was added to a dichloromethane (0.5 mL) solution of (3S,4S)-tert-butyl 3-(4-fluorophenyl)-3-methyl-4-(4-(perfluoropropan-2-yl)phenyl)pyrrolidine-1-carboxylate (77 mg, 0.147 mmol). The mixture was stirred at room temperature for 1 h. The solution was concentrated to give (3S,4S)-3-(4-fluorophenyl)-3-methyl-4-(4-(perfluoropropan-2-yl)phenyl)pyrrolidine HCl salt (64.5 mg, 95% yield) as white solid. MS (ES): m/z=424.3 [M+1]. $^1$H NMR (400 MHz, 1:1 mixture of CDCl$_3$-CD3OD) δ 7.41 (d, J=8.3 Hz, 2H), 6.92 (d, J=8.4 Hz, 2H), 6.88-6.80 (m, 4H), 4.08 (d, J=12.6 Hz, 1H), 3.74 (dd, J=11.1, 6.5 Hz, 1H), 3.65-3.58 (m, 1H), 3.56-3.48 (m, 2H), 1.64 (s, 3H).

Intermediate 23 rac-(3S,4S)-4-(4-(2-(2,6-difluorobenzyloxy)-1,1,1,3,3,3-hexafluoropropan-2-yl)phenyl)-3-methyl-3-phenylpyrrolidine

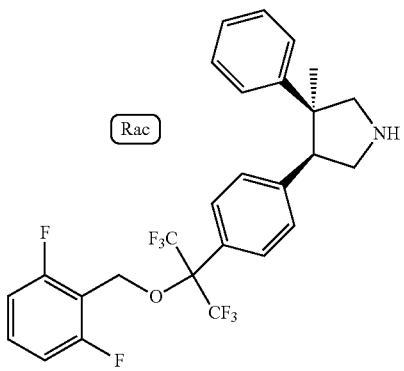 [SMILES: C[C@]1(c2ccccc2)CNC[C@H]1c1ccc(C(OCc2c(F)cccc2F)(C(F)(F)F)C(F)(F)F)cc1]

Step A: rac-(3S,4S)-tert-butyl 4-(4-(2-(2,6-difluorobenzyloxy)-1,1,1,3,3,3-hexafluoropropan-2-yl)phenyl)-3-methyl-3-phenylpyrrolidine-1-carboxylate

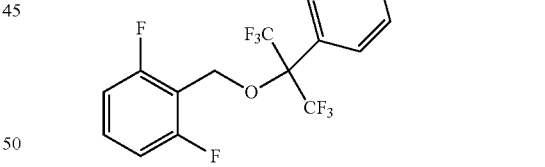

A DMF (8 mL) solution of Example 10 (345 mg, 0.685 mmol), 2-(bromomethyl)-1,3-difluorobenzene (255 mg, 1.233 mmol) and potassium carbonate (474 mg, 3.43 mmol) was stirred at room temperature for 15 h. The mixture was quenched with saturated ammonium chloride (15 mL) and water (15 mL), and extracted with ether (3×10 mL). The combined extracts were dried (magnesium sulfate) and concentrated. Silica gel chromatography, eluting with 5-20% ethyl acetate in hexanes, gave rac-(3S,4S)-tert-butyl 4-(4-(2-(2,6-difluorobenzyloxy)-1,1,1,3,3,3-hexafluoropropan-2-yl)phenyl)-3-methyl-3-phenylpyrrolidine-1-carboxylate (300 mg, 70% yield) as white solid. MS (ES): m/z=574.3 [M−55].

Step B: rac-(3S,4S)-4-(4-(2-(2,6-difluorobenzyloxy)-1,1,1,3,3,3-hexafluoropropan-2-yl)phenyl)-3-methyl-3-phenylpyrrolidine

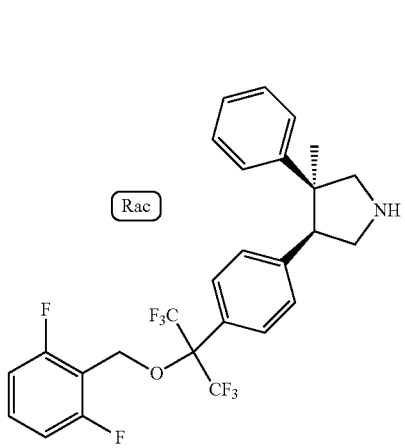 [SMILES: C[C@]1(c2ccccc2)CNC[C@H]1c1ccc(C(OCc2c(F)cccc2F)(C(F)(F)F)C(F)(F)F)cc1]

Similar to Step B of Intermediate 22 synthesis, rac-(3S, 4S)-tert-butyl 4-(4-(2-(2,6-difluorobenzyloxy)-1,1,1,3,3,3-hexafluoropropan-2-yl)phenyl)-3-methyl-3-phenylpyrrolidine-1-carboxylate (287 mg, 0.456 mmol) was converted to rac-(3S,4S)-4-(4-(2-(2,6-difluorobenzyloxy)-1,1,1,3,3,3-hexafluoropropan-2-yl)phenyl)-3-methyl-3-phenylpyrrolidine HCl salt (224 mg, 82% yield) as white solid. MS (ES): m/z=530.3 [M+1]; $^1$H NMR (400 MHz, CD3OD) δ 7.56-7.41 (m, 3H), 7.22-7.13 (m, 3H), 7.11-6.98 (m, 4H), 6.96-6.86 (m, 2H), 4.62 (s, 2H), 4.19 (d, J=12.5 Hz, 1H), 3.89-3.79 (m, 1H), 3.77-3.68 (m, 1H), 3.67-3.62 (m, 1H), 3.59 (d, J=12.5 Hz, 1H), 1.68 (s, 3H).

Intermediate 24 rac-2-(4-((3S,4R)-4-(benzyloxymethyl)-4-(4-fluorophenyl)pyrrolidin-3-yl)phenyl)-1,1,1,3,3,3-hexafluoropropan-2-ol

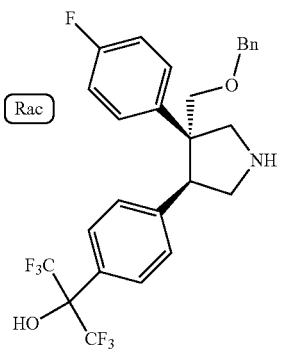 [SMILES: OC(c1ccc([C@@H]2CNC[C@]2(COCc2ccccc2)c2ccc(F)cc2)cc1)(C(F)(F)F)C(F)(F)F]

Step A: Diastereomeric mixture of (3R,4S)-di-tert-butyl 4-(4-bromophenyl)-3-(4-fluorophenyl)-2-hydroxypyrrolidine-1,3-dicarboxylate

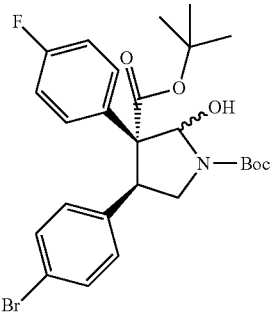 [SMILES: CC(C)(C)OC(=O)N1C[C@@H](c2ccc(Br)cc2)[C@@](C(=O)OC(C)(C)C)(c2ccc(F)cc2)C1O]

A 1 M tetrahydrofuran solution of lithium triethylborohydride (10.50 mL, 10.50 mmol) was added to a tetrahydrofuran (10 mL) solution of rac-(3R,4S)-di-tert-butyl 4-(4-bromophenyl)-3-(4-fluorophenyl)-2-oxopyrrolidine-1,3-dicarboxylate (1.7 g, 3.18 mmol, byproduct from Step D of Intermediate 1 synthesis) at −78° C. under nitrogen. The mixture was stirred −78° C. for 1 h then slowly warmed to room temperature over 1.5 h. The reaction was quenched by slowly adding saturated sodium bicarbonate (10 mL) followed by 30 wt % H$_2$O$_2$ (10 mL). The resulting solution was stirred at room temperature for 1 h and extracted with ethyl acetate (70 mL). The organic layer was washed with brine (5 mL), dried over sodium sulfate and concentrated. Silica gel chromatography, eluting with 0-100% ethyl acetate in hexanes, gave diastereomeric mixture of (3R,4S)-di-tert-butyl 4-(4-bromophenyl)-3-(4-fluorophenyl)-2-hydroxypyrrolidine-1,3-dicarboxylate (1.28 g, 75% yield) as white solid. MS (ES): m/z=518.0, 520.0 [M−17].

Step B: rac-(3R,4S)-4-(4-bromophenyl)-3-(4-fluorophenyl)pyrrolidine-3-carboxylic acid

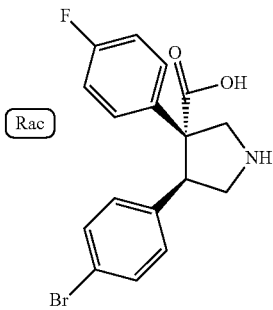 [SMILES: O=C(O)[C@]1(c2ccc(F)cc2)CNC[C@H]1c1ccc(Br)cc1]

Boron trifluoride diethyl etherate (0.433 mL, 3.42 mmol) was added to a dichloromethane (10 mL) suspension of diastereomeric mixture of (3R,4S)-di-tert-butyl 4-(4-bromophenyl)-3-(4-fluorophenyl)-2-hydroxypyrrolidine-1,3-dicarboxylate (833.8 mg, 1.554 mmol) and triethylsilane (0.497 mL, 3.11 mmol) at −78° C. under nitrogen. The mixture was stirred at −78° C. for 5 h, during which time additional boron trifluoride diethyl etherate (0.44 mL) and triethylsilane (0.5 mL) were added. The mixture was warmed to room temperature and stirred for additional 16 h. The reaction mixture was quenched with saturated sodium bicarbonate (20 mL). The suspension was stirred for additional 1 h then filtered. rac-(3R,4S)-4-(4-bromophenyl)-3-(4-fluorophenyl)pyrrolidine-3-carboxylic acid (316 mg, 56% yield) was obtained as white solid. MS (ES): m/z=363.9, 365.9 [M+1]; $^1$H NMR (400 MHz, 1:1 mixture of CDCl$_3$-CD3OD) δ 7.14 (d, J=8.4 Hz, 2H), 7.02 (dd, J=8.4, 5.7 Hz, 2H), 6.81 (d, J=8.1 Hz, 2H), 6.76-6.68 (m, 2H), 4.42-4.36 (m, 1H), 3.94 (d, J=11.0 Hz, 1H), 3.61 (dd, J=11.4, 7.9 Hz, 1H), 3.43 (d, J=11.4 Hz, 1H), 3.08 (dd, J=11.7, 4.4 Hz, 1H).

Step C: rac-(3R,4S)-4-(4-bromophenyl)-1-(tert-butoxycarbonyl)-3-(4-fluorophenyl)pyrrolidine-3-carboxylic acid

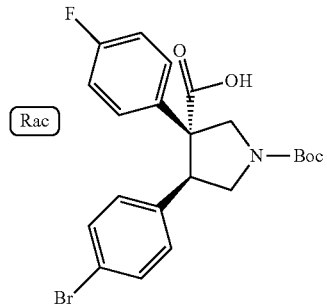 [SMILES: CC(C)(C)OC(=O)N1C[C@@H](c2ccc(Br)cc2)[C@@](C(=O)O)(c2ccc(F)cc2)C1]

Boc$_2$O (138 mg, 0.631 mmol) was added to a tetrahydrofuran (1.4 mL) solution of rac-(3R,4S)-4-(4-bromophenyl)-3-(4-fluorophenyl)pyrrolidine-3-carboxylic acid (209 mg, 0.574 mmol) and 1 M NaOH (1.4 mL, 1.435 mmol). The mixture was stirred at room temperature for 16 h. The reaction was quenched by adding 1 M HCl (1.4 mL). The mixture was diluted with ethyl acetate (4 mL) and shaken vigorously. After phase separation, the ethyl acetate layer was concentrated to give rac-(3R,4S)-4-(4-bromophenyl)-1-(tert-butoxycarbonyl)-3-(4-fluorophenyl)pyrrolidine-3-carboxylic acid (271 mg, 100% yield) as white solid. MS (ES): m/z=407.9, 409.9 [M-55]; $^1$H NMR (400 MHz, CDCl$_3$) δ 7.23 (d, J=8.4 Hz, 2H), 6.91 (d, J=6.8 Hz, 4H), 6.70 (d, J=8.1 Hz, 2H), 4.26-4.15 (m, 3H), 3.91-3.80 (m, 1H), 3.60-3.46 (m, 1H), 1.60-1.49 (m, 9H).

Step D: rac-(3R,4S)-1-tert-butyl 3-methyl 4-(4-bromophenyl)-3-(4-fluorophenyl)pyrrolidine-1,3-dicarboxylate

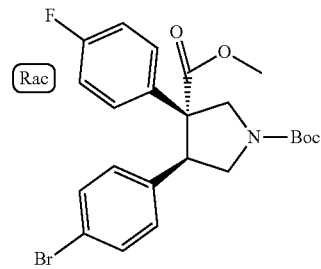 [SMILES: COC(=O)[C@]1(c2ccc(F)cc2)CN(C(=O)OC(C)(C)C)C[C@H]1c1ccc(Br)cc1]

A 2 M ether solution of trimethylsilyldiazomethane (0.350 mL, 0.700 mmol) was added to a methanol (1 mL) solution of rac-(3R,4S)-4-(4-bromophenyl)-1-(tert-butoxycarbonyl)-3-(4-fluorophenyl)pyrrolidine-3-carboxylic acid (271 mg, 0.584 mmol). The mixture was stirred at room temperature for 20 min. Additional trimethylsilyldiazomethane (0.1 mL) was added and the mixture was stirred for additional 10 min. Acetic acid (0.5 mL) was added to quench the reaction. The resulting solution was concentrated. Silica gel chromatography, eluting with 0-30% ethyl acetate in hexanes, gave rac-(3R,4S)-1-tert-butyl 3-methyl 4-(4-bromophenyl)-3-(4-fluorophenyl)pyrrolidine-1,3-dicarboxylate (228 mg, 82% yield) as white solid. MS (ES): m/z=421.9, 423.9 [M-55]; $^1$H NMR (400 MHz, CDCl$_3$) δ 7.23 (d, J=8.6 Hz, 2H), 6.95-6.78 (m, 4H), 6.70 (d, J=7.5 Hz, 2H), 4.26-4.05 (m, 3H), 3.82 (ddd, J=14.9, 11.1, 7.5 Hz, 1H), 3.70 (m, 3H), 3.51 (ddd, J=19.0, 11.2, 7.7 Hz, 1H), 1.54 (m, 9H).

Step E: rac-(3R,4S)-tert-butyl 4-(4-bromophenyl)-3-(4-fluorophenyl)-3-(hydroxymethyl)pyrrolidine-1-carboxylate

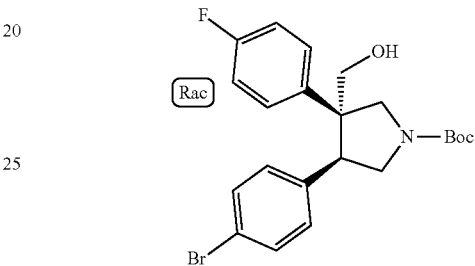

A 2 M tetrahydrofuran solution of lithium borohydride (0.3 mL, 0.600 mmol) was added to a tetrahydrofuran (1.5 mL) solution of rac-(3R,4S)-1-tert-butyl 3-methyl 4-(4-bromophenyl)-3-(4-fluorophenyl)pyrrolidine-1,3-dicarboxylate (228 mg, 0.477 mmol) under nitrogen. The mixture was stirred at room temperature for 1 h. Additional lithium borohydride (2.9 mL) was added and the mixture was stirred for additional 3 days. The crude was added dropwise to a mixture of 1 M NaOH (2 mL) and saturated sodium bicarbonate (10 mL). The mixture was stirred at room temperature for 30 min then extracted with ethyl acetate (20 mL). The ethyl acetate layer was concentrated. Silica gel chromatography, eluting with 0-100% ethyl acetate in hexanes, gave rac-(3R,4S)-tert-butyl 4-(4-bromophenyl)-3-(4-fluorophenyl)-3-(hydroxymethyl)pyrrolidine-1-carboxylate (178 mg, 83% yield) as white solid. MS (ES): m/z=393.9, 395.9 [M-55]; $^1$H NMR (400 MHz, CDCl$_3$) δ 7.27-7.23 (m, 2H), 6.95-6.81 (m, 4H), 6.61 (dd, J=18.4, 8.3 Hz, 2H), 4.10-3.75 (m, 5H), 3.65-3.40 (m, 2H), 1.60-1.46 (m, J=19.6 Hz, 9H).

Step F: rac-(3R,4S)-tert-butyl 3-(benzyloxymethyl)-4-(4-bromophenyl)-3-(4-fluorophenyl)pyrrolidine-1-carboxylate

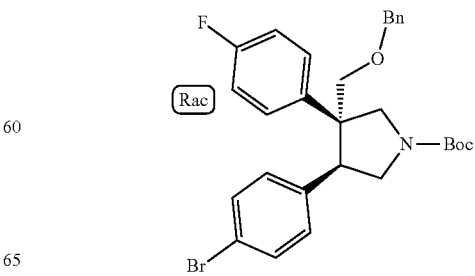

Sodium hydride (20 mg, 0.500 mmol, 60% suspension in mineral oil) was added to a tetrahydrofuran (1.5 mL) solution of rac-(3R,4S)-tert-butyl 4-(4-bromophenyl)-3-(4-fluorophenyl)-3-(hydroxymethyl)pyrrolidine-1-carboxylate (192 mg, 0.426 mmol) and benzyl bromide (0.056 mL, 0.469 mmol). The mixture was stirred at room temperature for 3 h. Additional benzyl bromide (0.02 mL) was added. The mixture was stirred for additional 16 h. The crude was added to saturated ammonium chloride (3 mL) and extracted with ethyl acetate (8 mL). The ethyl acetate layer was concentrated. Silica gel chromatography, eluting with 0-30% ethyl acetate in hexanes, gave rac-(3R,4S)-tert-butyl 3-(benzyloxymethyl)-4-(4-bromophenyl)-3-(4-fluorophenyl)pyrrolidine-1-carboxylate (179 mg, 78%) as white solid. MS (ES): m/z=483.9, 485.9 [M−55]; $^1$H NMR (400 MHz, CDCl$_3$) δ 7.41-7.28 (m, 5H), 7.22 (dd, J=8.0, 6.3 Hz, 2H), 6.90-6.83 (m, 2H), 6.81-6.72 (m, 2H), 6.50 (dd, J=18.4, 8.3 Hz, 2H), 4.60-4.50 (m, 2H), 4.10-3.86 (m, 2H), 3.84-3.57 (m, 4H), 3.51-3.36 (m, 1H), 1.58-1.49 (m, 9H).

Step G: rac-(3R,4S)-tert-butyl 3-(benzyloxymethyl)-3-(4-fluorophenyl)-4-(4-(1,1,1,3,3,3-hexafluoro-2-hydroxypropan-2-yl)phenyl)pyrrolidine-1-carboxylate

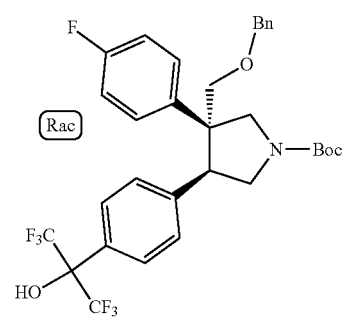 [SMILES: CC(C)(C)OC(=O)N1C[C@@H](c2ccc(C(O)(C(F)(F)F)C(F)(F)F)cc2)[C@@](COCc2ccccc2)(c2ccc(F)cc2)C1]

Similar to Step A of Intermediate 7 synthesis, rac-(3R,4S)-tert-butyl 3-(benzyloxymethyl)-4-(4-bromophenyl)-3-(4-fluorophenyl)pyrrolidine-1-carboxylate (179 mg, 0.331 mmol) was converted to rac-(3R,4S)-tert-butyl 3-(benzyloxymethyl)-3-(4-fluorophenyl)-4-(4-(1,1,1,3,3,3-hexafluoro-2-hydroxypropan-2-yl)phenyl)pyrrolidine-1-carboxylate (14 mg, 7% yield) as white solid. MS (ES): m/z=571.9 [M−55]; $^1$H NMR (400 MHz, CDCl$_3$) δ 7.49-7.42 (m, 2H), 7.41-7.28 (m, 5H), 6.80 (td, J=8.5, 3.6 Hz, 2H), 6.76-6.61 (m, 4H), 4.59-4.53 (m, 2H), 4.09-3.86 (m, 2H), 3.84-3.68 (m, 3H), 3.66-3.59 (m, 1H), 3.54-3.45 (m, 1H), 1.58-1.48 (m, 9H).

Step H: rac-2-(4-((3S,4R)-4-(benzyloxymethyl)-4-(4-fluorophenyl)pyrrolidin-3-yl)phenyl)-1,1,1,3,3,3-hexafluoropropan-2-ol

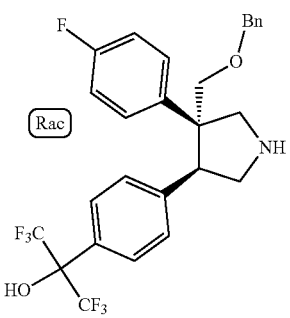 [SMILES: OC(c1ccc([C@@H]2CNC[C@]2(COCc2ccccc2)c2ccc(F)cc2)cc1)(C(F)(F)F)C(F)(F)F]

Similar to Intermediate 11 synthesis, rac-(3R,4S)-tert-butyl 3-(benzyloxymethyl)-3-(4-fluorophenyl)-4-(4-(1,1,1,3,3,3-hexafluoro-2-hydroxypropan-2-yl)phenyl)pyrrolidine-1-carboxylate was converted to rac-2-(4-((3S,4R)-4-(benzyloxymethyl)-4-(4-fluorophenyl)pyrrolidin-3-yl)phenyl)-1,1,1,3,3,3-hexafluoropropan-2-ol trifluoroacetic acid salt. MS (ES): m/z=528.0 [M+1].

Intermediate 25

((3S,4S)-3-(4-fluorophenyl)-4-(4-(1,1,1,3,3,3-hexafluoro-2-hydroxypropan-2-yl)phenyl)-3-methylpyrrolidin-1-yl)(piperidin-4-yl)methanone

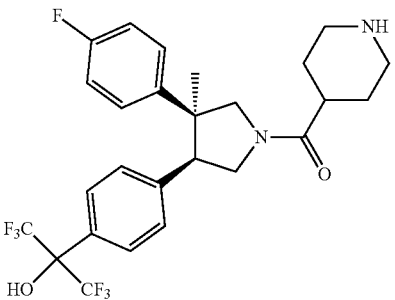 [SMILES: C[C@]1(c2ccc(F)cc2)CN(C(=O)C2CCNCC2)C[C@H]1c1ccc(C(O)(C(F)(F)F)C(F)(F)F)cc1]

Step A: tert-butyl 4-((3S,4S)-3-(4-fluorophenyl)-4-(4-(1,1,1,3,3,3-hexafluoro-2-hydroxypropan-2-yl)phenyl)-3-methylpyrrolidine-1-carbonyl)piperidine-1-carboxylate

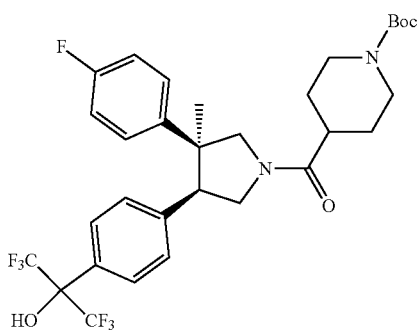 [SMILES: CC(C)(C)OC(=O)N1CCC(C(=O)N2C[C@@H](c3ccc(C(O)(C(F)(F)F)C(F)(F)F)cc3)[C@@](C)(c3ccc(F)cc3)C2)CC1]

Hunig's base (0.043 mL, 0.244 mmol) was added to an acetonitrile (0.5 mL) solution of Intermediate 18 (43.5 mg, 0.081 mmol), o-benzotriazol-1-yl-N,N,N',N'-tetramethyluronium tetrafluoroborate (30.4 mg, 0.095 mmol) and 1-(tert-butoxycarbonyl)piperidine-4-carboxylic acid (20.2 mg, 0.088 mmol). The mixture was stirred at room temperature for 30 min then concentrated. The residue was dissolved in ether (4 mL) and washed with saturated ammonium chloride (2 mL). The ether layer was concentrated. Silica gel chromatography, eluting with 0-100% ethyl acetate in hexanes, gave tert-butyl 4-((3S,4S)-3-(4-fluorophenyl)-4-(4-(1,1,1,3,3,3-hexafluoro-2-hydroxypropan-2-yl)phenyl)-3-methylpyrrolidine-1-carbonyl)piperidine-1-carboxylate (43 mg, 84% yield) as white solid. MS (ES): m/z=633.4 [M+1].

Step B: ((3S,4S)-3-(4-fluorophenyl)-4-(4-(1,1,1,3,3,3-hexafluoro-2-hydroxypropan-2-yl)phenyl)-3-methylpyrrolidin-1-yl)(piperidin-4-yl)methanone

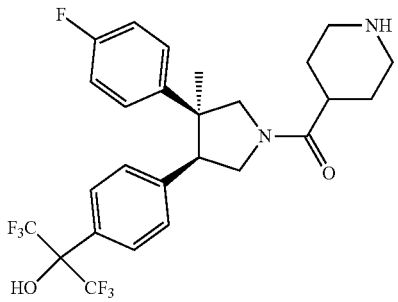 [SMILES: C[C@]1(c2ccc(F)cc2)CN(C(=O)C2CCNCC2)C[C@H]1c1ccc(C(O)(C(F)(F)F)C(F)(F)F)cc1]

Similar to Intermediate 11 synthesis, tert-butyl 4-((3S,4S)-3-(4-fluorophenyl)-4-(4-(1,1,1,3,3,3-hexafluoro-2-hydroxypropan-2-yl)phenyl)-3-methylpyrrolidine-1-carbonyl)piperidine-1-carboxylate (43 mg, 0.068 mmol) was converted to ((3S,4S)-3-(4-fluorophenyl)-4-(4-(1,1,1,3,3,3-hexafluoro-2-hydroxypropan-2-yl)phenyl)-3-methylpyrrolidin-1-yl)(piperidin-4-yl)methanone trifluoroacetic acid salt (57 mg, 100% yield) as white solid. MS (ES): m/z=533.0 [M+1].

Intermediate 26

Diastereomeric mixture of ((3S,4S)-3-(4-fluorophenyl)-4-(4-(1,1,1,3,3,3-hexafluoro-2-hydroxypropan-2-yl)phenyl)-3-methylpyrrolidin-1-yl)(pyrrolidin-3-yl)methanone

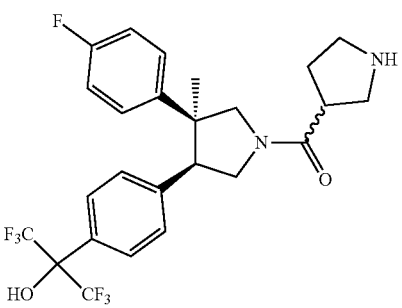 [SMILES: C[C@]1(c2ccc(F)cc2)CN(C(=O)C2CCNC2)C[C@H]1c1ccc(C(O)(C(F)(F)F)C(F)(F)F)cc1]

Step A: Diastereomeric mixture of tert-butyl 3-((3S,4S)-3-(4-fluorophenyl)-4-(4-(1,1,1,3,3,3-hexafluoro-2-hydroxypropan-2-yl)phenyl)-3-methylpyrrolidine-1-carbonyl)pyrrolidine-1-carboxylate

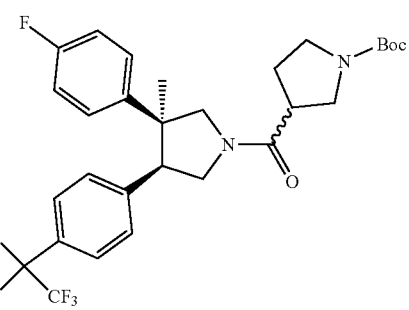

Similar to Step A of Intermediate 25 synthesis, Intermediate 18 (7.5 mg, 0.014 mmol) was coupled with 1-(tert-butoxycarbonyl)pyrrolidine-3-carboxylic acid (4.5 mg, 0.021 mmol) to give diastereomeric mixture of tert-butyl 3-((3S,4S)-3-(4-fluorophenyl)-4-(4-(1,1,1,3,3,3-hexafluoro-2-hydroxypropan-2-yl)phenyl)-3-methylpyrrolidine-1-carbonyl)pyrrolidine-1-carboxylate (11.3 mg, 100% yield) as white solid. MS (ES): m/z=563.0 [M−55]; $^1$H NMR (400 MHz, CDCl$_3$) δ 7.51 (dd, J=12.3, 8.1 Hz, 2H), 6.85-6.63 (m, 6H), 4.02-3.88 (m, 1H), 3.76-3.30 (m, 8H), 3.26-3.05 (m, 1H), 2.42-2.09 (m, 2H), 1.55-1.51 (m, 3H), 1.50-1.45 (m, 9H).

Step B: Diastereomeric mixture of ((3S,4S)-3-(4-fluorophenyl)-4-(4-(1,1,1,3,3,3-hexafluoro-2-hydroxypropan-2-yl)phenyl)-3-methylpyrrolidin-1-yl)(pyrrolidin-3-yl)methanone

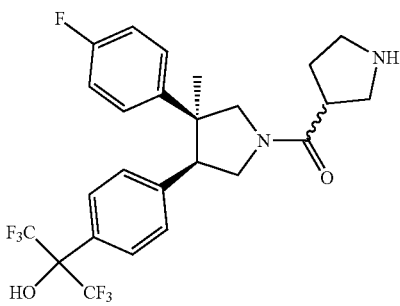

Similar to Intermediate 11 synthesis, diastereomeric mixture of tert-butyl 3-((3S,4S)-3-(4-fluorophenyl)-4-(4-(1,1,1,3,3,3-hexafluoro-2-hydroxypropan-2-yl)phenyl)-3-methylpyrrolidine-1-carbonyl)pyrrolidine-1-carboxylate was converted to diastereomeric mixture of ((3S,4S)-3-(4-fluorophenyl)-4-(4-(1,1,1,3,3,3-hexafluoro-2-hydroxypropan-2-yl)phenyl)-3-methylpyrrolidin-1-yl)(pyrrolidin-3-yl)methanone trifluoroacetic acid salt as white solid. MS (ES): m/z=519.0 [M+1].

Intermediate 27

3-phenylpyrrolidine-1-carbonyl chloride

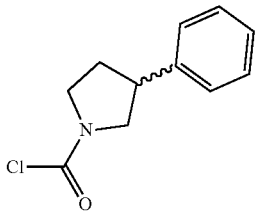 [SMILES: O=C(Cl)N1CCC(c2ccccc2)C1]

Pyridine (0.029 mL, 0.363 mmol) was added to a stirred dichloromethane (2 mL) solution of triphosgene (37.7 mg, 0.127 mmol) at −78° C. A white solid precipitated out from the solution. After 2 h, a dichloromethane (1 mL) solution of 3-phenylpyrrolidine (53.5 mg, 0.363 mmol) was added to the triphosgene-pyridine mixture at −78° C. The resulting orange solution was warmed to ambient temperature for 1 h. Dichloromethane (2 mL), brine (1 mL) and 1 M HCl (1 mL) were added and the mixture was stirred vigorously for 5 min. The dichloromethane layer was isolated, dried over sodium sulfate and filtered. The filtrate was concentrated to give crude 3-phenylpyrrolidine-1-carbonyl chloride (55.7 mg, 73% yield) as brown oil. $^1$H NMR (400 MHz, CDCl$_3$) δ 7.41-7.32 (m, 2H), 7.32-7.21 (m, 3H), 4.11-3.98 (m, 1H), 3.91-3.79 (m, 1H), 3.74-3.41 (m, 3H), 2.44-2.31 (m, 1H), 2.20-2.05 (m, 1H).

The Intermediates in Table 2 were prepared in the same manner as outlined in the synthesis of Intermediate 27 and the crude materials were used in the next step without further purification.

TABLE 2

| Intermediate number | Structure |
| --- | --- |
| 28 | 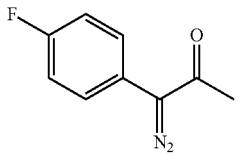 |
| 29 | 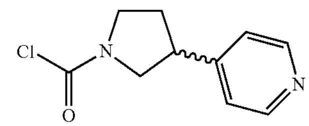 [SMILES: O=C(Cl)N1CCC(c2ccncc2)C1] |
| 30 | 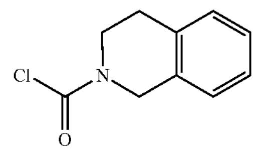 [SMILES: O=C(Cl)N1CCc2ccccc2C1] |

Intermediate 31

1-diazo-1-(4-fluorophenyl)propan-2-one

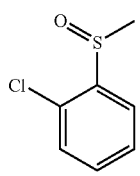

DBU (2.377 mL, 15.77 mmol) was added dropwise to an acetonitrile (50 mL) solution of 1-(4-fluorophenyl)propan-2-one (1.756 mL, 13.14 mmol) and 4-acetamidobenzenesulfonyl azide (3.79 g, 15.77 mmol) at 0° C. The mixture was stirred at 0° C. for 1 h then at ambient temperature for 30 min. The reaction mixture was quenched with saturated sodium bicarbonate (25 mL). The resulting mixture was separated into two layers. The aqueous layer was extracted with ether (30 mL). The organic layers were combined, dried over sodium sulfate and concentrated. Silica gel chromatography, eluting with 0-40% diethyl ether in hexanes, gave 1-diazo-1-(4-fluorophenyl)propan-2-one (2 g, 85% yield) as orange solid. MS (ES): m/z=192.0 [M+14]; $^1$H NMR (400 MHz, CDCl$_3$) δ 7.48 (dd, J=8.8, 5.1 Hz, 2H), 7.17-7.09 (m, 2H), 2.37 (s, 3H).

Intermediate 32

1-chloro-2-(methylsulfinyl)benzene mCPBA (7.36 g, 32.8 mmol, 76% pure) was added to a stirred dichloromethane (60 mL) solution of (2-chlorophenyl)(methyl)sulfane (5.21 g, 32.8 mmol) at 0° C. After 1 h, the crude mixture was quenched with saturated sodium bicarbonate (100 mL). After phase separation, the dichloromethane layer was concentrated. Silica gel chromatography, eluting with 0-50% ethyl acetate in hexanes, gave 1-chloro-2-(methylsulfinyl)benzene (5.7338 g, 100% yield) as colorless oil. MS (ES): m/z=174.9 [M+1]; $^1$H NMR (400 MHz, CDCl$_3$) δ 7.96 (dd, J=7.7, 1.5 Hz, 1H), 7.54 (td, J=7.5, 1.3 Hz, 1H), 7.45 (td, J=7.5, 1.7 Hz, 1H), 7.42-7.37 (m, 1H), 2.83 (s, 3H).

Intermediate 33 rac-(3S,4S)-4-(2',6'-difluorobiphenyl-4-yl)-3-(4-fluorophenyl)-3-methylpyrrolidine

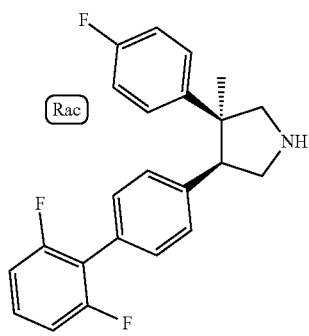 [SMILES: C[C@]1(c2ccc(F)cc2)CNC[C@H]1c1ccc(-c2c(F)cccc2F)cc1]

Step A: rac-(3S,4S)-tert-butyl 4-(2',6'-difluorobiphenyl-4-yl)-3-(4-fluorophenyl)-3-methylpyrrolidine-1-carboxylate

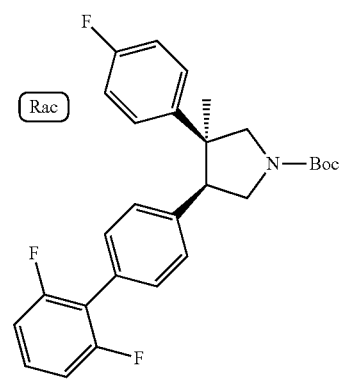 [SMILES: CC(C)(C)OC(=O)N1C[C@@H](c2ccc(-c3c(F)cccc3F)cc2)[C@@](C)(c2ccc(F)cc2)C1]

A mixture of rac-(3S,4S)-tert-butyl 4-(4-bromophenyl)-3-(4-fluorophenyl)-3-methylpyrrolidine-1-carboxylate (200 mg, 0.460 mmol from Intermediate 1), (2,6-difluorophenyl)boronic acid (436 mg, 2.76 mmol), Pd$_2$(dba)$_3$-CHCl$_3$ (42.2 mg, 0.046 mmol), X-Phos (43.9 mg, 0.092 mmol, CAS 564483-18-7), solid K$_3$PO$_4$ (110 mg, 0.518 mmol) and 2 M K$_3$PO$_4$ solution (0.37 mL, 0.740 mmol) was dissolved in dioxane (3 mL). The reaction vial was degassed by vacuum-nitrogen refill cycle twice. The sealed tube was then heated at 90° C. for 2 h. Additional (2,6-difluorophenyl)boronic acid (480 mg), X-Phos (30 mg), Pd$_2$(dba)$_3$.CHCl$_3$ (24 mg) and solid K$_3$PO$_4$ (90 mg) were added. The vial was degassed by vacuum-nitrogen refill cycle twice again. The sealed tube was then heated at 90° C. for additional 3 h. The crude material was loaded onto a silica gel cartridge. Silica gel chromatography, eluded with 0-20% ethyl acetate-hexanes, gave rac-(3S,4S)-tert-butyl 4-(2',6'-difluorobiphenyl-4-yl)-3-(4-fluorophenyl)-3-methylpyrrolidine-1-carboxylate (200.4 mg, 93% yield). MS (ES): m/z=412.3 [M−55]; $^1$H NMR (400 MHz, CDCl$_3$) δ 7.24 (d, J=7.3 Hz, 3H), 6.97 (t, J=7.7 Hz, 2H), 6.90-6.78 (m, 4H), 6.75 (dd, J=8.1, 4.0 Hz, 2H), 4.22-4.05 (m, 1H), 3.92-3.77 (m, 1H), 3.63-3.48 (m, 2H), 3.42-3.32 (m, 1H), 1.60-1.49 (m, 12H).

Step B: rac-(3S,4S)-4-(2',6'-difluorobiphenyl-4-yl)-3-(4-fluorophenyl)-3-methylpyrrolidine

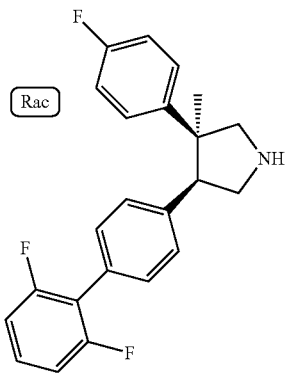 [SMILES: C[C@]1(c2ccc(F)cc2)CNC[C@H]1c1ccc(-c2c(F)cccc2F)cc1]

Similar to synthesis of Intermediate 11, rac-(3S,4S)-tert-butyl 4-(2',6'-difluorobiphenyl-4-yl)-3-(4-fluorophenyl)-3-methylpyrrolidine-1-carboxylate (200.4 mg, 0.429 mmol) was converted to rac-(3S,4S)-4-(2',6'-difluorobiphenyl-4-yl)-3-(4-fluorophenyl)-3-methylpyrrolidine trifluoroacetic acid salt (192.6 mg, 93% yield). MS (ES): m/z=368.3 [M−55]; $^1$H NMR (400 MHz, CDCl$_3$) δ 7.27-7.23 (m, 3H), 7.01-6.85 (m, 6H), 6.77 (d, J=8.3 Hz, 2H), 3.99 (d, J=12.0 Hz, 1H), 3.69-3.60 (m, 1H), 3.50-3.41 (m, 3H), 1.61 (s, 3H).

Intermediates 34 and 35

(3S,4S)-4-(2',6'-difluorobiphenyl-4-yl)-3-(4-fluorophenyl)-3-methylpyrrolidine and (3R,4R)-4-(2',6'-difluorobiphenyl-4-yl)-3-(4-fluorophenyl)-3-methylpyrrolidine

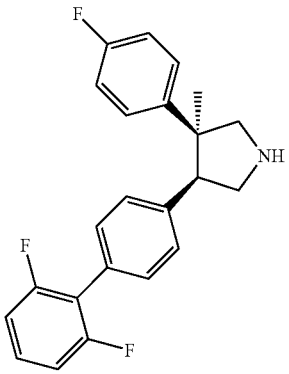

-continued

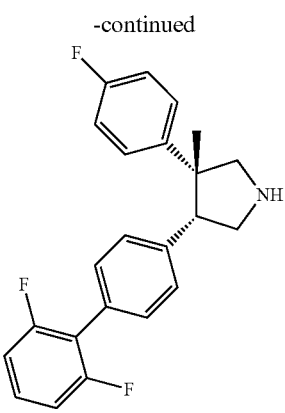

rac-(3S,4S)-4-(2',6'-Difluorobiphenyl-4-yl)-3-(4-fluorophenyl)-3-methylpyrrolidine (170 mg) was separated into its homochiral components by preparative chiral SFC (Chiralpak AD-H 30×250 mm, 5 m particles, 35% methanol in CO₂ with 0.1% diethyl amine, 180 mL/min) to afford the first eluent (83.1 mg) off the column as Intermediate 34 and the second eluent (66.1 mg) as Intermediate 35. Analytical data for enantiomer 1 (Intermediate 34): Chiral HPLC retention time: 1.785 min, >99.9% pure (Chiralpak AD-H 4.6×250 mm, 5 m particles, 35% methanol in CO₂ with 0.1% diethyl amine, 3 mL/min); MS (ES): m/z=368.3 [M+1]; $^1$H NMR (400 MHz, CDCl₃) δ 7.26-7.18 (m, 3H), 7.02-6.92 (m, 4H), 6.89-6.82 (m, 2H), 6.78 (d, J=8.2 Hz, 2H), 3.75 (d, J=10.9 Hz, 1H), 3.54-3.47 (m, 1H), 3.35-3.22 (m, 3H), 1.53 (s, 3H). Analytical data for the enantiomer 2 (Intermediate 35): Chiral HPLC retention time: 4.281 min, 99.6% pure (Chiralpak AD-H 4.6×250 mm, 5 m particles, 35% methanol in CO₂ with 0.1% diethyl amine, 3 mL/min); MS (ES): m/z=368.3 [M+1]; $^1$H NMR (400 MHz, CDCl₃) δ 7.26-7.19 (m, 3H), 7.02-6.93 (m, 4H), 6.88-6.82 (m, 2H), 6.81-6.76 (m, 2H), 3.76 (d, J=10.8 Hz, 1H), 3.57-3.48 (m, 1H), 3.34-3.25 (m, 3H), 1.54 (s, 3H).

Example 1 rac-(3S,4S)-tert-butyl 4-(4-bromophenyl)-3-methyl-3-phenylpyrrolidine-1-carboxylate

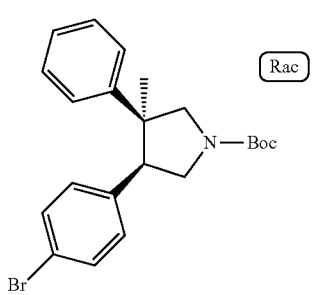 [SMILES: CC(C)(C)OC(=O)N1C[C@@H](c2ccc(Br)cc2)[C@@](C)(c2ccccc2)C1]

Step A: rac-(3S,4S)-tert-butyl 4-(4-bromophenyl)-3-methyl-2-oxo-3-phenylpyrrolidine-1-carboxylate

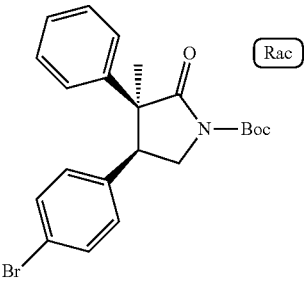 [SMILES: CC(C)(C)OC(=O)N1C[C@@H](c2ccc(Br)cc2)[C@@](C)(c2ccccc2)C1=O]

Similar to Sep E of Intermediate 1 synthesis, rac-(3R,4R)-tert-butyl 4-(4-bromophenyl)-2-oxo-3-phenylpyrrolidine-1-carboxylate (3.0 g, 7.21 mmol, from Step D of Intermediate 2 synthesis) was reacted with iodomethane (1.352 mL, 21.62 mmol) to give rac-(3S,4S)-tert-butyl 4-(4-bromophenyl)-3-methyl-2-oxo-3-phenylpyrrolidine-1-carboxylate (1.7 g, 55% yield). MS (ES): m/z=447 [M+18]; $^1$H NMR (400 MHz, CDCl₃): δ 7.26-7.23 (m, 2H), 7.17-7.14 (m, 3H), 6.71 (dd, J=7.6, 2.2 Hz, 2H), 6.55 (d, J=7.2 Hz, 2H), 3.98 (dd, J=10.4, 7.6 Hz, 1H), 3.70 (t, J=10.4 Hz, 1H), 3.38 (dd, J=10.4, 7.6 Hz, 1H), 1.62 (s, 3H), 1.60 (s, 9H).

Step B: rac-(3S,4S)-tert-butyl 4-(4-bromophenyl)-3-methyl-3-phenylpyrrolidine-1-carboxylate

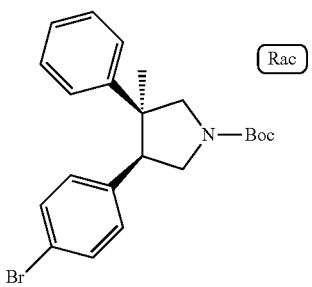 [SMILES: CC(C)(C)OC(=O)N1C[C@@H](c2ccc(Br)cc2)[C@@](C)(c2ccccc2)C1]

Similar to the step F of Intermediate 1 synthesis, rac-(3S,4S)-tert-butyl 4-(4-bromophenyl)-3-methyl-2-oxo-3-phenylpyrrolidine-1-carboxylate (2.5 g, 5.81 mmol) was converted to rac-(3S,4S)-tert-butyl 4-(4-bromophenyl)-3-methyl-3-phenylpyrrolidine-1-carboxylate (1.46 g, 60% yield). MS (ES): m/z=360 [M−55]; LC retention time: 22.08 min (analytical HPLC Method A); $^1$H NMR (400 MHz, CDCl₃): δ 7.28-7.14 (m, 5H), 6.86-6.82 (m, 2H), 6.51 (t, J=8.0 Hz, 2H), 4.12 (dd, J=33.2, 11.2 Hz, 1H), 3.86-3.72 (m, 1H), 3.57-3.41 (m, 2H), 3.36-3.22 (m, 1H), 1.54 (m, 9H), 1.48 (d, J=8.0 Hz, 3H).

Examples 2 and 3

(3R,4R)-tert-butyl 4-(4-bromophenyl)-3-methyl-3-phenylpyrrolidine-1-carboxylate and (3S,4S)-tert-butyl 4-(4-bromophenyl)-3-methyl-3-phenylpyrrolidine-1-carboxylate

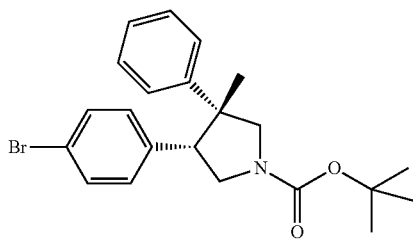

enantiomer 1

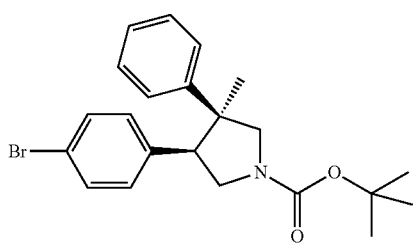

enantiomer 2

Example 1 (1.58 g) was separated into its homochiral components by preparative chiral SFC (OJ-H 30×250 mm, 5 m particles, 10% methanol in CO$_2$, 150 mL/min) to afford the first eluent off the column as Example 2 (0.6966 g) and the second eluent as Example 3 (0.7245 g). Analytical data for the enantiomer 1 (Example 2): Chiral HPLC retention time: 2.98 min, >99.5% pure (OJ-H 4.6×250 mm, 5 μm particles, 10% methanol in CO$_2$, 3 mL/min); MS (ES): m/z=401.1, 403.1 [M−14]; $^1$H NMR (400 MHz, CDCl$_3$) δ 7.22 (dd, J=8.4, 2.6 Hz, 2H), 7.20-7.16 (m, 3H), 6.85 (d, J=4.0 Hz, 2H), 6.52 (t, J=8.1 Hz, 2H), 4.21-4.06 (m, 1H), 3.88-3.74 (m, 1H), 3.60-3.49 (m, 1H), 3.49-3.41 (m, 1H), 3.34-3.24 (m, 1H), 1.57 (s, 4H), 1.53 (s, 5H), 1.49 (d, J=4.8 Hz, 3H). Analytical data for the enantiomer 2 (Example 3): Chiral HPLC retention time: 4.27 min, 98.9% pure (OJ-H 4.6×250 mm, 5 μm particles, 10% methanol in CO$_2$, 3 mL/min); MS (ES): m/z=401.1, 403.1 [M−14]; $^1$H NMR (400 MHz, CDCl$_3$) δ 7.22 (dd, J=8.5, 2.8 Hz, 2H), 7.20-7.15 (m, 3H), 6.86 (dd, J=6.5, 2.3 Hz, 2H), 6.52 (t, J=8.1 Hz, 2H), 4.21-4.07 (m, 1H), 3.87-3.73 (m, 1H), 3.59-3.50 (m, 1H), 3.49-3.41 (m, 1H), 3.34-3.25 (m, 1H), 1.57 (s, 4H), 1.53 (s, 4H), 1.49 (d, J=5.1 Hz, 3H).

Example 4 rac-(3R,4R)-tert-butyl 3-(4-bromophenyl)-3-methyl-4-phenylpyrrolidine-1-carboxylate

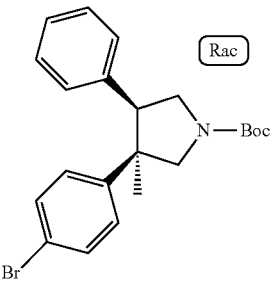 [SMILES: CC(C)(C)OC(=O)N1C[C@H](c2ccccc2)[C@](C)(c2ccc(Br)cc2)C1]

Steps A-D: rac-(3R,4R)-tert-butyl 3-(4-bromophenyl)-2-oxo-4-phenylpyrrolidine-1-carboxylate

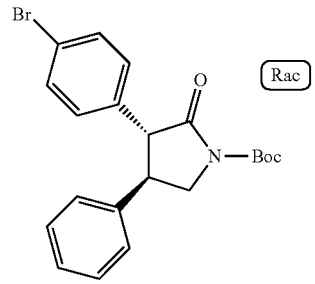 [SMILES: CC(C)(C)OC(=O)N1C[C@@H](c2ccccc2)[C@H](c2ccc(Br)cc2)C1=O]

Similar to the sequence from Step A to D in Intermediate 1 synthesis, methyl 2-(4-bromophenyl)acetate and (E)-(2-nitrovinyl)benzene were converted to rac-(3R,4R)-tert-butyl 3-(4-bromophenyl)-2-oxo-4-phenylpyrrolidine-1-carboxylate. MS (ES): m/z=362 [M−55]; $^1$H NMR (300 MHz, CDCl$_3$) δ ppm 7.47-7.40 (m, 2H), 7.37-7.25 (m, 3H), 7.24-7.14 (m, 2H), 7.07-6.98 (m, 2H) 4.31-4.17 (dd, J=10.8, 8.1 Hz, 1H), 3.96-3.70 (m, 2H), 3.63-3.45 (m, 1H), 1.55 (s, 9H).

Step E: rac-(3S,4S)-tert-butyl 3-(4-bromophenyl)-3-methyl-2-oxo-4-phenylpyrrolidine-1-carboxylate

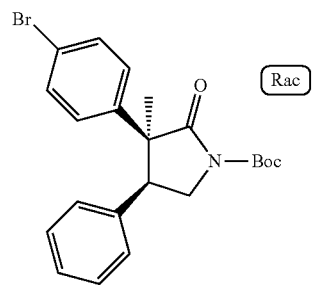 [SMILES: CC(C)(C)OC(=O)N1C[C@@H](c2ccccc2)[C@@](C)(c2ccc(Br)cc2)C1=O]

Similar to Step E of Intermediate 1 synthesis, rac-(3R,4R)-tert-butyl 3-(4-bromophenyl)-2-oxo-4-phenylpyrrolidine-1-carboxylate (1.0 g, 2.402 mmol) was converted to rac-(3S,4S)-tert-butyl 3-(4-bromophenyl)-3-methyl-2-oxo-4-phenylpyrrolidine-1-carboxylate (580 mg, 56% yield). MS (ES): m/z=376 [M−55]; ¹H NMR (400 MHz, CDCl₃): δ 7.31-7.11 (m, 5H), 6.78-6.69 (m, 2H), 6.59-6.51 (m, 2H), 4.00 (dd, J=11.2, 7.6 Hz, 1H), 3.75 (t, J=11.2 Hz, 1H), 3.43 (dd, J=11.2, 7.6 Hz, 1H), 1.60 (m, 9H), 1.53 (m, 3H)

Step F: rac-(3R,4R)-tert-butyl 3-(4-bromophenyl)-3-methyl-4-phenylpyrrolidine-1-carboxylate

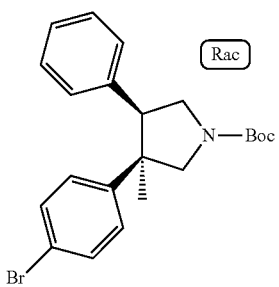 [SMILES: CC(C)(C)OC(=O)N1C[C@H](c2ccccc2)[C@](C)(c2ccc(Br)cc2)C1]

Similar to Step F of Intermediate 1 synthesis, rac-(3S,4S)-tert-butyl 3-(4-bromophenyl)-3-methyl-2-oxo-4-phenylpyrrolidine-1-carboxylate (580 mg, 1.348 mmol) was converted to rac-(3R,4R)-tert-butyl 3-(4-bromophenyl)-3-methyl-4-phenylpyrrolidine-1-carboxylate (210 mg, 37% yield). MS (ES): m/z=362 [M−55]; LC retention time: 21.32 min (analytical HPLC Method A); ¹H NMR (400 MHz, CDCl₃): δ 7.33-7.22 (m, 2H), 7.22-7.08 (m, 3H), 6.74-6.63 (m, 4H), 4.07 (dd, J=40, 11.6 Hz, 1H), 3.91-3.72 (m, 1H), 3.60-3.40 (m, 2H), 3.37-3.25 (m, 1H), 1.63-1.49 (m, 9H), 1.46 (d, J=4.13 Hz, 3H).

Example 5 rac-(3S,4S)-tert-butyl 3-(4-fluorophenyl)-4-(4-(1,1,1,3,3,3-hexafluoro-2-hydroxypropan-2-yl)phenyl)-3-methylpyrrolidine-1-carboxylate

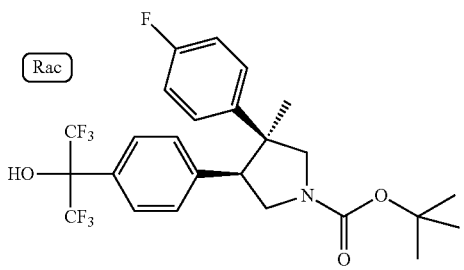 [SMILES: CC(C)(C)OC(=O)N1C[C@@H](c2ccc(C(O)(C(F)(F)F)C(F)(F)F)cc2)[C@@](C)(c2ccc(F)cc2)C1]

A 1.7 M pentane solution of tert-butyllithium (1.5 mL, 2.55 mmol) was added dropwise to a solution of Intermediate 1 (0.4 g, 0.921 mmol) in tetrahydrofuran (10 mL) under nitrogen at −78° C. The resulting yellow solution was stirred for 15 min. Anhydrous hexafluoroacetone gas was condensed (10 drops) in a Dewar condenser with acetone-dry ice and added dropwise to the lithium intermediate at −78° C. After another 20 min at −78° C., the mixture was quenched with saturated ammonium chloride (2 mL) and water (2 mL). The material was extracted with ethyl acetate (4 mL). The extract was concentrated. The resulting residue was purified by silica gel column chromatography, eluting with 0-100% ethyl acetate in hexanes, gave the title compound (0.27 g, 50.6% yield) as white solid. MS (ES): m/z=466.3 [M−55]; LC retention time: 12.969 min (analytical HPLC Method B); ¹H NMR (400 MHz, CDCl₃) δ 7.47 (d, J=8.1 Hz, 1H), 7.27 (s, 3H), 6.86-6.67 (m, 4H), 4.20-4.02 (m, 1H), 3.89-3.74 (m, 1H), 3.62-3.44 (m, 2H), 3.42-3.28 (m, 1H), 1.57 (s, 5H), 1.53 (s, 4H), 1.50 (d, J=5.9 Hz, 3H).

Examples 6 and 7

(3S,4S)-tert-butyl 3-(4-fluorophenyl)-4-(4-(1,1,1,3,3,3-hexafluoro-2-hydroxypropan-2-yl)phenyl)-3-methylpyrrolidine-1-carboxylate and (3R,4R)-tert-butyl 3-(4-fluorophenyl)-4-(4-(1,1,1,3,3,3-hexafluoro-2-hydroxypropan-2-yl)phenyl)-3-methylpyrrolidine-1-carboxylate

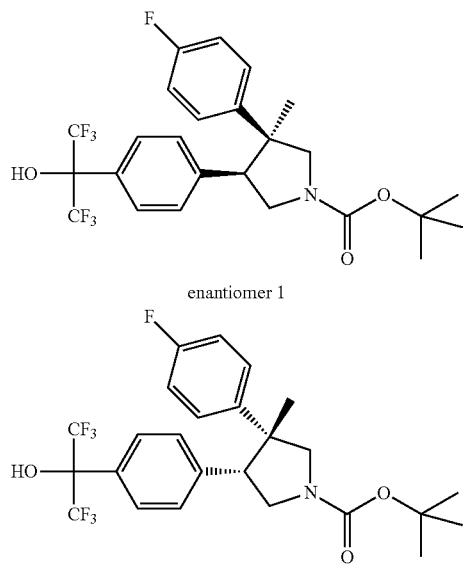

Example 5 (1.67 g) was separated into its homochiral components by preparative chiral SFC (Chiralpak AS-H 30×250 mm, 5 μm particles, 7% methanol in CO₂, 200 mL/min) to afford the first eluent off the column (0.6912 g) as Example 6 and the second eluent (0.6590 g) as Example 7. Analytical data for Example 6: Chiral HPLC retention time: 1.27 min, >99.5% pure (Chiralpak AS-H 4.6×250 mm, 5 μm particles, 7% methanol in CO₂, 3 mL/min); MS (ES): m/z=466.0 [M−55]; ¹H NMR (400 MHz, CDCl₃) δ 7.47 (d, J=8.1 Hz, 2H), 6.86-6.69 (m, 6H), 4.18-4.03 (m, 1H), 3.87-3.77 (m, 1H), 3.61-3.47 (m, 2H), 3.42-3.29 (m, 1H), 1.58-1.52 (m, 9H), 1.50 (d, J=7.3 Hz, 3H). Analytical data for Example 7: Chiral HPLC retention time: 1.63 min, 98.5% pure (Chiralpak AS-H 4.6×250 mm, 5 μm particles, 7% methanol in CO₂, 3 mL/min); MS (ES): m/z=466.0 [M−55]; ¹H NMR (400 MHz, CDCl₃) δ 7.47 (d, J=8.4 Hz, 2H), 6.85-6.68 (m, 6H), 4.18-4.03 (m, 1H), 3.86-3.77 (m, 1H), 3.61-3.47 (m, 3H), 3.41-3.30 (m, 1H), 1.58-1.52 (m, 9H), 1.50 (d, J=7.3 Hz, 3H).

Similar to the synthesis of Example 5, Examples in Table 3 were prepared from their phenyl bromide precursors.

TABLE 3

| Example number | Structure | MS observed | HPLC ret time (min.) | HPLC method |
|---|---|---|---|---|
| 8 | Rac | 434.0 (M − 55) | 1.16 | E |
| 9 | Rac | 462.4 (M − 55) | 1.19 | E |
| 10 | Rac | 488.9 (M − 14) | 2.42 | C |
| 11 | Rac | 448.3 (M − 55) | 1.16 | E |
| 12 | 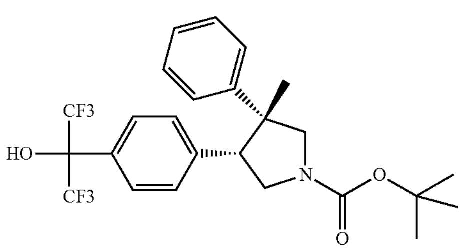 [SMILES: CC(C)(C)OC(=O)N1C[C@H](c2ccc(C(O)(C(F)(F)F)C(F)(F)F)cc2)[C@](C)(c2ccccc2)C1] | 448.1 (M − 55) | 1.17 | E |
| 13 | 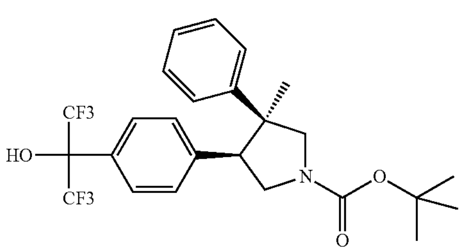 [SMILES: CC(C)(C)OC(=O)N1C[C@@H](c2ccc(C(O)(C(F)(F)F)C(F)(F)F)cc2)[C@@](C)(c2ccccc2)C1] | 448.0 (M − 55) | 1.15 | E |

TABLE 3-continued

| Example number | Structure | MS observed | HPLC ret time (min.) | HPLC method |
|---|---|---|---|---|
| 14 | 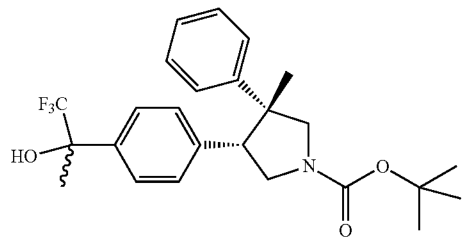 [SMILES: CC(C)(C)OC(=O)N1C[C@H](c2ccc(C(C)(O)C(F)(F)F)cc2)[C@](C)(c2ccccc2)C1] | 435.2 (M − 14) | 12.611 | B |
| 15 | 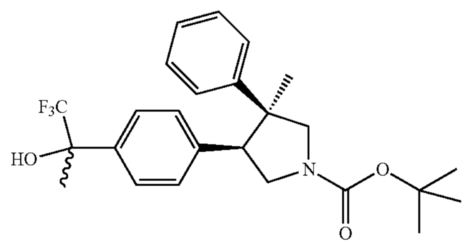 [SMILES: CC(C)(C)OC(=O)N1C[C@@H](c2ccc(C(C)(O)C(F)(F)F)cc2)[C@@](C)(c2ccccc2)C1] | 435.2 (M − 14) | 12.594 | B |
| 16 | 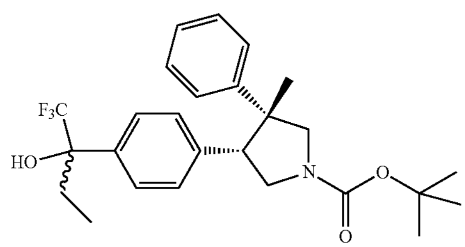 [SMILES: CCC(O)(c1ccc([C@H]2CN(C(=O)OC(C)(C)C)C[C@@]2(C)c2ccccc2)cc1)C(F)(F)F] | 408.3 (M − 55) | 13.139 | B |
| 17 | 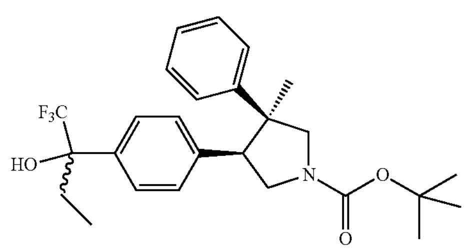 [SMILES: CCC(O)(c1ccc([C@@H]2CN(C(=O)OC(C)(C)C)C[C@]2(C)c2ccccc2)cc1)C(F)(F)F] | 408.3 (M − 55) | 13.131 | B |

Example 18 rac-((3S,4R)-1-benzyl-4-(4-bromophenyl)pyrrolidin-3-yl)(phenyl)methanone

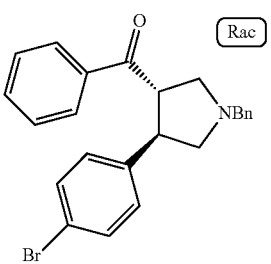 [SMILES: O=C(c1ccccc1)[C@@H]1CN(Cc2ccccc2)C[C@H]1c1ccc(Br)cc1]

Step A: (E)-3-(4-bromophenyl)-1-phenylprop-2-en-1-one

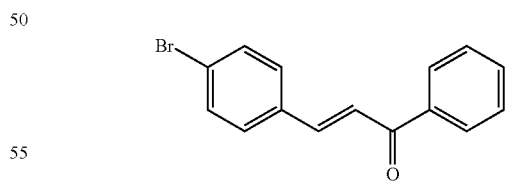

Similar to Step A of Intermediate 4, 4-bromobenzaldehyde (20.0 g, 108 mmol) and acetophenone (12.99 g, 108 mmol) were converted to (E)-3-(4-bromophenyl)-1-phenylprop-2-en-1-one (29.5 g, 95% yield) as tan solid. MS (ES): m/z=286.9, 288.9 [M+1]; $^1$H NMR (500 MHz, CDCl$_3$) δ 8.06-7.97 (m, 2H), 7.74 (d, J=15.5 Hz, 1H), 7.64-7.46 (m, 8H).

Step B: rac-((3S,4R)-1-benzyl-4-(4-bromophenyl)pyrrolidin-3-yl)(phenyl)methanone

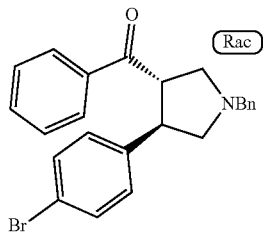 [SMILES: O=C(c1ccccc1)[C@@H]1CN(Cc2ccccc2)C[C@H]1c1ccc(Br)cc1]

Similar to Step B of Intermediate 4, (E)-3-(4-bromophenyl)-1-phenylprop-2-en-1-one (8 g, 27.9 mmol) was converted to rac-((3S,4R)-1-benzyl-4-(4-bromophenyl)pyrrolidin-3-yl)(phenyl)methanone (8.99 g, 72% yield) as white solid. MS (ES): m/z=419.9, 421.9 [M+1]; LC retention time: 3.456 min (analytical HPLC Method D); $^1$H NMR (400 MHz, CDCl$_3$) δ 7.80 (dd, J=8.4, 1.3 Hz, 2H), 7.59-7.46 (m, 1H), 7.42-7.28 (m, 8H), 7.27-7.17 (m, 3H), 3.94 (td, J=7.7, 6.9 Hz, 1H), 3.87-3.80 (m, 1H), 3.77-3.61 (m, 2H), 3.25 (t, J=8.9 Hz, 1H), 3.04-2.94 (m, 1H), 2.87 (dd, J=9.4, 5.2 Hz, 1H), 2.77 (dd, J=9.2, 7.5 Hz, 1H).

Examples 19 and 20

Diastereomers 1 and 2 of (S)-((3S,4R)-1-benzyl-4-(4-bromophenyl)pyrrolidin-3-yl)(phenyl)methanol

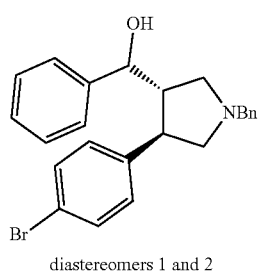 [SMILES: OC(c1ccccc1)[C@@H]1CN(Cc2ccccc2)C[C@H]1c1ccc(Br)cc1]

diastereomers 1 and 2

Similar to Step C of Intermediate 4, Example 18 (3.8 g, 9.04 mmol) was converted to the title compounds. Silica gel chromatography, eluting with 5-50% ethyl acetate in hexanes, gave the first peak as Example 19 (2.897 g, 76% yield), and the second peak as Example (0.888 g, 22% yield). Analytical data for Example 19: MS (ES): m/z=422.2, 424.2 [M+1]; LC retention time: 3.443 min (analytical HPLC Method D); $^1$H NMR (400 MHz, CDCl$_3$) δ 7.38-7.14 (m, 12H), 6.79-6.62 (m, 2H), 4.94 (d, J=4.0 Hz, 1H), 4.57 (br. s., 1H), 3.78-3.58 (m, 2H), 3.41-3.19 (m, 2H), 3.00 (dd, J=9.4, 1.7 Hz, 1H), 2.72 (dd, J=9.3, 7.0 Hz, 1H), 2.53-2.42 (m, 1H), 2.35 (dd, J=8.7, 7.3 Hz, 1H). Analytical data for Example 20: MS (ES): m/z=422.2, 424.2 [M+1]; LC retention time: 3.390 min (analytical HPLC Method D); $^1$H NMR (400 MHz, CDCl$_3$) δ 7.39-7.31 (m, 6H), 7.30-7.14 (m, 6H), 7.04-6.93 (m, 2H), 4.79 (d, J=4.4 Hz, 1H), 4.23 (br. s., 1H), 3.73-3.56 (m, 2H), 3.44-3.34 (m, 1H), 3.32-3.22 (m, 1H), 2.93 (dd, J=9.6, 2.5 Hz, 1H), 2.55 (dd, J=9.5, 7.1 Hz, 1H), 2.50-2.42 (m, 1H), 2.36 (dd, J=9.0, 7.7 Hz, 1H).

Example 21 rac-(3S,4R)-1,3-dibenzyl-4-(4-bromophenyl)pyrrolidine

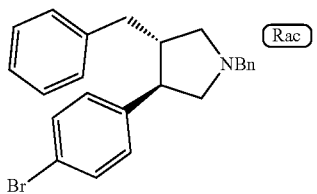 [SMILES: Brc1ccc([C@@H]2CN(Cc3ccccc3)C[C@H]2Cc2ccccc2)cc1]

Triethylsilane (25 mL) and boron trifluoride diethyl etherate (25 mL) were added to a mixture of Examples 19 and 20 (5.070 g, 12.00 mmol) in dichloromethane (25 mL). The resulting solution was stirred at room temperature under nitrogen for 60 h, then at reflux for 45 h. The mixture was concentrated, diluted with chloroform (100 mL) and water (100 mL). Solid potassium carbonate (40 g) was added in small portions to the vigorously stirred mixture. After completion of addition (pH 9-10), the mixture was stirred for 30 min and filtered over a pad of celite. The pad was rinsed with chloroform (100 mL). The two phases of the filtrate were separated. The aqueous phase was extracted with chloroform (2×100 mL). The combined chloroform phase was washed with 1:1 mixture of water-brine (20 mL), dried (magnesium sulfate) and concentrated. Silica gel chromatography, eluting with 5-40% ethyl acetate in hexanes, gave rac-(3S,4R)-1,3-dibenzyl-4-(4-bromophenyl)pyrrolidine (3.996 g, 82% yield). MS (ES): m/z=406.2, 408.2 [M+1]; LC retention time: 3.653 min (analytical HPLC Method D); $^1$H NMR (400 MHz, CDCl$_3$) δ 7.39-7.27 (m, 6H), 7.26-7.10 (m, 4H), 7.08-7.00 (m, 4H), 3.74-3.53 (m, 2H), 2.97-2.85 (m, 3H), 2.83-2.76 (m, 1H), 2.74-2.61 (m, 2H), 2.54-2.36 (m, 2H).

Example 22 rac-(3S,4S)-3-(4-fluorophenyl)-4-(4-(1,1,1,3,3,3-hexafluoro-2-hydroxypropan-2-yl)phenyl)-3-methylcyclopentanone

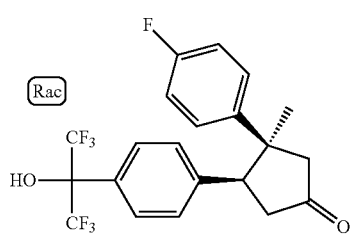

Step A: tert-butyl(1,1,1,3,3,3-hexafluoro-2-(4-vinylphenyl)propan-2-yloxy)dimethylsilane

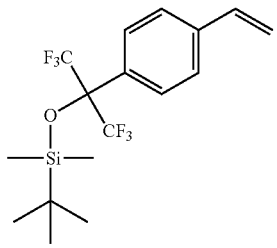 [SMILES: C=Cc1ccc(C(O[Si](C)(C)C(C)(C)C)(C(F)(F)F)C(F)(F)F)cc1]

DMAP (0.023 g, 0.185 mmol) was added to a dichloromethane (8 mL) solution of 1,1,1,3,3,3-hexafluoro-2-(4-vinylphenyl)propan-2-ol (0.5 g, 1.851 mmol from SynQuest Laboratories), tert-butylchlorodimethylsilane (0.307 g, 2.036 mmol) and triethylamine (0.516 mL, 3.70 mmol). The mixture was stirred at room temperature for 4 days. Additional DMAP (0.027 g), 1,1,1,3,3,3-hexafluoro-2-(4-vinylphenyl)propan-2-ol (0.307 g) and triethylamine (0.516 mL) were added and the mixture was stirred at room temperature for additional 2 days. The crude was quenched with saturated sodium bicarbonate (10 mL) and diluted with dichloromethane (8 mL). After phase separation, the dichloromethane layer was concentrated. Silica gel chromatography, eluting with 0-10% ethyl acetate in hexanes, gave tert-butyl(1,1,1,3,3,3-hexafluoro-2-(4-vinylphenyl)propan-2-yloxy)dimethylsilane (0.5214 g, 73% yield) as colorless oil. $^1$H NMR (400 MHz, CDCl$_3$) δ 7.66 (d, J=8.4 Hz, 2H), 7.46 (d, J=8.6 Hz, 2H), 6.74 (dd, J=17.6, 11.0 Hz, 1H), 5.83 (d, J=17.6 Hz, 1H), 5.35 (d, J=10.8 Hz, 1H), 1.02 (s, 9H), 0.16 (s, 6H).

Step B: rac-(2S,3S)-3-(4-(2-(tert-butyldimethylsilyloxy)-1,1,1,3,3,3-hexafluoropropan-2-yl)phenyl)-2-(4-fluorophenyl)-2-methylcyclobutanone

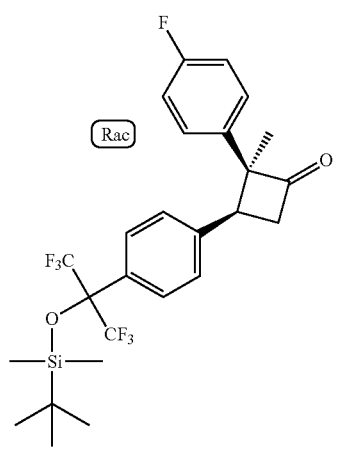 [SMILES: CC(C)(C)[Si](C)(C)OC(c1ccc([C@@H]2CC(=O)[C@]2(C)c2ccc(F)cc2)cc1)(C(F)(F)F)C(F)(F)F]

To a reflux CF$_3$Ph (2 mL) solution of tert-butyl((1,1,1,3,3,3-hexafluoro-2-(4-vinylphenyl)propan-2-yl)oxy)dimethylsilane (0.5214 g, 1.356 mmol) was added 1-diazo-1-(4-fluorophenyl)propan-2-one (0.41 g, 2.301 mmol from Intermediate 31) in CF$_3$Ph (7 mL) dropwise in 70 min under nitrogen. The syringe was rinsed with PhCF$_3$ (2 mL) and the rinse was added to the reaction. The mixture was heated at reflux for 9 h. Additional 1-diazo-1-(4-fluorophenyl)propan-2-one (0.2676 g) in CF$_3$Ph (5 mL) was added in 85 min. The mixture was heated at reflux for additional 14 h then concentrated. Silica gel chromatography, eluting with 0-50% diethyl ether in hexanes, gave rac-(2S,3S)-3-(4-(2-(tert-butyldimethylsilyloxy)-1,1,1,3,3,3-hexafluoropropan-2-yl)phenyl)-2-(4-fluorophenyl)-2-methylcyclobutanone (0.2823 g, 39%) as yellow oil. $^1$H NMR (400 MHz, CDCl$_3$) δ 7.45 (d, J=8.1 Hz, 2H), 6.96 (d, J=8.4 Hz, 2H), 6.84-6.78 (m, 2H), 6.75-6.69 (m, 2H), 3.71-3.55 (m, 2H), 3.36 (dd, J=17.5, 7.2 Hz, 1H), 1.72 (s, 3H), 0.98 (s, 9H), 0.08 (s, 3H), 0.03 (s, 3H).

Step C: rac-(3S,4S)-3-(4-fluorophenyl)-4-(4-(1,1,1,3,3,3-hexafluoro-2-hydroxypropan-2-yl)phenyl)-3-methylcyclopentanone

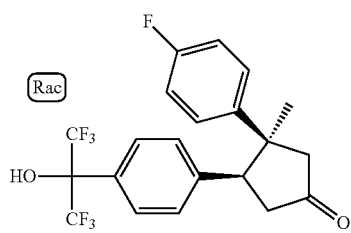

A 2 M tetrahydrofuran/heptane/ethylbenzene solution of lithium diisopropylamide (0.098 mL, 0.196 mmol) was added to a stirred tetrahydrofuran (0.5 mL) solution of 1-chloro-2-(methylsulfinyl)benzene (34.3 mg, 0.196 mmol, from Intermediate 32) at −78° C. under nitrogen. After 19 min, a tetrahydrofuran (0.5 mL) solution of rac-(2S,3S)-3-(4-(2-((tert-butyldimethylsilyl)oxy)-1,1,1,3,3,3-hexafluoropropan-2-yl)phenyl)-2-(4-fluorophenyl)-2-methylcyclobutanone (70 mg, 0.131 mmol) was added dropwise at −78° C. After 17 min, the dry ice bath was removed and the mixture was stirred at ambient temperature for 47 min. The reaction mixture was quenched with saturated ammonium chloride (4 mL) and extracted with ether (6 mL). The ether layer was separated, dried over sodium sulfate and filtered. The filtrate was concentrated. The crude intermediate was dried in vacuo overnight. The resulting residue (86 mg) was dissolved in tetrahydrofuran (1 mL) and added to a tetrahydrofuran slurry of KH (31.5 mg, 0.786 mmol) (freshly washed with dry toluene and tetrahydrofuran, the amount is based on estimation, no attempt to measure the accurate amount because of the air sensitivity of the KH). The mixture was stirred at room temperature for 1 h. The reaction was quenched by adding saturated ammonium chloride (2 mL) dropwise under nitrogen. The layers were separated. The aqueous layer was extracted with ether (4 mL). The combined organic layers were concentrated. Silica gel chromatography, eluting with 0-50% diethyl ether in hexanes, gave impure product (3.4 mg). It was further purified by HPLC (Column: Phenomenex Luna C18 S5, 21×100 mm; Mobile Phase A: 10:90 methanol:water with 0.1% TFA; Mobile Phase B: 90:10 methanol:water with 0.1% TFA. Flow: 20 mL/min) to yield rac-(3S,4S)-3-(4-fluorophenyl)-4-(4-(1,1,1,3,3,3-hexafluoro-2-hydroxypropan-2-yl)phenyl)-3-methylcyclopentanone (1.3 mg, 2% yield) as white lyopholized powder. MS (ES): m/z=435.1 [M+1]; LC retention time: 11.608 min (analytical HPLC Method B); $^1$H NMR (400 MHz, CDCl$_3$) δ 7.55-7.43 (m, 2H), 6.85-6.72 (m, 4H), 6.69-6.58 (m, 2H), 3.55 (d, J=9.0 Hz, 1H), 3.10 (d, J=18.7 Hz, 1H), 2.66-2.48 (m, 3H), 1.64 (br. s., 3H).

Example 23 rac-1-(4-((3R,4S)-3-(4-fluorophenyl)-4-(4-(1,1,3,3,3-hexafluoro-2-hydroxypropan-2-yl)phenyl)-3-(hydroxymethyl)pyrrolidine-1-carbonyl)piperidin-1-yl)ethanone

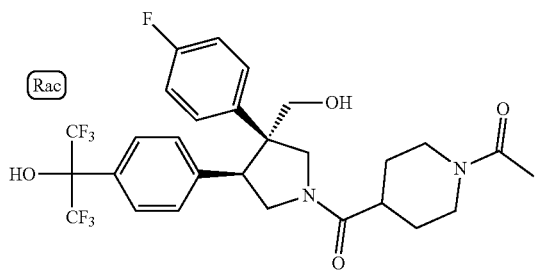 [SMILES: CC(=O)N1CCC(C(=O)N2C[C@@H](c3ccc(C(O)(C(F)(F)F)C(F)(F)F)cc3)[C@@](CO)(c3ccc(F)cc3)C2)CC1]

Step A: rac-1-(4-((3R,4S)-3-(benzyloxymethyl)-3-(4-fluorophenyl)-4-(4-(1,1,1,3,3,3-hexafluoro-2-hydroxypropan-2-yl)phenyl)pyrrolidine-1-carbonyl)piperidin-1-yl)ethanone

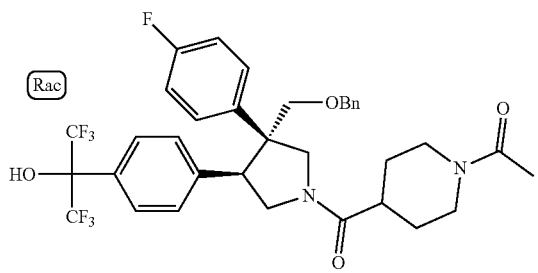 [SMILES: CC(=O)N1CCC(C(=O)N2C[C@@H](c3ccc(C(O)(C(F)(F)F)C(F)(F)F)cc3)[C@@](COCc3ccccc3)(c3ccc(F)cc3)C2)CC1]

1-Acetylpiperidine-4-carbonyl chloride (2.069 mg, 10.91 µmol) was added to a stirred acetonitrile (0.5 mL) solution of rac-2-(4-((3R,4S)-4-((benzyloxy)methyl)-4-(4-fluorophenyl)pyrrolidin-3-yl)phenyl)-1,1,1,3,3,3-hexafluoropropan-2-ol trifluoroacetic acid salt (7 mg, 10.91 µmol, from Intermediate 24) and triethylamine (0.015 mL, 0.109 mmol) at room temperature. The mixture was stirred for 10 min then concentrated. Silica gel chromatography, eluting with 0-10% methanol in dichloromethane with 2 M NH4OH, gave rac-1-(4-((3R,4S)-3-(benzyloxymethyl)-3-(4-fluorophenyl)-4-(4-(1,1,1,3,3,3-hexafluoro-2-hydroxypropan-2-yl)phenyl)pyrrolidine-1-carbonyl)piperidin-1-yl)ethanone (5.7 mg, 77% yield) as white solid. MS (ES): m/z=681.0 [M+1]; $^1$H NMR (400 MHz, CDCl$_3$) δ 7.50 (d, J=6.2 Hz, 1H), 7.45 (d, J=7.9 Hz, 1H), 7.41-7.29 (m, 7H), 6.84-6.74 (m, 2H), 6.71-6.60 (m, 2H), 4.58 (d, J=4.8 Hz, 2H), 4.32-3.55 (m, 9H), 3.22-3.02 (m, 1H), 2.80-2.57 (m, 2H), 2.16-2.09 (m, 3H), 1.97-1.72 (m, 4H).

Step B: rac-1-(4-((3R,4S)-3-(4-fluorophenyl)-4-(4-(1,1,1,3,3,3-hexafluoro-2-hydroxypropan-2-yl)phenyl)-3-(hydroxymethyl)pyrrolidine-1-carbonyl)piperidin-1-yl)ethanone

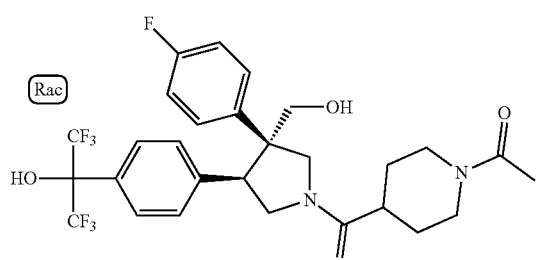

A methanol (1 mL) solution of rac-1-(4-((3R,4S)-3-(benzyloxymethyl)-3-(4-fluorophenyl)-4-(4-(1,1,1,3,3,3-hexafluoro-2-hydroxypropan-2-yl)phenyl)pyrrolidine-1-carbonyl)piperidin-1-yl)ethanone (5.7 mg, 8.37 µmol) and Pearlman's catalyst (4.8 mg, 6.84 µmol) was stirred under a H2 balloon pressure at room temperature. After 1 h, the crude was filtered. The filtrate was concentrated. Silica gel chromatography, eluting with 0-20% methanol in dichloromethane with 2 M NH4OH, gave rac-1-(4-((3R,4S)-3-(4-fluorophenyl)-4-(4-(1,1,1,3,3,3-hexafluoro-2-hydroxypropan-2-yl)phenyl)-3-(hydroxymethyl)pyrrolidine-1-carbonyl)piperidin-1-yl)ethanone (2.7 mg, 55% yield) as white solid. MS (ES): m/z=591.0 [M+1]; LC retention time: 8.608 min (analytical HPLC Method B); $^1$H NMR (500 MHz, CDCl$_3$) δ 7.57-7.52 (m, 1H), 7.50 (d, J=8.3 Hz, 1H), 6.89-6.82 (m, 3H), 6.79 (dd, J=8.6, 3.1 Hz, 1H), 6.76-6.70 (m, 2H), 4.69-4.58 (m, 1H), 4.30 (dd, J=12.9, 1.5 Hz, 1H), 4.18 (s, 1H), 4.07-3.83 (m, 5H), 3.75-3.55 (m, 1H), 3.22-3.05 (m, 1H), 2.84-2.58 (m, 2H), 2.15-2.09 (m, 3H), 2.02-1.69 (m, 5H).

Example 24 rac-(3R,4S)—N-benzyl-3-(4-fluorophenyl)-4-(4-(1,1,3,1,3,3,3-hexafluoro-2-hydroxypropan-2-yl)phenyl)-3-(hydroxymethyl)pyrrolidine-1-carboxamide

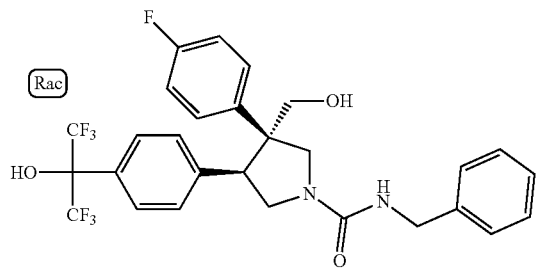 [SMILES: O=C(NCc1ccccc1)N1C[C@@H](c2ccc(C(O)(C(F)(F)F)C(F)(F)F)cc2)[C@@](CO)(c2ccc(F)cc2)C1]

Step A: rac-1,1,1,3,3,3-hexafluoro-2-(4-((3S,4R)-4-(4-fluorophenyl)-4-(hydroxymethyl)pyrrolidin-3-yl)phenyl)propan-2-ol

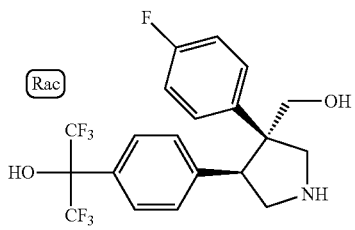 [SMILES: OC[C@]1(c2ccc(F)cc2)CNC[C@H]1c1ccc(C(O)(C(F)(F)F)C(F)(F)F)cc1]

A methanol (0.5 mL) solution of rac-2-(4-((3R,4S)-4-((benzyloxy)methyl)-4-(4-fluorophenyl)pyrrolidin-3-yl)phenyl)-1,1,1,3,3,3-hexafluoropropan-2-ol trifluoroacetic acid salt (Intermediate 24, 7 mg, 10.91 μmol) and Pearlman's catalyst (4.8 mg, 6.84 μmol) was stirred under H2 balloon pressure at room temperature for 18 h. The crude was filtered and the filtrate was concentrated to give the crude rac-1,1,1,3,3,3-hexafluoro-2-(4-((3S,4R)-4-(4-fluorophenyl)-4-(hydroxymethyl)pyrrolidin-3-yl)phenyl)propan-2-ol (4.4 mg) as colorless oil. MS (ES): m/z=438.0 [M+1].

Step B: rac-(3R,4S)—N-benzyl-3-(4-fluorophenyl)-4-(4-(1,1,1,3,3,3-hexafluoro-2-hydroxypropan-2-yl)phenyl)-3-(hydroxymethyl)pyrrolidine-1-carboxamide

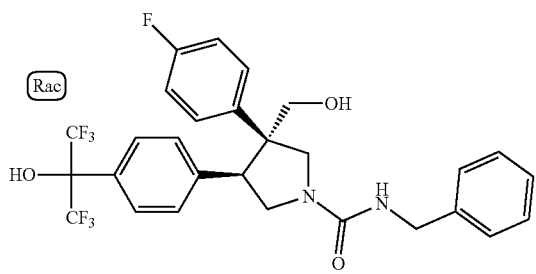 [SMILES: O=C(NCc1ccccc1)N1C[C@@H](c2ccc(C(O)(C(F)(F)F)C(F)(F)F)cc2)[C@@](CO)(c2ccc(F)cc2)C1]

(Isocyanatomethyl)benzene (1.5 μL, 0.012 mmol) was added to a dichloromethane (0.5 mL) solution of the crude rac-1,1,1,3,3,3-hexafluoro-2-(4-((3S,4R)-4-(4-fluorophenyl)-4-(hydroxymethyl)pyrrolidin-3-yl)phenyl)propan-2-ol (4.4 mg, assuming 0.008 mmol) and triethylamine (10 μL, 0.072 mmol). The mixture was stirred at room temperature for 1 h then concentrated. Silica gel chromatography, eluting with 0-20% methanol in dichloromethane, gave impure product (3.7 mg). It was further purified by preparative HPLC (Column: Phenomenex Luna C18 S5, 21×100 mm; Mobile Phase A: 10:90 methanol:water with 0.1% TFA; Mobile Phase B: 90:10 methanol:water with 0.1% TFA. Flow: 20 mL/min) to yield rac-(3R,4S)—N-benzyl-3-(4-fluorophenyl)-4-(4-(1,1,1,3,3,3-hexafluoro-2-hydroxypropan-2-yl)phenyl)-3-(hydroxymethyl)pyrrolidine-1-carboxamide (1.2 mg, 17% yield over 2 steps) as white solid. MS (ES): m/z=571.0 [M+1]; LC retention time: 10.091 min (analytical HPLC Method B); $^1$H NMR (500 MHz, 1:1 mixture of CDCl$_3$-CD3OD) δ 7.46 (d, J=8.3 Hz, 2H), 7.36-7.28 (m, 5H), 7.25-7.20 (m, 1H), 6.84-6.79 (m, 2H), 6.78-6.73 (m, 3H), 4.44 (s, 2H), 4.05 (d, J=10.5 Hz, 1H), 3.91-3.80 (m, 4H), 3.74 (d, J=8.0 Hz, 1H), 3.61-3.54 (m, 1H).

Example 25 rac-1-(4-((3S,4S)-3-(4-fluorophenyl)-4-(4-(1,1,1,3,3,3-hexafluoro-2-hydroxypropan-2-yl)phenyl)-3-methylpyrrolidine-1-carbonyl)piperidin-1-yl)ethanone

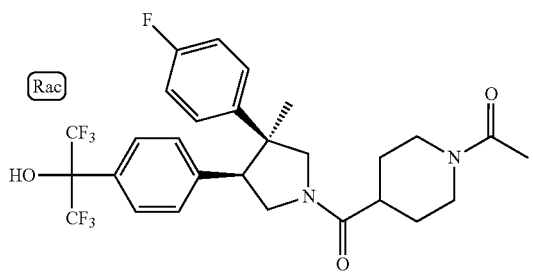 [SMILES: CC(=O)N1CCC(C(=O)N2C[C@@H](c3ccc(C(O)(C(F)(F)F)C(F)(F)F)cc3)[C@@](C)(c3ccc(F)cc3)C2)CC1]

Triethylamine (0.013 mL, 0.093 mmol) was added to a dichloromethane (0.5 mL) suspension of Intermediate 11 (10 mg, 0.019 mmol) and 1-acetylpiperidine-4-carbonyl chloride (4.7 mg, 0.025 mmol). The mixture was stirred at room temperature for 70 min. Additional 1-acetylpiperidine-4-carbonyl chloride (4.7 mg) and triethylamine (0.013 mL) were added. The mixture was stirred for additional 50 min. The solvent was evaporated and the crude was diluted with methanol (1 mL) and purified by preparative HPLC (Waters XBridge C18, 19×150 mm, 5-m particles; Mobile Phase A: 5:95 acetonitrile:water with 10-mM ammonium acetate; Mobile Phase B: 95:5 acetonitrile:water with 10-mM ammonium acetate. Flow: 20 mL/min) to give the title compound (9.1 mg, 84% yield). MS (ES): m/z=575.2 [M+1]; LC retention time: 1.79 min (analytical HPLC Method C); $^1$H NMR (500 MHz, 1:1 mixture of CDCl$_3$-CD3OD) δ 7.48 (dd, J=19.6, 8.2 Hz, 2H), 6.85-6.63 (m, 6H), 4.64-4.53 (m, 1H), 4.32-4.24 (m, 2H), 4.07-3.91 (m, 2H), 3.85-3.70 (m, 1H), 3.66-3.38 (m, 2H), 3.26-3.09 (m, 1H), 2.84-2.61 (m, 1H), 2.12 (m, 3H), 2.02-1.64 (m, 4H), 1.58-1.48 (m, 3H).

Example 26

(3S,4S)-methyl 4-(4-(1,1,1,3,3,3-hexafluoro-2-hydroxypropan-2-yl)phenyl)-3-methyl-3-phenylpyrrolidine-1-carboxylate

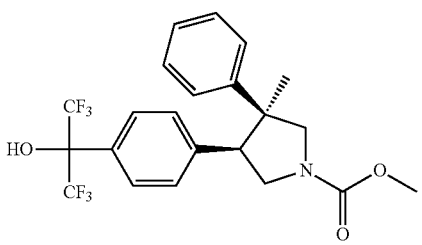 [SMILES: COC(=O)N1C[C@@H](c2ccc(C(O)(C(F)(F)F)C(F)(F)F)cc2)[C@@](C)(c2ccccc2)C1]

Methyl carbonochloridate (2.231 μL, 0.029 mmol) was added to an acetonitrile (0.5 mL) solution of Intermediate 17 (7.5 mg, 0.014 mmol) and triethylamine (7 μL, 0.050 mmol). The mixture was stirred at room temperature for 25 min. The crude was diluted with methanol (1 mL) and filtered. The filtrate was purified by preparative HPLC (Waters XBridge C18, 19×150 mm, 5-μm particles; Mobile Phase A: 5:95 acetonitrile:water with 10-mM ammonium acetate; Mobile Phase B: 95:5 acetonitrile:water with 10-mM ammonium acetate. Flow: 20 mL/min) to give the title compound (5.9 mg, 86% yield). MS (ES): m/z=462.1 [M+1]; LC retention time: 2.16 min (analytical HPLC Method C); $^1$H NMR (500 MHz, 1:1 mixture of CDCl$_3$-CD3OD) δ 7.43 (d, J=8.3 Hz, 2H), 7.12-7.05 (m, 3H), 6.79-6.70 (m, 4H), 4.16 (dd, J=15.3, 11.4 Hz, 1H), 3.89-3.81 (m, 1H), 3.79 (d, J=15.5 Hz, 3H), 3.63-3.54 (m, 2H), 3.46-3.39 (m, 1H), 1.51 (d, J=2.5 Hz, 3H).

Example 27 rac-2-(4-((3S,4S)-1-benzyl-4-methyl-4-phenylpyrrolidin-3-yl)phenyl)-1,1,1,3,3,3-hexafluoropropan-2-ol

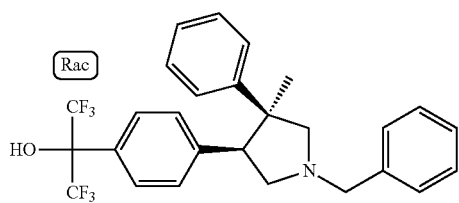 [SMILES: C[C@]1(c2ccccc2)CN(Cc2ccccc2)C[C@H]1c1ccc(C(O)(C(F)(F)F)C(F)(F)F)cc1]

Hunig's base (0.024 mL, 0.136 mmol) was added to a mixture of 1,1,1,3,3,3-hexafluoro-2-(4-((3S,4S)-4-methyl-4-phenylpyrrolidin-3-yl)phenyl)propan-2-ol HCl salt (12 mg, 0.027 mmol, from Intermediate 14) and (bromomethyl)benzene (7.00 mg, 0.041 mmol) in dichloromethane (1 mL) and tetrahydrofuran (0.5 mL). The mixture was stirred at room temperature for 16 h. The reaction was quenched with ammonium hydroxide (1 drop), stirred for 10 min and filtered. The filtrate was concentrated, dissolved in methanol (1 mL) and purified by preparative HPLC (Waters XBridge C18, 19×150 mm, 5-μm particles; Mobile Phase A: 5:95 acetonitrile:water with 10-mM ammonium acetate; Mobile Phase B: 95:5 acetonitrile:water with 10-mM ammonium acetate. Flow: 20 mL/min) to give the title compound (11.4 mg, 83% yield). MS (ES): m/z=494.1 [M+1]; LC retention time: 2.65 min (analytical HPLC Method C); $^1$H NMR (500 MHz, 1:1 mixture of CDCl$_3$-CD3OD) δ 7.47 (d, J=6.9 Hz, 2H), 7.41-7.33 (m, 4H), 7.32-7.26 (m, 1H), 7.03-6.93 (m, 5H), 6.83 (d, J=8.4 Hz, 2H), 4.00-3.88 (m, 2H), 3.51 (d, J=10.4 Hz, 1H), 3.45 (t, J=8.2 Hz, 1H), 3.23 (dd, J=9.9, 7.9 Hz, 1H), 3.14-3.06 (m, 1H), 2.99 (d, J=9.9 Hz, 1H), 1.61 (s, 3H).

Example 28 rac-2-((3S,4S)-4-(4-(1,1,1,3,3,3-hexafluoro-2-hydroxypropan-2-yl)phenyl)-3-methyl-3-phenylpyrrolidin-1-yl)acetamide

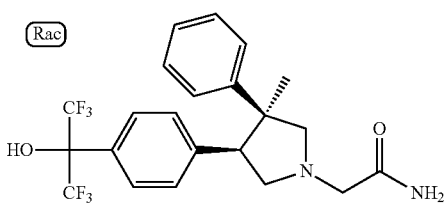 [SMILES: C[C@]1(c2ccccc2)CN(CC(N)=O)C[C@H]1c1ccc(C(O)(C(F)(F)F)C(F)(F)F)cc1]

Similar to the synthesis of Example 27, Intermediate 14 (12 mg, 0.027 mmol) was reacted with 2-bromoacetamide (5.65 mg, 0.041 mmol) to give the title compound (10.2 mg, 81% yield). MS (ES): m/z=461.1 [M+1]; LC retention time: 1.83 min (analytical HPLC Method C); $^1$H NMR (500 MHz, 1:1 mixture of CDCl$_3$-CD3OD) δ 7.39 (d, J=8.4 Hz, 2H), 7.08-7.00 (m, 3H), 6.96 (dd, J=7.7, 1.7 Hz, 2H), 6.84 (d, J=8.4 Hz, 2H), 3.61 (d, J=9.4 Hz, 1H), 3.52-3.47 (m, 1H), 3.45 (d, J=2.0 Hz, 2H), 3.30 (dd, J=9.7, 8.2 Hz, 1H), 3.19-3.13 (m, 1H), 3.10 (d, J=9.9 Hz, 1H), 1.61 (s, 3H).

Example 29

2-((3S,4S)-4-(4-(1,1,1,3,3,3-hexafluoro-2-hydroxypropan-2-yl)phenyl)-3-methyl-3-phenylpyrrolidin-1-yl)pyrimidine-5-carbonitrile

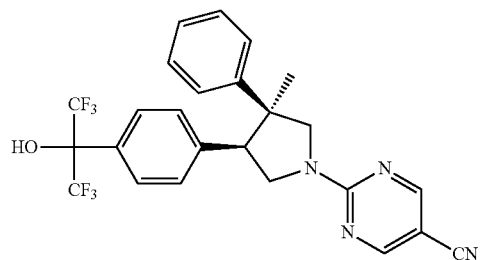 [SMILES: C[C@]1(c2ccccc2)CN(c2ncc(C#N)cn2)C[C@H]1c1ccc(C(O)(C(F)(F)F)C(F)(F)F)cc1]

A stirred acetonitrile (0.5 mL) solution of 1,1,1,3,3,3-hexafluoro-2-(4-((3S,4S)-4-methyl-4-phenylpyrrolidin-3-yl)phenyl)propan-2-ol trifluoroacetic acid salt (7.5 mg, 0.014 mmol, from Intermediate 17), 2-chloropyrimidine-5-carbonitrile (5.6 mg, 0.040 mmol) and triethylamine (10.10 μL, 0.072 mmol) was heated in a sealed vial at 90° C. for 30 min. The crude was diluted with methanol (1 mL) and filtered. The filtrate was purified by preparative HPLC (Waters XBridge C18, 19×150 mm, 5-m particles; Mobile Phase A: 5:95 acetonitrile:water with 10-mM ammonium acetate; Mobile Phase B: 95:5 acetonitrile:water with 10-mM ammonium acetate. Flow: 20 mL/min) to give the title compound (5.9 mg, 77% yield). MS (ES): m/z=507.1 [M+1]; LC retention time: 2.31 min (analytical HPLC Method C); $^1$H NMR (500 MHz, DMSO-d6) δ 8.85 (d, J=2.7 Hz, 1H), 8.81 (d, J=2.7 Hz, 1H), 7.40 (d, J=8.1 Hz, 2H), 7.11-7.05 (m, 3H), 6.92 (d, J=8.4 Hz, 2H), 6.77 (d, J=6.4 Hz, 2H), 4.33 (d, J=12.1 Hz, 1H), 4.17-4.08 (m, 1H), 3.89-3.82 (m, 1H), 3.79-3.69 (m, 1H), 1.53 (s, 3H).

Example 30

2-((3R,4R)-4-(4-(1,1,1,3,3,3-hexafluoro-2-hydroxypropan-2-yl)phenyl)-3-methyl-3-phenylpyrrolidin-1-yl)pyrimidine-5-carbonitrile

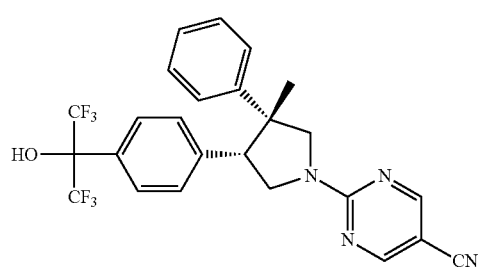 [SMILES: C[C@@]1(c2ccccc2)CN(c2ncc(C#N)cn2)C[C@@H]1c1ccc(C(O)(C(F)(F)F)C(F)(F)F)cc1]

Similar to the synthesis of Example 29, 1,1,1,3,3,3-hexafluoro-2-(4-((3R,4R)-4-methyl-4-phenylpyrrolidin-3-yl)phenyl)propan-2-ol trifluoroacetic acid salt (10 mg, 0.019 mmol, from Intermediate 16) was converted to the title compound (8.7 mg, 88% yield). MS (ES): m/z=507.1 [M+1]; LC retention time: 2.18 min (analytical HPLC Method C); $^1$H NMR (500 MHz, 1:1 mixture of CDCl$_3$-CD3OD) δ 8.69-8.58 (m, 2H), 7.45 (d, J=7.9 Hz, 2H), 7.16-7.03 (m, 3H), 6.83-6.69 (m, 4H), 4.48 (d, J=12.4 Hz, 1H), 4.38 (br. s., 1H), 4.14 (dd, J=12.1, 7.7 Hz, 1H), 3.85-3.76 (m, 2H), 3.64-3.56 (m, 1H), 1.60 (s, 3H).

Example 31

2-((3S,4S)-3-(4-fluorophenyl)-4-(4-(1,1,1,3,3,3-hexafluoro-2-hydroxypropan-2-yl)phenyl)-3-methylpyrrolidin-1-yl)pyrimidine-5-carbonitrile

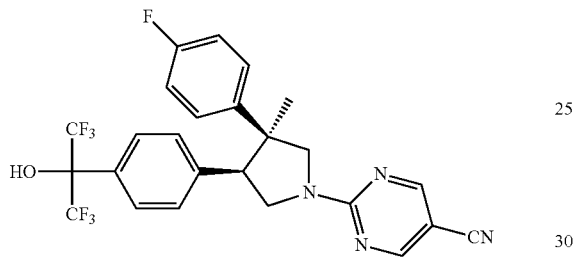

Similar to the synthesis of Example 29, 1,1,1,3,3,3-hexafluoro-2-(4-((3S,4S)-4-(4-fluorophenyl)-4-methylpyrrolidin-3-yl)phenyl)propan-2-ol trifluoroacetic acid salt (7.5 mg, 0.014 mmol, from Intermediate 18) was converted to the title compound (6.5 mg, 84% yield). MS (ES): m/z=525.1 [M+1]; LC retention time: 2.31 min (analytical HPLC Method C); $^1$H NMR (500 MHz, 1:1 mixture of CDCl$_3$-CD3OD) δ 8.69 (d, J=2.8 Hz, 1H), 8.65 (d, J=3.1 Hz, 1H), 7.49 (d, J=8.3 Hz, 2H), 6.86 (d, J=8.6 Hz, 2H), 6.81-6.76 (m, 4H), 4.45 (d, J=12.2 Hz, 1H), 4.17 (dd, J=12.2, 7.5 Hz, 1H), 3.88-3.79 (m, 2H), 3.69-3.62 (m, 1H), 1.60 (s, 3H).

Example 32

(1R,4s)-4-((3S,4S)-3-(4-fluorophenyl)-4-(4-(1,1,1,3,3,3-hexafluoro-2-hydroxypropan-2-yl)phenyl)-3-methylpyrrolidine-1-carbonyl)cyclohexanecarboxylic acid

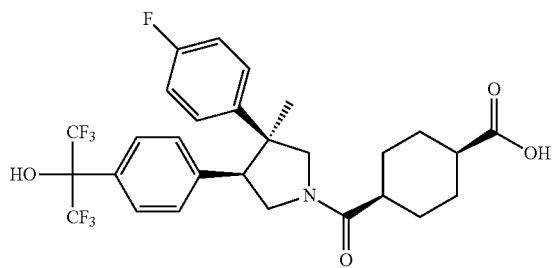 [SMILES: C[C@]1(c2ccc(F)cc2)CN(C(=O)[C@H]2CC[C@@H](C(=O)O)CC2)C[C@H]1c1ccc(C(O)(C(F)(F)F)C(F)(F)F)cc1]

An acetonitrile (0.5 mL) solution of 1,1,1,3,3,3-hexafluoro-2-(4-((3S,4S)-4-(4-fluorophenyl)-4-methylpyrrolidin-3-yl)phenyl)propan-2-ol trifluoroacetic acid salt (10 mg, 0.019 mmol, from Intermediate 18), (1s,4s)-4-(methoxycarbonyl)cyclohexanecarboxylic acid (4 mg, 0.021 mmol), BOP (10 mg, 0.023 mmol) and Hunig's base (0.016 mL, 0.093 mmol) was stirred at room temperature for 50 min. A 1 M solution of NaOH (0.5 mL, 0.5 mmol) was added and the mixture was stirred at room temperature for additional 17 h. The crude was diluted with methanol (1 mL) and purified by preparative HPLC (Waters XBridge C18, 19×150 mm, 5-m particles; Mobile Phase A: 5:95 acetonitrile:water with 10-mM ammonium acetate; Mobile Phase B: 95:5 acetonitrile:water with 10-mM ammonium acetate. Flow: 20 mL/min) to give the title compound (8.7 mg, 75% yield). MS (ES): m/z=576.3 [M+1]; LC retention time: 1.77 min (analytical HPLC Method C); $^1$H NMR (400 MHz, 1:1 mixture of CDCl$_3$-CD3OD) δ 7.48 (dd, J=16.3, 8.3 Hz, 2H), 6.84-6.71 (m, 5H), 6.70-6.64 (m, 1H), 4.29-4.20 (m, 1H), 4.03-3.91 (m, 1H), 3.81-3.67 (m, 1H), 3.64-3.37 (m, 2H), 2.68-2.49 (m, 2H), 2.34-2.20 (m, 2H), 1.89-1.45 (m, 9H).

Example 33

(1S,4r)-4-((3S,4S)-3-(4-fluorophenyl)-4-(4-(1,1,1,3,3,3-hexafluoro-2-hydroxypropan-2-yl)phenyl)-3-methylpyrrolidine-1-carbonyl)cyclohexanecarboxylic acid

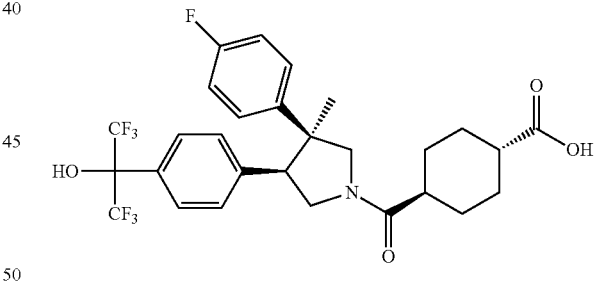

Similar to synthesis of Example 32, 1,1,1,3,3,3-hexafluoro-2-(4-((3S,4S)-4-(4-fluorophenyl)-4-methylpyrrolidin-3-yl)phenyl)propan-2-ol trifluoroacetic acid salt (10 mg, 0.019 mmol, from Intermediate 18) and (1r,4r)-4-(methoxycarbonyl) cyclohexanecarboxylic acid (4 mg, 0.021 mmol) were reacted to give the title compound (2.7 mg, 24% yield). MS (ES): m/z=576.3 [M+1]; LC retention time: 1.52 min (analytical HPLC Method C); $^1$H NMR (400 MHz, 1:1 mixture of CDCl$_3$-CD3OD) δ 7.48 (dd, J=15.2, 8.2 Hz, 2H), 6.84-6.71 (m, 5H), 6.71-6.65 (m, 1H), 4.30-4.22 (m, 1H), 4.04-3.93 (m, 1H), 3.81-3.68 (m, 1H), 3.65-3.37 (m, 2H), 2.64-2.43 (m, 1H), 2.40-2.24 (m, 1H), 2.18-1.84 (m, 4H), 1.71-1.35 (m, 7H).

Example 34

2-(4-((3S,4S)-3-(4-fluorophenyl)-4-(4-(1,1,1,3,3,3-hexafluoro-2-hydroxypropan-2-yl)phenyl)-3-methylpyrrolidine-1-carbonyl)piperidin-1-yl)pyrimidine-5-carbonitrile

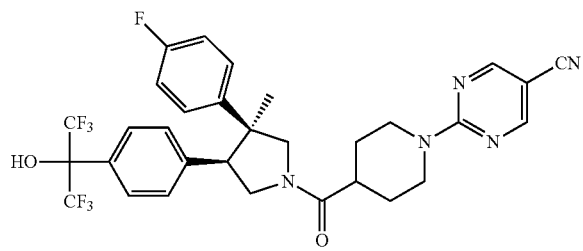 [SMILES: C[C@]1(c2ccc(F)cc2)CN(C(=O)C2CCN(c3ncc(C#N)cn3)CC2)C[C@H]1c1ccc(C(O)(C(F)(F)F)C(F)(F)F)cc1]

Similar to synthesis of Example 29, ((3S,4S)-3-(4-fluorophenyl)-4-(4-(1,1,1,3,3,3-hexafluoro-2-hydroxypropan-2-yl)phenyl)-3-methylpyrrolidin-1-yl)(piperidin-4-yl)methanone trifluoroacetic acid salt (6 mg, 9.28 µmol, from Intermediate 25) and 2-bromopyrimidine-5-carbonitrile (3.5 mg, 0.019 mmol) were reacted to give the title compound (4.7 mg, 76% yield). MS (ES): m/z=636.2 [M+1]; LC retention time: 2.23 min (analytical HPLC Method C); $^1$H NMR (500 MHz, 1:1 mixture of CDCl$_3$-CD3OD) δ 8.52 (s, 1H), 8.51 (s, 1H), 7.51 (d, J=8.3 Hz, 1H), 7.47 (d, J=8.3 Hz, 1H), 6.84-6.72 (m, 5H), 6.69 (dd, J=8.9, 5.0 Hz, 1H), 4.99-4.86 (m, 2H), 4.34-4.25 (m, 1H), 4.10-3.95 (m, 1H), 3.88-3.75 (m, 1H), 3.67-3.39 (m, 2H), 3.19-3.01 (m, 2H), 2.97-2.86 (m, 1H), 2.06-1.75 (m, 4H), 1.59-1.48 (m, 3H).

Similar to the synthesis of Examples 23-32, Examples in Table 4 were prepared by coupling appropriate amine intermediates with electrophiles such as acid, acid chloride, sulfonyl chloride, chloroformate and isocyanate reagents.

TABLE 4

| Example number | Structure | MS observed (M + 1) | HPLC ret. time (min.) | HPLC method |
|---|---|---|---|---|
| 35 | enant 1 | 487.3 | 1.71 | C |
| 36 | enant 2 | 487.3 | 1.97 | C |
| 37 | enant 1 | 521.3 | 1.93 | C |

TABLE 4-continued

| Example number | Structure | MS observed (M + 1) | HPLC ret. time (min.) | HPLC method |
|---|---|---|---|---|
| 38 | enant 2 | 521.3 | 1.93 | C |
| 39 | Rac | 501.3 | 2.32 | C |
| 40 | enant 2 | 501.4 | 2.32 | C |
| 41 | Rac | 470.3 | 1.71 | C |
| 42 | Rac | 504.4 | 1.67 | C |

TABLE 4-continued
| Example number | Structure | MS observed (M + 1) | HPLC ret. time (min.) | HPLC method |
|---|---|---|---|---|
| 43 | 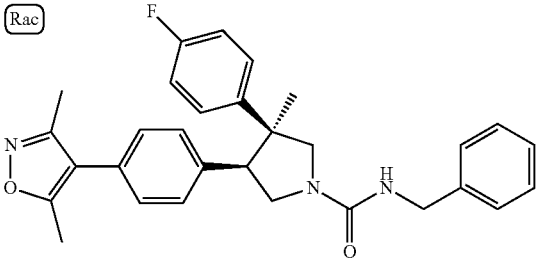 [SMILES: Cc1noc(C)c1-c1ccc([C@@H]2CN(C(=O)NCc3ccccc3)C[C@]2(C)c2ccc(F)cc2)cc1] | 484.3 | 1.98 | C |
| 44 | 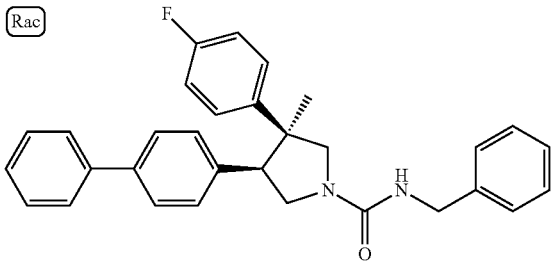 [SMILES: C[C@]1(c2ccc(F)cc2)CN(C(=O)NCc2ccccc2)C[C@H]1c1ccc(-c2ccccc2)cc1] | 465.3 | 2.25 | C |
| 45 | 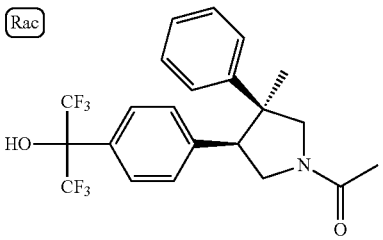 [SMILES: CC(=O)N1C[C@@H](c2ccc(C(O)(C(F)(F)F)C(F)(F)F)cc2)[C@@](C)(c2ccccc2)C1] | 446.2 | 1.80 | C |
| 46 | 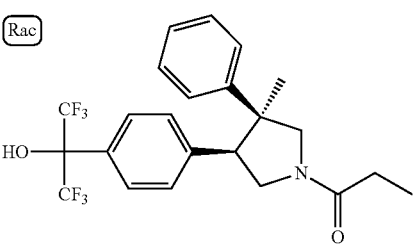 [SMILES: CCC(=O)N1C[C@@H](c2ccc(C(O)(C(F)(F)F)C(F)(F)F)cc2)[C@@](C)(c2ccccc2)C1] | 460.0 | 1.95 | C |
| 47 | 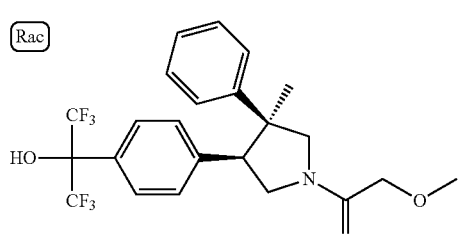 | 476.0 | 1.83 | C |
| 48 | 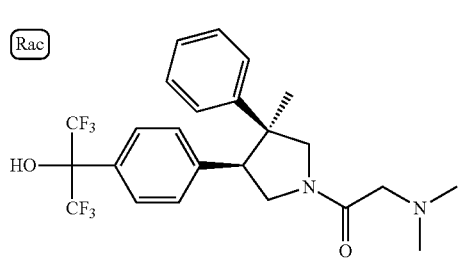 [SMILES: CN(C)CC(=O)N1C[C@@H](c2ccc(C(O)(C(F)(F)F)C(F)(F)F)cc2)[C@@](C)(c2ccccc2)C1] | 489.0 | 1.58 | C |

TABLE 4-continued
| Example number | Structure | MS observed (M + 1) | HPLC ret. time (min.) | HPLC method |
|---|---|---|---|---|
| 49 | 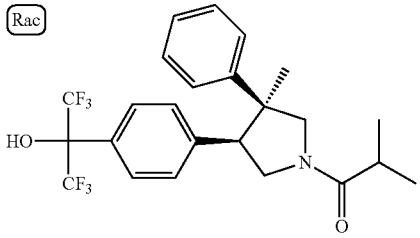 [SMILES: CC(C)C(=O)N1C[C@@H](c2ccc(C(O)(C(F)(F)F)C(F)(F)F)cc2)[C@@](C)(c2ccccc2)C1] | 474.1 | 2.05 | C |
| 50 | 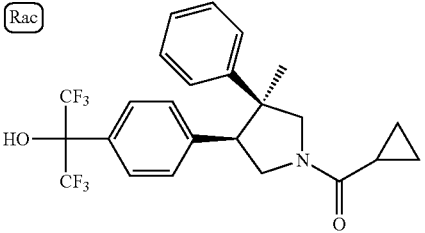 [SMILES: C[C@]1(c2ccccc2)CN(C(=O)C2CC2)C[C@H]1c1ccc(C(O)(C(F)(F)F)C(F)(F)F)cc1] | 472.1 | 2.00 | C |
| 51 | 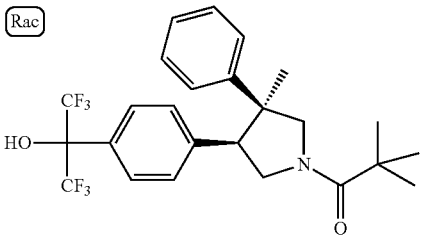 [SMILES: CC(C)(C)C(=O)N1C[C@@H](c2ccc(C(O)(C(F)(F)F)C(F)(F)F)cc2)[C@@](C)(c2ccccc2)C1] | 488.1 | 2.20 | C |
| 52 | 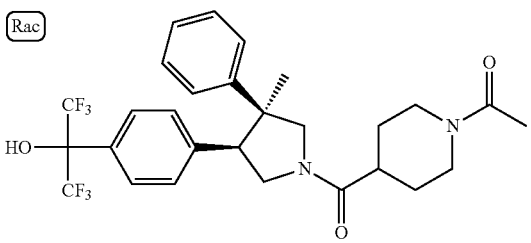 [SMILES: CC(=O)N1CCC(C(=O)N2C[C@@H](c3ccc(C(O)(C(F)(F)F)C(F)(F)F)cc3)[C@@](C)(c3ccccc3)C2)CC1] | 557.2 | 1.78 | C |
| 53 | 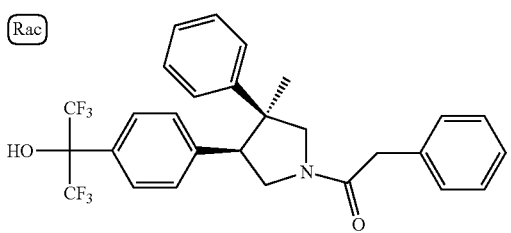 [SMILES: C[C@]1(c2ccccc2)CN(C(=O)Cc2ccccc2)C[C@H]1c1ccc(C(O)(C(F)(F)F)C(F)(F)F)cc1] | 522.1 | 2.15 | C |
| 54 | 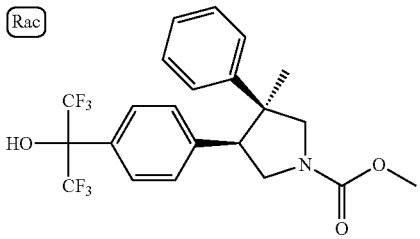 [SMILES: COC(=O)N1C[C@@H](c2ccc(C(O)(C(F)(F)F)C(F)(F)F)cc2)[C@@](C)(c2ccccc2)C1] | 461.9 | 2.05 | C |

TABLE 4-continued

| Example number | Structure | MS observed (M + 1) | HPLC ret. time (min.) | HPLC method |
|---|---|---|---|---|
| 55 | 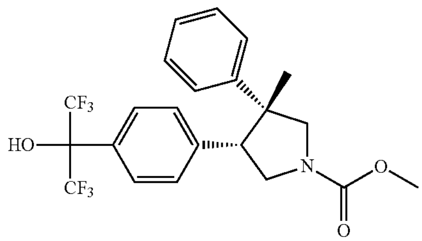 [SMILES: COC(=O)N1C[C@H](c2ccc(C(O)(C(F)(F)F)C(F)(F)F)cc2)[C@](C)(c2ccccc2)C1] | 461.8 | 2.00 | C |
| 56 | Rac | 475.9 | 2.17 | C |
| 57 | 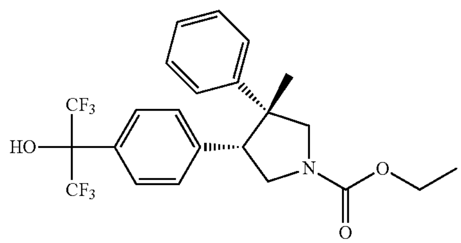 [SMILES: CCOC(=O)N1C[C@H](c2ccc(C(O)(C(F)(F)F)C(F)(F)F)cc2)[C@](C)(c2ccccc2)C1] | 475.8 | 2.12 | C |
| 58 | 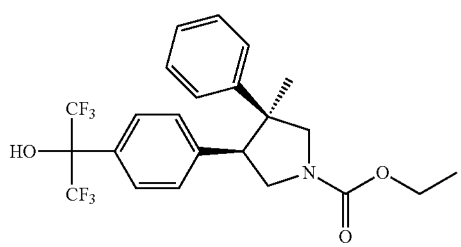 [SMILES: CCOC(=O)N1C[C@@H](c2ccc(C(O)(C(F)(F)F)C(F)(F)F)cc2)[C@@](C)(c2ccccc2)C1] | 476.2 | 2.27 | C |
| 59 | Rac | 490.1 | 2.31 | C |
| 60 | 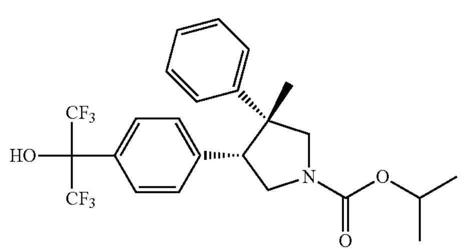 [SMILES: CC(C)OC(=O)N1C[C@H](c2ccc(C(O)(C(F)(F)F)C(F)(F)F)cc2)[C@](C)(c2ccccc2)C1] | 490.1 | 2.38 | C |

TABLE 4-continued

| Example number | Structure | MS observed (M + 1) | HPLC ret. time (min.) | HPLC method |
|---|---|---|---|---|
| 61 | 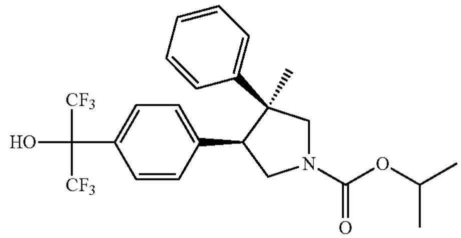 [SMILES: CC(C)OC(=O)N1C[C@@H](c2ccc(C(O)(C(F)(F)F)C(F)(F)F)cc2)[C@@](C)(c2ccccc2)C1] | 490.1 | 2.38 | C |
| 62 | Rac | 524.1 | 2.36 | C |
| 63 | Rac | 538.1 | 2.40 | C |
| 64 | 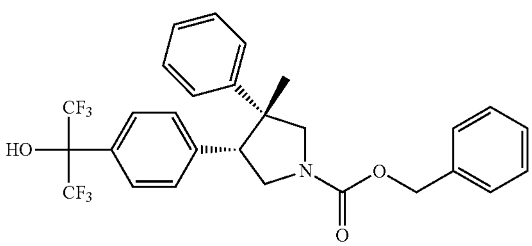 [SMILES: C[C@@]1(c2ccccc2)CN(C(=O)OCc2ccccc2)C[C@@H]1c1ccc(C(O)(C(F)(F)F)C(F)(F)F)cc1] | 538.2 | 2.45 | C |
| 65 | 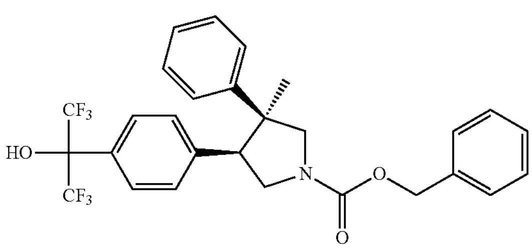 [SMILES: C[C@]1(c2ccccc2)CN(C(=O)OCc2ccccc2)C[C@H]1c1ccc(C(O)(C(F)(F)F)C(F)(F)F)cc1] | 538.2 | 2.45 | C |
| 66 | Rac | 475.2 | 1.84 | C |

TABLE 4-continued
| Example number | Structure | MS observed (M + 1) | HPLC ret. time (min.) | HPLC method |
|---|---|---|---|---|
| 67 | 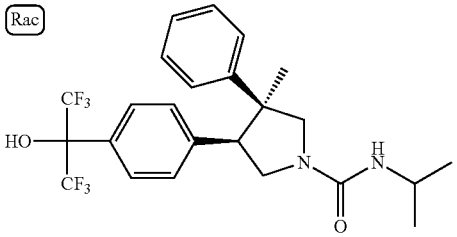 [SMILES: CC(C)NC(=O)N1C[C@@H](c2ccc(C(O)(C(F)(F)F)C(F)(F)F)cc2)[C@@](C)(c2ccccc2)C1] | 489.1 | 1.97 | C |
| 68 | 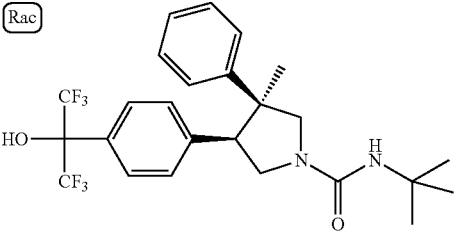 | 503.2 | 2.14 | C |
| 69 | 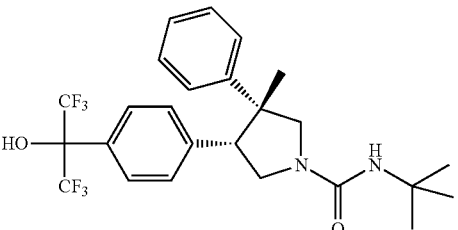 | 502.8 | 2.05 | C |
| 70 | 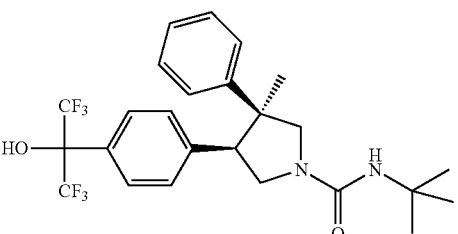 | 503.2 | 2.20 | C |
| 71 | 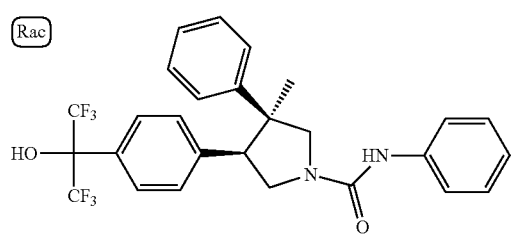 [SMILES: C[C@]1(c2ccccc2)CN(C(=O)Nc2ccccc2)C[C@H]1c1ccc(C(O)(C(F)(F)F)C(F)(F)F)cc1] | 523.1 | 2.11 | C |
| 72 | 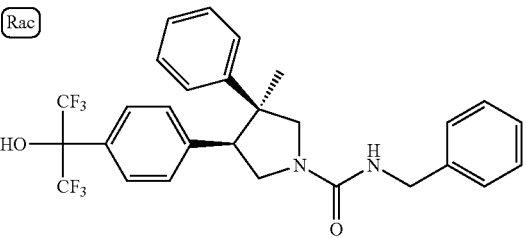 [SMILES: C[C@]1(c2ccccc2)CN(C(=O)NCc2ccccc2)C[C@H]1c1ccc(C(O)(C(F)(F)F)C(F)(F)F)cc1] | 537.1 | 2.08 | C |

TABLE 4-continued

| Example number | Structure | MS observed (M + 1) | HPLC ret. time (min.) | HPLC method |
|---|---|---|---|---|
| 73 | 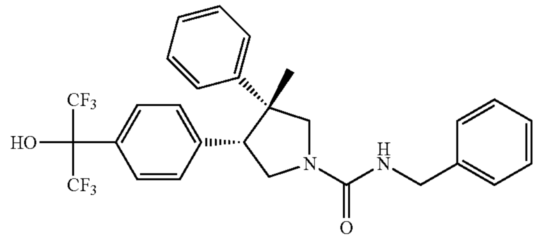 [SMILES: C[C@@]1(c2ccccc2)CN(C(=O)NCc2ccccc2)C[C@@H]1c1ccc(C(O)(C(F)(F)F)C(F)(F)F)cc1] | 536.8 | 1.99 | C |
| 74 | 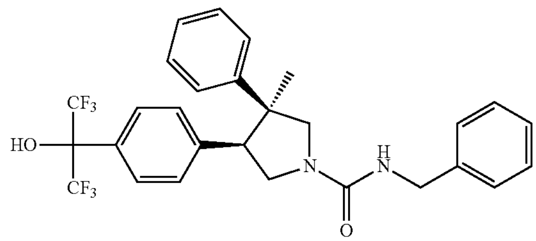 [SMILES: C[C@]1(c2ccccc2)CN(C(=O)NCc2ccccc2)C[C@H]1c1ccc(C(O)(C(F)(F)F)C(F)(F)F)cc1] | 537.2 | 2.14 | C |
| 75 | 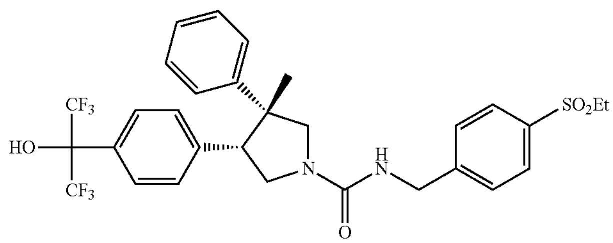 | 629.0 | 1.84 | C |
| 76 | 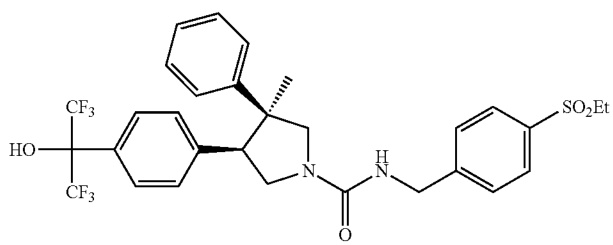 | 629.2 | 1.98 | C |
| 77 | 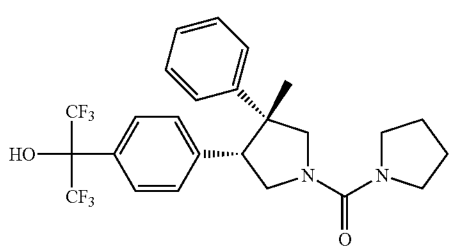 [SMILES: C[C@@]1(c2ccccc2)CN(C(=O)N2CCCC2)C[C@@H]1c1ccc(C(O)(C(F)(F)F)C(F)(F)F)cc1] | 501.1 | 2.03 | C |
| 78 | 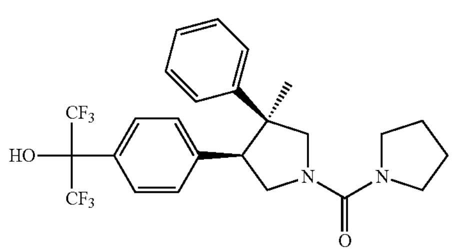 [SMILES: C[C@]1(c2ccccc2)CN(C(=O)N2CCCC2)C[C@H]1c1ccc(C(O)(C(F)(F)F)C(F)(F)F)cc1] | 501.2 | 2.16 | C |

TABLE 4-continued

| Example number | Structure | MS observed (M + 1) | HPLC ret. time (min.) | HPLC method |
|---|---|---|---|---|
| 79 | 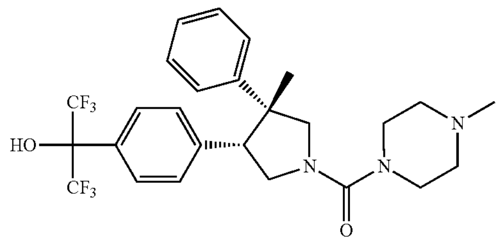 [SMILES: CN1CCN(C(=O)N2C[C@H](c3ccc(C(O)(C(F)(F)F)C(F)(F)F)cc3)[C@](C)(c3ccccc3)C2)CC1] | 530.2 | 1.70 | C |
| 80 | 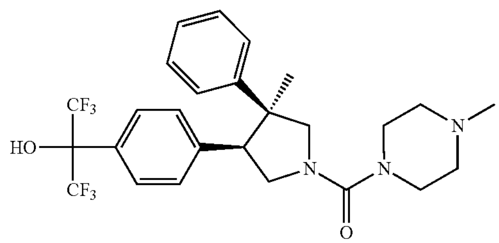 [SMILES: CN1CCN(C(=O)N2C[C@@H](c3ccc(C(O)(C(F)(F)F)C(F)(F)F)cc3)[C@@](C)(c3ccccc3)C2)CC1] | 530.2 | 1.80 | C |
| 81 | 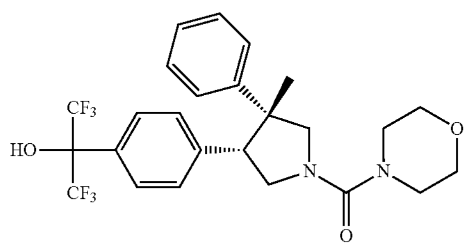 [SMILES: C[C@@]1(c2ccccc2)CN(C(=O)N2CCOCC2)C[C@@H]1c1ccc(C(O)(C(F)(F)F)C(F)(F)F)cc1] | 517.1 | 1.86 | C |
| 82 | 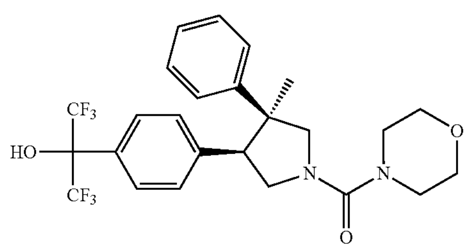 [SMILES: C[C@]1(c2ccccc2)CN(C(=O)N2CCOCC2)C[C@H]1c1ccc(C(O)(C(F)(F)F)C(F)(F)F)cc1] | 517.2 | 2.00 | C |
| 83 | Rac | 482.1 | 1.97 | C |
| 84 | Rac | 544.1 | 2.27 | C |

TABLE 4-continued

| Example number | Structure | MS observed (M + 1) | HPLC ret. time (min.) | HPLC method |
|---|---|---|---|---|
| 85 | 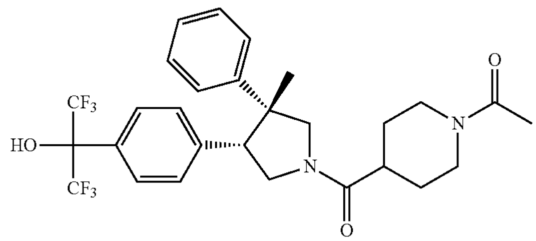 [SMILES: CC(=O)N1CCC(C(=O)N2C[C@H](c3ccc(C(O)(C(F)(F)F)C(F)(F)F)cc3)[C@](C)(c3ccccc3)C2)CC1] | 557.2 | 1.81 | C |
| 86 | 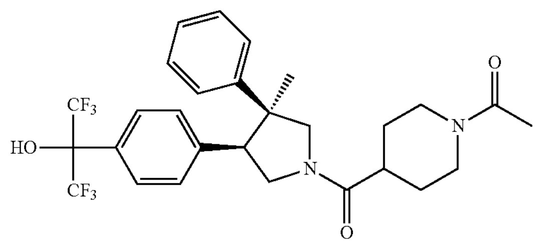 [SMILES: CC(=O)N1CCC(C(=O)N2C[C@@H](c3ccc(C(O)(C(F)(F)F)C(F)(F)F)cc3)[C@@](C)(c3ccccc3)C2)CC1] | 557.2 | 1.86 | C |
| 87 | (Rac) | 508.1 | 2.14 | C |
| 88 | 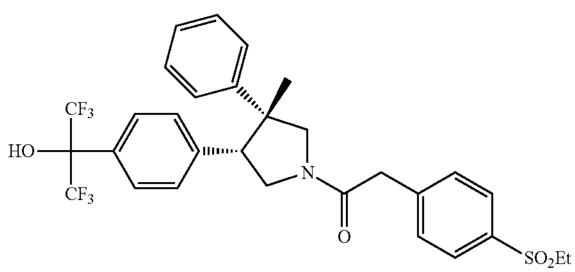 | 614.1 | 1.90 | C |
| 89 | 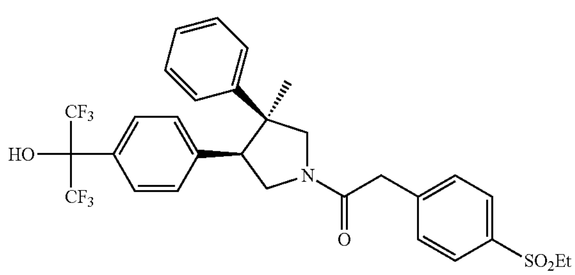 | 614.2 | 2.04 | C |
| 90 | (Rac) | 632.1 | 1.99 | C |

TABLE 4-continued

| Example number | Structure | MS observed (M + 1) | HPLC ret. time (min.) | HPLC method |
|---|---|---|---|---|
| 91 | 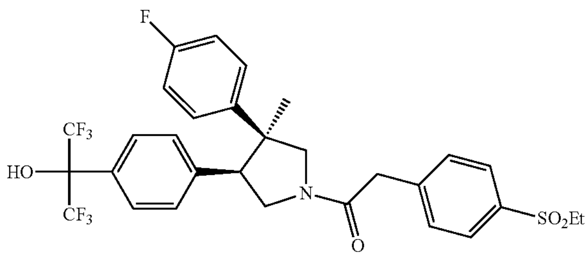 | 632.2 | 2.04 | C |
| 92 | 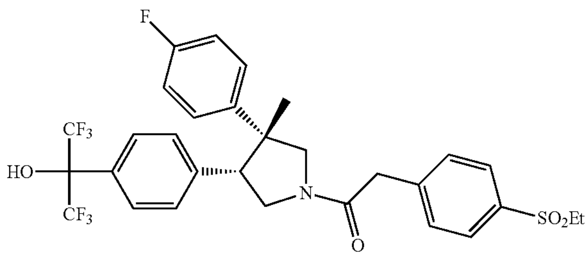 | 632.2 | 2.04 | C |
| 93 | 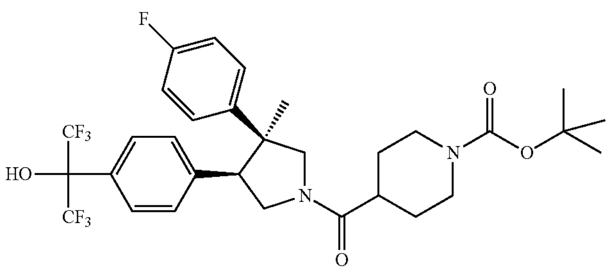 [SMILES: CC(C)(C)OC(=O)N1CCC(C(=O)N2C[C@@H](c3ccc(C(O)(C(F)(F)F)C(F)(F)F)cc3)[C@@](C)(c3ccc(F)cc3)C2)CC1] | 632.8 | 2.17 | C |
| 94 | 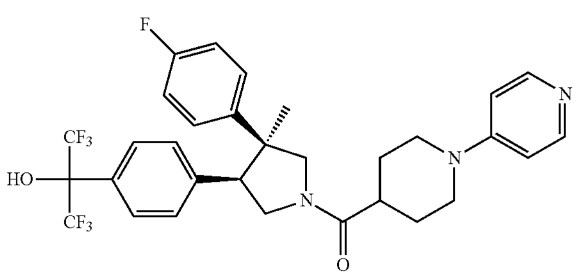 [SMILES: C[C@]1(c2ccc(F)cc2)CN(C(=O)C2CCN(c3ccncc3)CC2)C[C@H]1c1ccc(C(O)(C(F)(F)F)C(F)(F)F)cc1] | 610.2 | 1.65 | C |
| 95 | 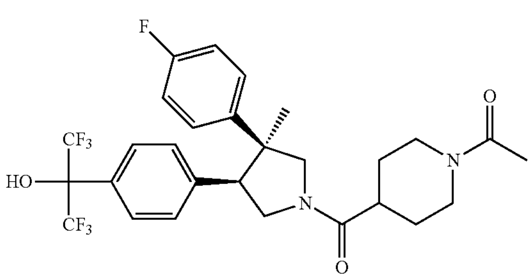 [SMILES: CC(=O)N1CCC(C(=O)N2C[C@@H](c3ccc(C(O)(C(F)(F)F)C(F)(F)F)cc3)[C@@](C)(c3ccc(F)cc3)C2)CC1] | 575.2 | 1.87 | C |

TABLE 4-continued

| Example number | Structure | MS observed (M + 1) | HPLC ret. time (min.) | HPLC method |
|---|---|---|---|---|
| 96 | 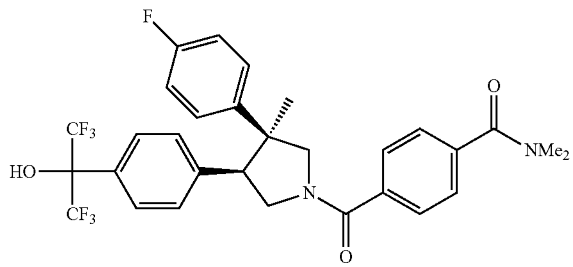 [SMILES: CN(C)C(=O)c1ccc(C(=O)N2C[C@@H](c3ccc(C(O)(C(F)(F)F)C(F)(F)F)cc3)[C@@](C)(c3ccc(F)cc3)C2)cc1] | 596.8 | 1.80 | C |
| 97 | 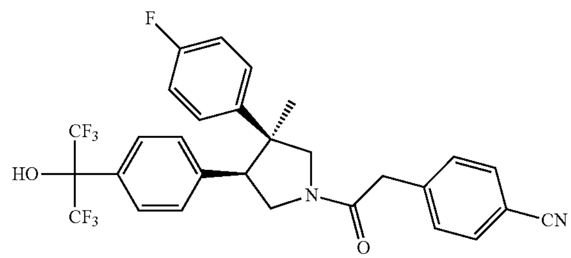 [SMILES: C[C@]1(c2ccc(F)cc2)CN(C(=O)Cc2ccc(C#N)cc2)C[C@H]1c1ccc(C(O)(C(F)(F)F)C(F)(F)F)cc1] | 564.8 | 1.98 | C |
| 98 | 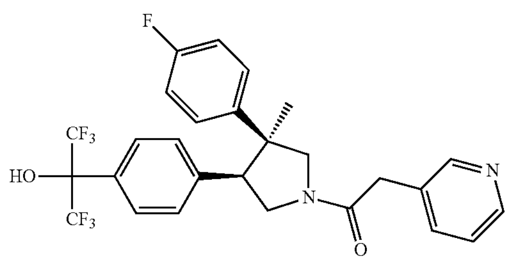 [SMILES: C[C@]1(c2ccc(F)cc2)CN(C(=O)Cc2cccnc2)C[C@H]1c1ccc(C(O)(C(F)(F)F)C(F)(F)F)cc1] | 540.8 | 1.51 | C |
| 99 | 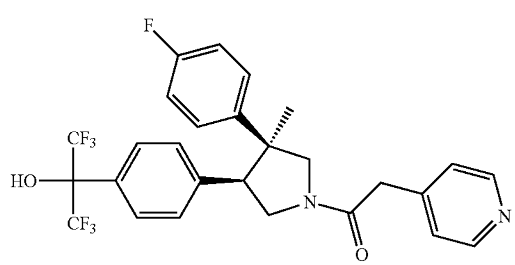 [SMILES: C[C@]1(c2ccc(F)cc2)CN(C(=O)Cc2ccncc2)C[C@H]1c1ccc(C(O)(C(F)(F)F)C(F)(F)F)cc1] | 541.1 | 1.67 | C |
| 100 | 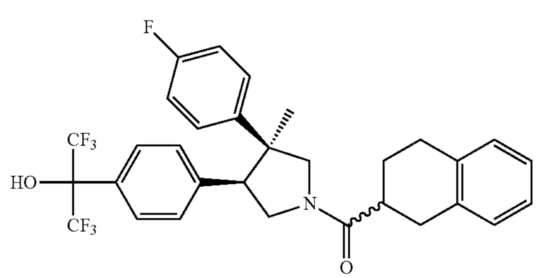 [SMILES: C[C@]1(c2ccc(F)cc2)CN(C(=O)C2CCc3ccccc3C2)C[C@H]1c1ccc(C(O)(C(F)(F)F)C(F)(F)F)cc1] | 579.8 | 2.27 | C |

TABLE 4-continued

| Example number | Structure | MS observed (M + 1) | HPLC ret. time (min.) | HPLC method |
|---|---|---|---|---|
| 101 | [Rac] | 521.2 | 2.15 | C |
| 102 | 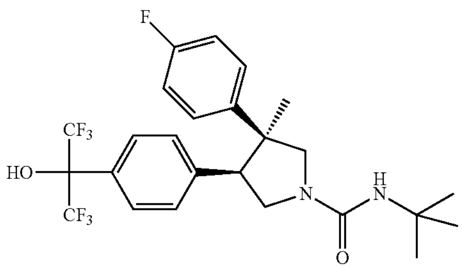 [SMILES: CC(C)(C)NC(=O)N1C[C@@H](c2ccc(C(O)(C(F)(F)F)C(F)(F)F)cc2)[C@@](C)(c2ccc(F)cc2)C1] | 521.1 | 2.24 | C |
| 103 | [Rac] | 555.2 | 2.09 | C |
| 104 | 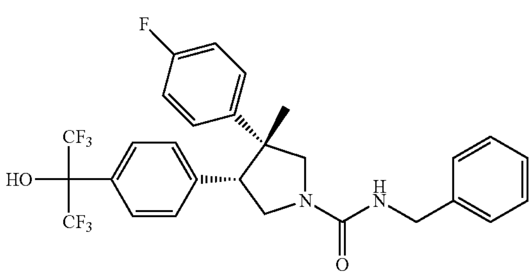 [SMILES: C[C@@]1(c2ccc(F)cc2)CN(C(=O)NCc2ccccc2)C[C@@H]1c1ccc(C(O)(C(F)(F)F)C(F)(F)F)cc1] | 555.1 | 2.14 | C |
| 105 | 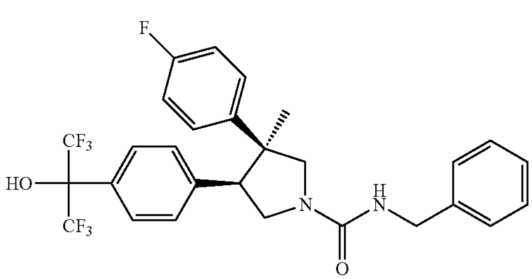 [SMILES: C[C@]1(c2ccc(F)cc2)CN(C(=O)NCc2ccccc2)C[C@H]1c1ccc(C(O)(C(F)(F)F)C(F)(F)F)cc1] | 555.1 | 2.14 | C |

TABLE 4-continued
| Example number | Structure | MS observed (M + 1) | HPLC ret. time (min.) | HPLC method |
|---|---|---|---|---|
| 106 | 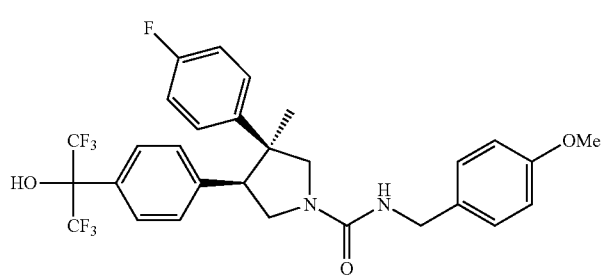 [SMILES: COc1ccc(CNC(=O)N2C[C@@H](c3ccc(C(O)(C(F)(F)F)C(F)(F)F)cc3)[C@@](C)(c3ccc(F)cc3)C2)cc1] | 584.7 | 1.98 | C |
| 107 | 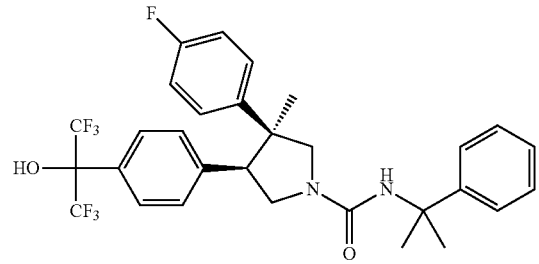 [SMILES: CC(C)(NC(=O)N1C[C@@H](c2ccc(C(O)(C(F)(F)F)C(F)(F)F)cc2)[C@@](C)(c2ccc(F)cc2)C1)c1ccccc1] | 583.2 | 2.34 | C |
| 108 | 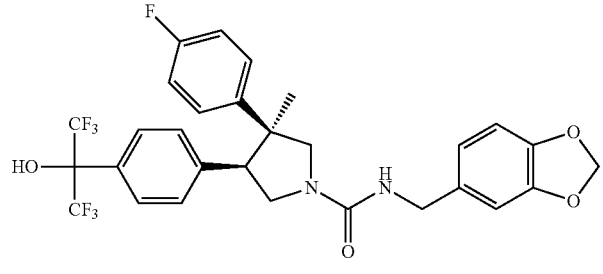 [SMILES: C[C@]1(c2ccc(F)cc2)CN(C(=O)NCc2ccc3c(c2)OCO3)C[C@H]1c1ccc(C(O)(C(F)(F)F)C(F)(F)F)cc1] | 598.7 | 1.97 | C |
| 109 | 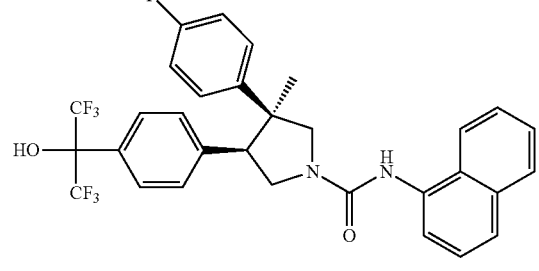 | 591.2 | 2.21 | C |
| 110 | 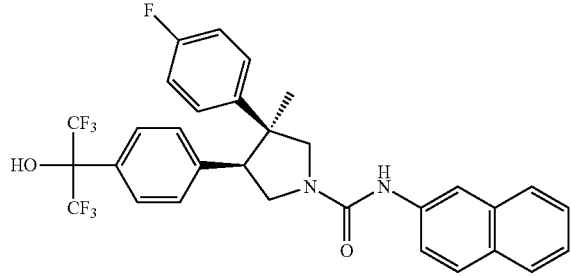 [SMILES: C[C@]1(c2ccc(F)cc2)CN(C(=O)Nc2ccc3ccccc3c2)C[C@H]1c1ccc(C(O)(C(F)(F)F)C(F)(F)F)cc1] | 591.2 | 2.37 | C |

TABLE 4-continued

| Example number | Structure | MS observed (M + 1) | HPLC ret. time (min.) | HPLC method |
|---|---|---|---|---|
| 111 | 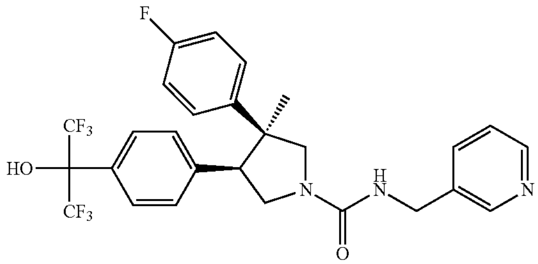 [SMILES: C[C@]1(c2ccc(F)cc2)CN(C(=O)NCc2cccnc2)C[C@H]1c1ccc(C(O)(C(F)(F)F)C(F)(F)F)cc1] | 556.2 | 1.87 | C |
| 112 | 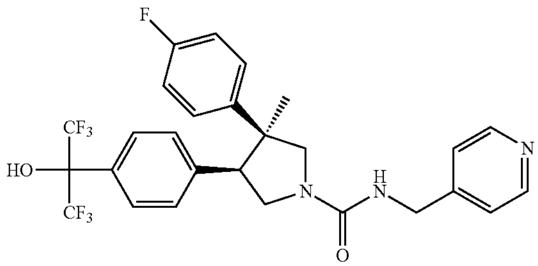 [SMILES: C[C@]1(c2ccc(F)cc2)CN(C(=O)NCc2ccncc2)C[C@H]1c1ccc(C(O)(C(F)(F)F)C(F)(F)F)cc1] | 556.1 | 1.86 | C |
| 113 | 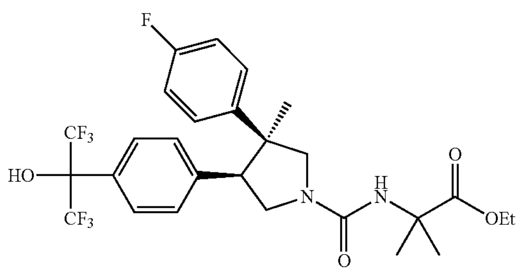 [SMILES: CCOC(=O)C(C)(C)NC(=O)N1C[C@@H](c2ccc(C(O)(C(F)(F)F)C(F)(F)F)cc2)[C@@](C)(c2ccc(F)cc2)C1] | 579.2 | 2.08 | C |
| 114 | 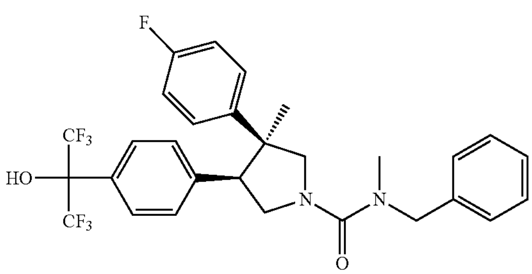 [SMILES: CN(Cc1ccccc1)C(=O)N1C[C@@H](c2ccc(C(O)(C(F)(F)F)C(F)(F)F)cc2)[C@@](C)(c2ccc(F)cc2)C1] | 569.2 | 2.36 | C |
| 115 | 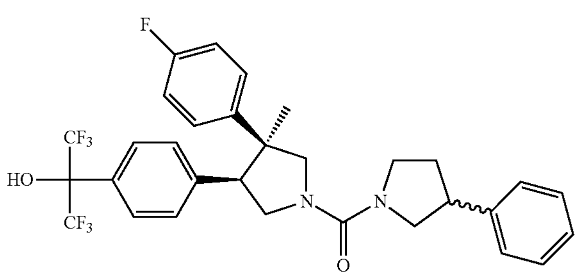 [SMILES: C[C@]1(c2ccc(F)cc2)CN(C(=O)N2CCC(c3ccccc3)C2)C[C@H]1c1ccc(C(O)(C(F)(F)F)C(F)(F)F)cc1] | 595.2 | 2.42 | C |

TABLE 4-continued

| Example number | Structure | MS observed (M + 1) | HPLC ret. time (min.) | HPLC method |
|---|---|---|---|---|
| 116 | 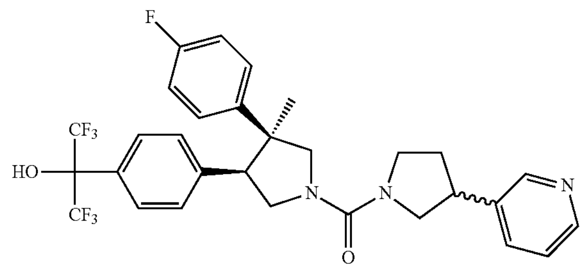 [SMILES: C[C@]1(c2ccc(F)cc2)CN(C(=O)N2CCC(c3cccnc3)C2)C[C@H]1c1ccc(C(O)(C(F)(F)F)C(F)(F)F)cc1] | 596.2 | 1.89 | C |
| 117 | 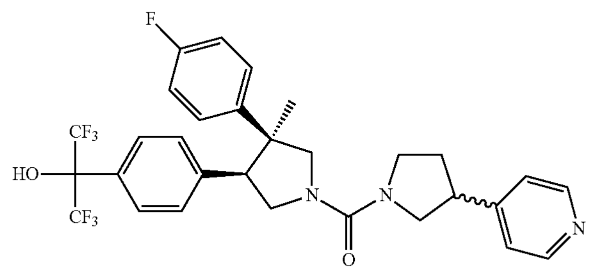 [SMILES: C[C@]1(c2ccc(F)cc2)CN(C(=O)N2CCC(c3ccncc3)C2)C[C@H]1c1ccc(C(O)(C(F)(F)F)C(F)(F)F)cc1] | 596.2 | 1.88 | C |
| 118 | 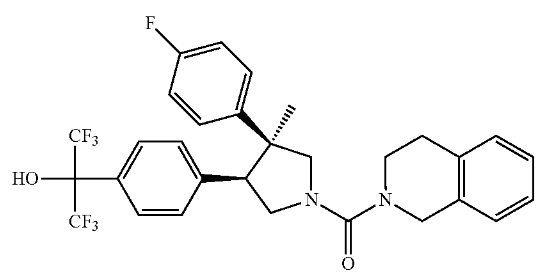 [SMILES: C[C@]1(c2ccc(F)cc2)CN(C(=O)N2CCc3ccccc3C2)C[C@H]1c1ccc(C(O)(C(F)(F)F)C(F)(F)F)cc1] | 580.8 | 2.25 | C |
| 119 | 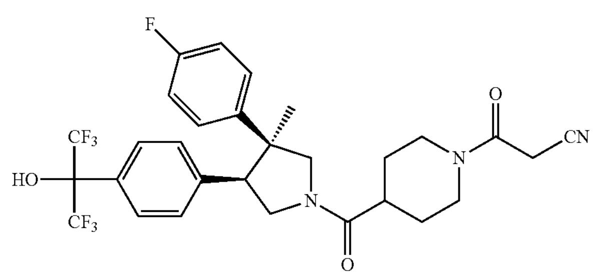 [SMILES: C[C@]1(c2ccc(F)cc2)CN(C(=O)C2CCN(C(=O)CC#N)CC2)C[C@H]1c1ccc(C(O)(C(F)(F)F)C(F)(F)F)cc1] | 600.2 | 1.91 | C |
| 120 | 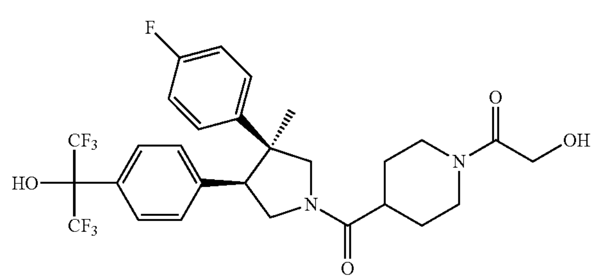 | 591.2 | 1.75 | C |

TABLE 4-continued

| Example number | Structure | MS observed (M + 1) | HPLC ret. time (min.) | HPLC method |
|---|---|---|---|---|
| 121 | 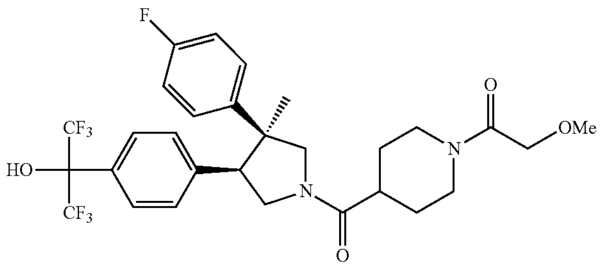 [SMILES: COCC(=O)N1CCC(C(=O)N2C[C@@H](c3ccc(C(O)(C(F)(F)F)C(F)(F)F)cc3)[C@@](C)(c3ccc(F)cc3)C2)CC1] | 605.1 | 1.81 | C |
| 122 | 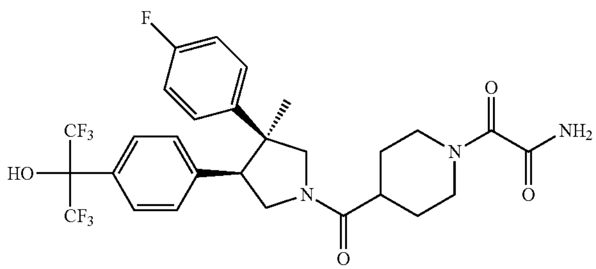 [SMILES: C[C@]1(c2ccc(F)cc2)CN(C(=O)C2CCN(C(=O)C(N)=O)CC2)C[C@H]1c1ccc(C(O)(C(F)(F)F)C(F)(F)F)cc1] | 604.2 | 1.77 | C |
| 123 | 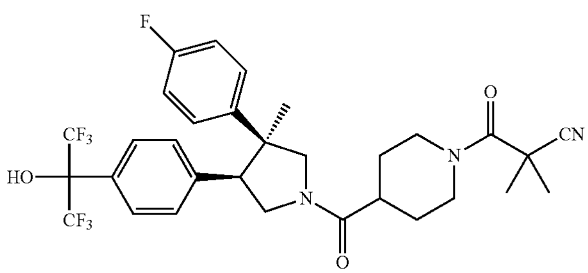 [SMILES: CC(C)(C#N)C(=O)N1CCC(C(=O)N2C[C@@H](c3ccc(C(O)(C(F)(F)F)C(F)(F)F)cc3)[C@@](C)(c3ccc(F)cc3)C2)CC1] | 628.2 | 2.09 | C |
| 124 | 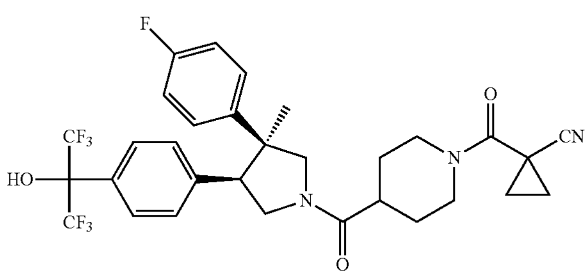 [SMILES: C[C@]1(c2ccc(F)cc2)CN(C(=O)C2CCN(C(=O)C3(C#N)CC3)CC2)C[C@H]1c1ccc(C(O)(C(F)(F)F)C(F)(F)F)cc1] | 626.2 | 1.95 | C |
| 125 | 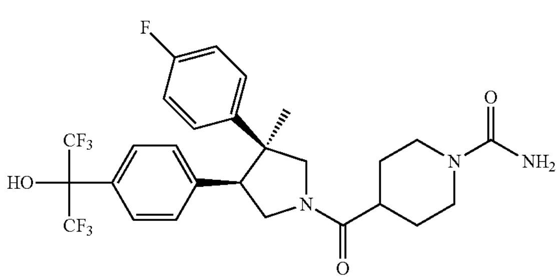 [SMILES: C[C@]1(c2ccc(F)cc2)CN(C(=O)C2CCN(C(N)=O)CC2)C[C@H]1c1ccc(C(O)(C(F)(F)F)C(F)(F)F)cc1] | 575.7 | 1.63 | C |

TABLE 4-continued

| Example number | Structure | MS observed (M + 1) | HPLC ret. time (min.) | HPLC method |
|---|---|---|---|---|
| 126 | 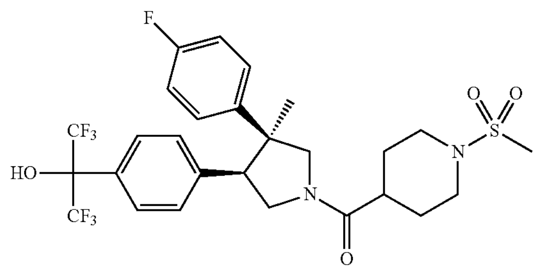 [SMILES: C[C@]1(c2ccc(F)cc2)CN(C(=O)C2CCN(S(C)(=O)=O)CC2)C[C@H]1c1ccc(C(O)(C(F)(F)F)C(F)(F)F)cc1] | 611.1 | 1.95 | C |
| 127 | 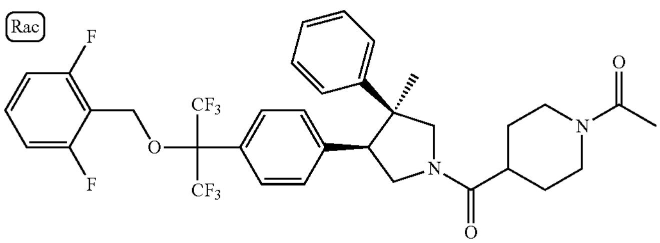 [SMILES: CC(=O)N1CCC(C(=O)N2C[C@@H](c3ccc(C(OCc4c(F)cccc4F)(C(F)(F)F)C(F)(F)F)cc3)[C@@](C)(c3ccccc3)C2)CC1] | 683.3 | 2.35 | C |
| 128 | 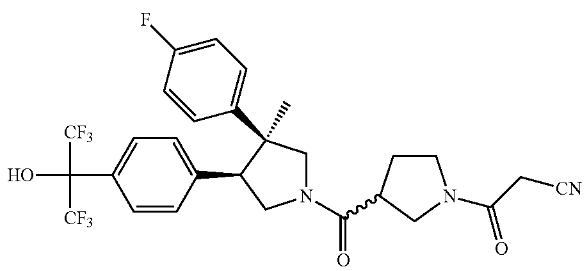 [SMILES: C[C@]1(c2ccc(F)cc2)CN(C(=O)C2CCN(C(=O)CC#N)C2)C[C@H]1c1ccc(C(O)(C(F)(F)F)C(F)(F)F)cc1] | 586.2 | 1.89 | C |
| 129 | 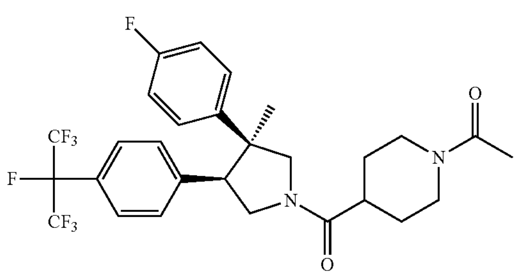 [SMILES: CC(=O)N1CCC(C(=O)N2C[C@@H](c3ccc(C(F)(C(F)(F)F)C(F)(F)F)cc3)[C@@](C)(c3ccc(F)cc3)C2)CC1] | 577.3 | 2.13 | C |
| 130 | 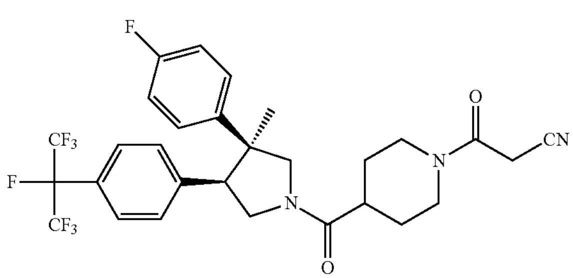 [SMILES: C[C@]1(c2ccc(F)cc2)CN(C(=O)C2CCN(C(=O)CC#N)CC2)C[C@H]1c1ccc(C(F)(C(F)(F)F)C(F)(F)F)cc1] | 602.3 | 2.16 | C |

TABLE 4-continued

| Example number | Structure | MS observed (M + 1) | HPLC ret. time (min.) | HPLC method |
|---|---|---|---|---|
| 131 | 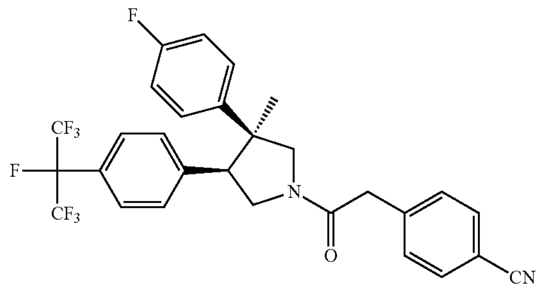 [SMILES: C[C@]1(c2ccc(F)cc2)CN(C(=O)Cc2ccc(C#N)cc2)C[C@H]1c1ccc(C(F)(C(F)(F)F)C(F)(F)F)cc1] | 567.2 | 2.38 | C |
| 132 | 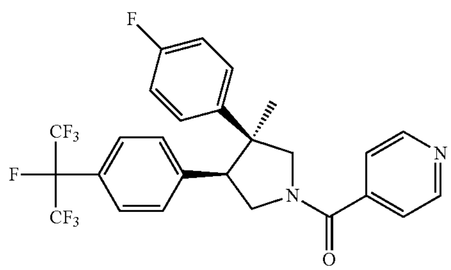 [SMILES: C[C@]1(c2ccc(F)cc2)CN(C(=O)c2ccncc2)C[C@H]1c1ccc(C(F)(C(F)(F)F)C(F)(F)F)cc1] | 529.2 | 2.20 | C |
| 133 | 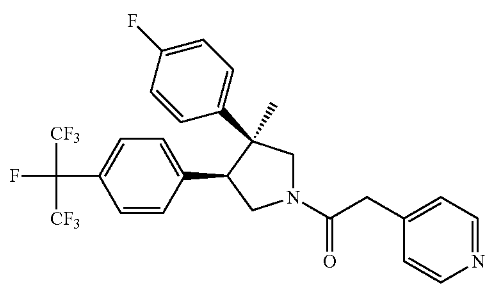 [SMILES: C[C@]1(c2ccc(F)cc2)CN(C(=O)Cc2ccncc2)C[C@H]1c1ccc(C(F)(C(F)(F)F)C(F)(F)F)cc1] | 543.2 | 2.17 | C |
| 134 | 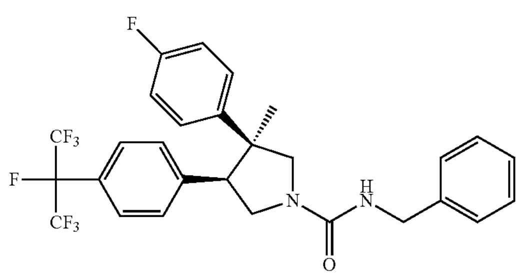 [SMILES: C[C@]1(c2ccc(F)cc2)CN(C(=O)NCc2ccccc2)C[C@H]1c1ccc(C(F)(C(F)(F)F)C(F)(F)F)cc1] | 557.2 | 2.40 | C |
| 135 | 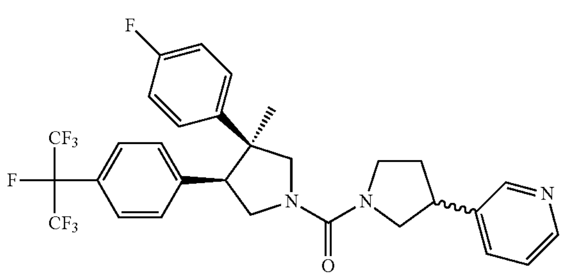 [SMILES: C[C@]1(c2ccc(F)cc2)CN(C(=O)N2CCC(c3cccnc3)C2)C[C@H]1c1ccc(C(F)(C(F)(F)F)C(F)(F)F)cc1] | 598.3 | 2.28 | C |

TABLE 4-continued

| Example number | Structure | MS observed (M + 1) | HPLC ret. time (min.) | HPLC method |
|---|---|---|---|---|
| 136 | isomer 1 | 598.3 | 2.25 | C |
| 137 | isomer 2 | 598.3 | 2.28 | C |
| 138 | Rac | 600.1 | 1.84 | C |
| 139 | Rac | 543.1 | 1.65 | C |
| 140 | Rac | 489.1 | 1.99 | C |

TABLE 4-continued

| Example number | Structure | MS observed (M + 1) | HPLC ret. time (min.) | HPLC method |
|---|---|---|---|---|
| 141 | Rac | 523.1 | 1.94 | C |
| 142 | Rac | 557.2 | 1.73 | C |
| 143 | Rac | 503.2 | 2.18 | C |
| 144 | Rac | 537.2 | 2.00 | C |
| 145 | Rac | 571.2 | 1.78 | C |
| 146 | Rac | 517.2 | 2.14 | C |

TABLE 4-continued
| Example number | Structure | MS observed (M + 1) | HPLC ret. time (min.) | HPLC method |
|---|---|---|---|---|
| 147 | 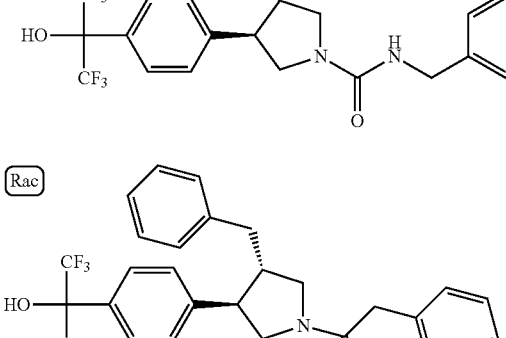 | 551.2 | 2.08 | C |
| 148 | 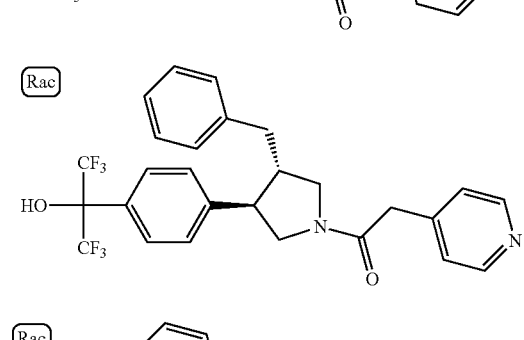 | 547.3 | 2.11 | C |
| 149 | 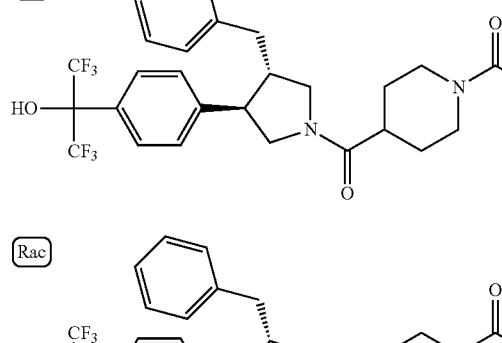 | 523.3 | 1.90 | C |
| 150 | 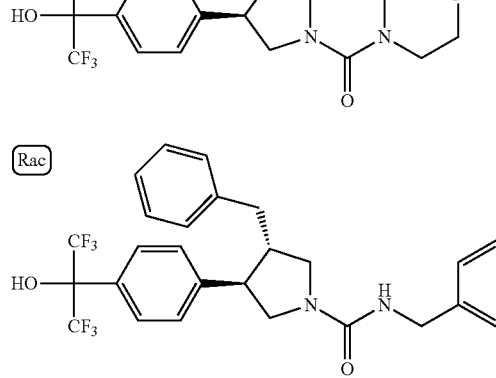 | 557.3 | 1.86 | C |
| 151 | 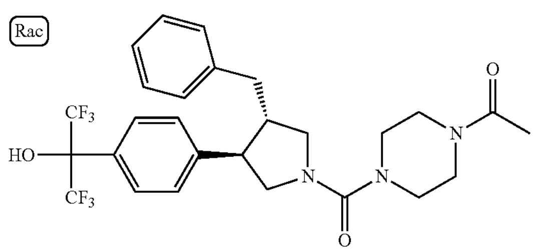 [SMILES: CC(=O)N1CCC(C(=O)N2C[C@@H](Cc3ccccc3)[C@H](c3ccc(C(O)(C(F)(F)F)C(F)(F)F)cc3)C2)CC1] | 558.3 | 1.86 | C |
| 152 | 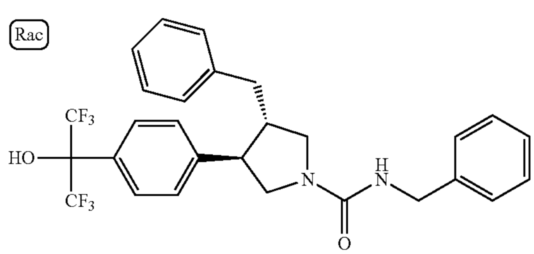 [SMILES: O=C(NCc1ccccc1)N1C[C@@H](Cc2ccccc2)[C@H](c2ccc(C(O)(C(F)(F)F)C(F)(F)F)cc2)C1] | 537.3 | 2.15 | C |

TABLE 4-continued
| Example number | Structure | MS observed (M + 1) | HPLC ret. time (min.) | HPLC method |
|---|---|---|---|---|
| 153 | 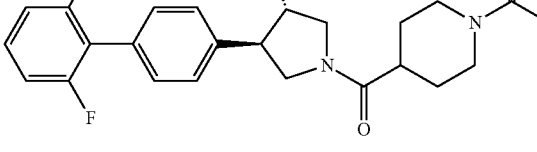 | 503.4 | 2.11 | C |
| 154 | 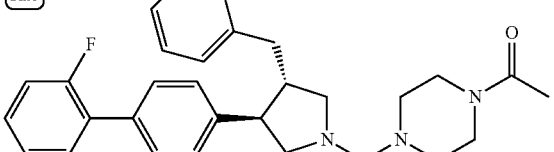 | 504.4 | 2.11 | C |
| 155 | 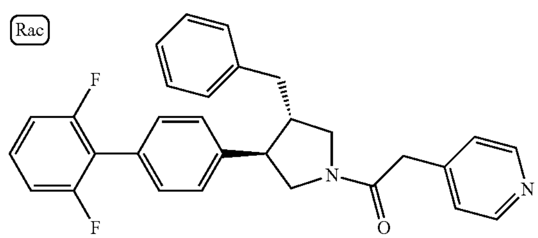 [SMILES: O=C(Cc1ccncc1)N1C[C@@H](Cc2ccccc2)[C@H](c2ccc(-c3c(F)cccc3F)cc2)C1] | 469.4 | 2.15 | C |
| 156 | 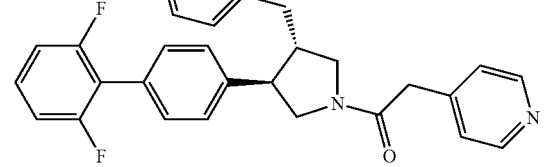 | 493.4 | 2.38 | C |
| 157 | 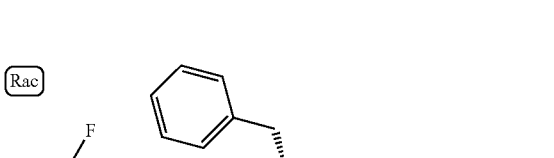 | 611.1 | 2.06 | C |

TABLE 4-continued
| Example number | Structure | MS observed (M + 1) | HPLC ret. time (min.) | HPLC method |
|---|---|---|---|---|
| 158 | 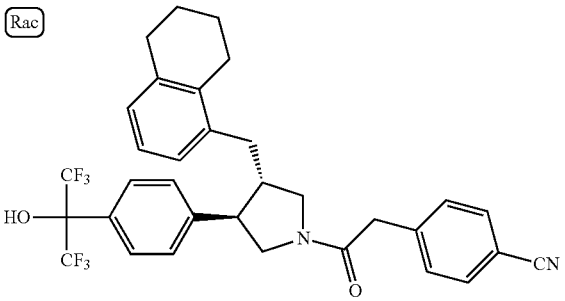 [SMILES: N#Cc1ccc(CC(=O)N2C[C@@H](Cc3cccc4c3CCCC4)[C@H](c3ccc(C(O)(C(F)(F)F)C(F)(F)F)cc3)C2)cc1] | 601.3 | 2.41 | C |
| 159 | 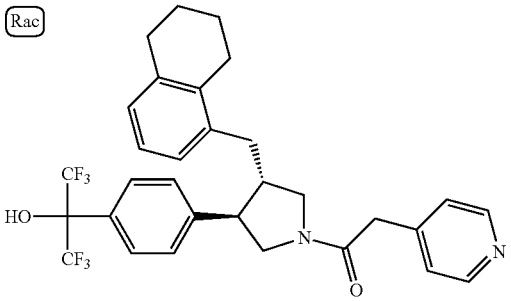 [SMILES: O=C(Cc1ccncc1)N1C[C@@H](Cc2cccc3c2CCCC3)[C@H](c2ccc(C(O)(C(F)(F)F)C(F)(F)F)cc2)C1] | 577.1 | 2.11 | C |
| 160 | 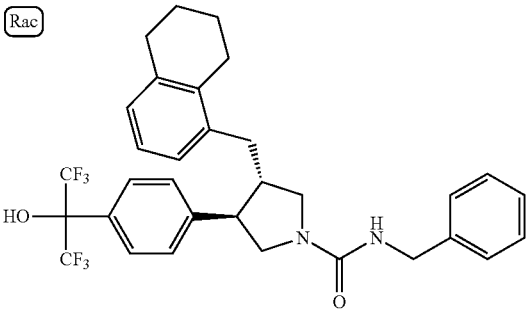 [SMILES: O=C(NCc1ccccc1)N1C[C@@H](Cc2cccc3c2CCCC3)[C@H](c2ccc(C(O)(C(F)(F)F)C(F)(F)F)cc2)C1] | 591.1 | 2.36 | C |
| 161 | 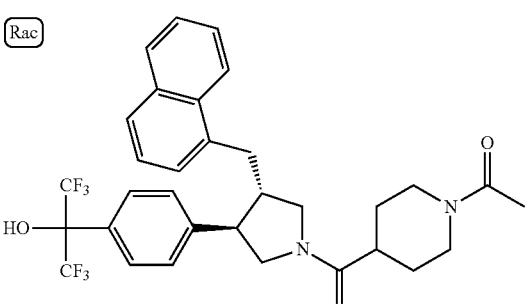 | 607.3 | 2.02 | C |
| 162 | 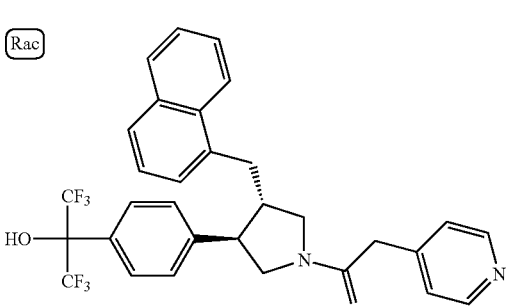 | 573.2 | 1.96 | C |

TABLE 4-continued

| Example number | Structure | MS observed (M + 1) | HPLC ret. time (min.) | HPLC method |
|---|---|---|---|---|
| 163 | Rac | 587.2 | 2.32 | C |
| 164 | enant 1 | 554.2 | 15.15 | A |
| 165 | enant 2 | 554.2 | 15.16 | A |
| 166 | enant 1 | 519.2 | 8.80 | A |

Example 167

4-(2-((3S,4S)-3-(4-fluorophenyl)-4-(4-(1,1,1,3,3,3-hexafluoro-2-hydroxypropan-2-yl)phenyl)-3-methylpyrrolidin-1-yl)-2-oxoethyl)benzamide

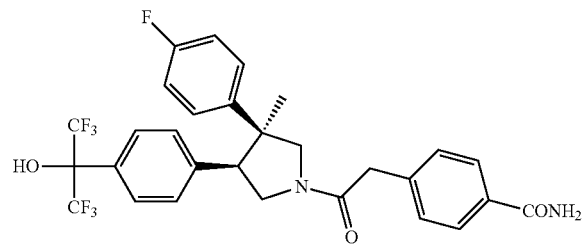 [SMILES: C[C@]1(c2ccc(F)cc2)CN(C(=O)Cc2ccc(C(N)=O)cc2)C[C@H]1c1ccc(C(O)(C(F)(F)F)C(F)(F)F)cc1]

Hydrogen peroxide (0.1 mL, 0.979 mmol, 30 wt %) was added to a methanol (0.15 mL) solution of 4-(2-((3S,4S)-3-(4-fluorophenyl)-4-(4-(1,1,1,3,3,3-hexafluoro-2-hydroxypropan-2-yl)phenyl)-3-methylpyrrolidin-1-yl)-2-oxoethyl)benzonitrile (6 mg, 10.63 μmol, from Example 97) and 1 M NaOH (0.1 mL, 0.100 mmol). The mixture was stirred at room temperature for 45 min. The crude was diluted with methanol (1 mL) and purified by preparative HPLC (Waters XBridge C18, 19×150 mm, 5-μm particles; Mobile Phase A: 5:95 acetonitrile:water with 10-mM ammonium acetate; Mobile Phase B: 95:5 acetonitrile:water with 10-mM ammonium acetate. Flow: 20 mL/min) to give the title compound (6.4 mg, 100% yield). MS (ES): m/z=583.1 [M+1]; LC retention time: 1.86 min (analytical HPLC Method C); $^1$H NMR (500 MHz, 1:1 mixture of CDCl$_3$-CD3OD) δ 7.87 (dd, J=15.5, 8.3 Hz, 2H), 7.50-7.38 (m, 4H), 6.74-6.66 (m, 4H), 6.63-6.60 (m, 1H), 6.55-6.52 (m, 1H), 4.32-4.15 (m, 2H), 4.03-3.92 (m, 1H), 3.91-3.81 (m, 2H), 3.69-3.55 (m, 2H), 3.52-3.38 (m, 1H), 1.49 (s, 3H).

Examples 168 & 169

1-(4-((3 S4R)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone & 1-(4-((3R,4S)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone

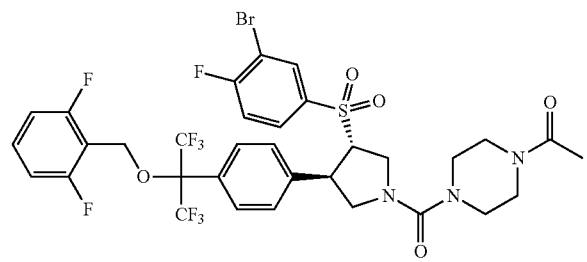

-continued

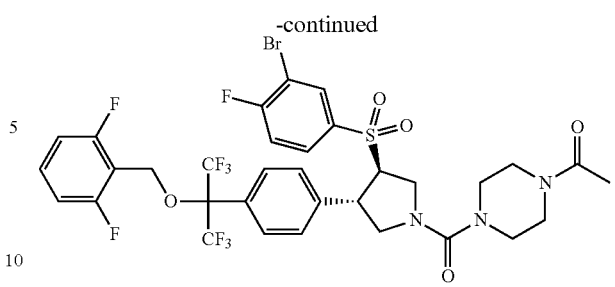

Step A: 2-(4-(bromomethyl)phenyl)-1,1,1,3,3,3-hexafluoropropan-2-ol

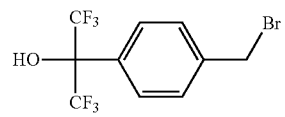

N-Bromosuccinimide (13.79 g, 77 mmol) and 2,2'-azobis(2-methylpropionitrile) (0.025 g, 0.155 mmol) were added to a solution of 1,1,1,3,3,3-hexafluoro-2-(p-tolyl)propan-2-ol (20.00 g, 77 mmol) in carbon tetrachloride (80 mL). The resulting suspension was heated to reflux under nitrogen for 4 h, cooled to room temperature and filtered through a celite pad. The filter cake was rinsed with ether and the filtrate was concentrated under reduced pressure. The residue was treated with ether (100 mL) and hexanes (50 mL), stirred for 15 min and filtered. The filtrate was concentrated under reduced pressure and dried under vacuum to give crude product as tan liquid (27.07 g). $^1$H NMR analysis showed a 69:15:16 molar ratio of the desired 2-(4-(bromomethyl)phenyl)-1,1,1,3,3,3-hexafluoropropan-2-ol, unreacted 1,1,1,3,3,3-hexafluoro-2-(p-tolyl)propan-2-ol and 2-(4-(dibromomethyl)phenyl)-1,1,1,3,3,3-hexafluoropropan-2-ol. The mixture was used without further purification, assuming ~70% purity of the desired 2-(4-(bromomethyl)phenyl)-1,1,1,3,3,3-hexafluoropropan-2-ol.

Step B: 2-(4-(((3-bromo-4-fluorophenyl)thio)methyl)phenyl)-1,1,1,3,3,3-hexafluoropropan-2-ol

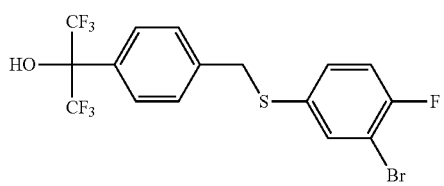

Potassium carbonate (206 mg, 1.49 mmol) was added to a solution of 3-bromo-4-fluorobenzenethiol (103 mg, 0.497 mmol) and 2-(4-(bromomethyl)phenyl)-1,1,1,3,3,3-hexafluoropropan-2-ol (251 mg, 0.746 mmol) in tetrahydrofuran (5 mL). After 15 h at ambient temperature, the mixture was diluted with ethyl acetate (100 mL), washed with water (10 mL), brine (10 mL), dried (magnesium sulfate), filtered and concentrated under reduced pressure to give the desired 2-(4-(((3-bromo-4-fluorophenyl)thio)methyl)phenyl)-1,1,1,3,3,3-hexafluoropropan-2-ol as crude material (260 mg). It was used without further purification. LC/MS (M−1): 463.1; LC retention time: 1.69 min (analytical HPLC Method F).

Step C: 2-(4-(((3-bromo-4-fluorophenyl)sulfonyl)methyl)phenyl)-1,1,1,3,3,3-hexafluoropropan-2-ol

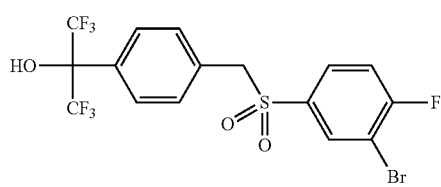 [SMILES: O=S(=O)(Cc1ccc(C(O)(C(F)(F)F)C(F)(F)F)cc1)c1ccc(F)c(Br)c1]

mCPBA (172 mg, 0.994 mmol, 77% pure) was added to a solution of 2-(4-(((3-bromo-4-fluorophenyl)thio)methyl)phenyl)-1,1,1,3,3,3-hexafluoropropan-2-ol (230 mg, 0.497 mmol) in dichloromethane (5 mL). After 5 h at ambient temperature, the mixture was quenched with saturated sodium bicarbonate (5 mL), diluted with ethyl acetate (100 mL), washed with water (10 mL), brine (10 mL), dried (magnesium sulfate), filtered and concentrated under reduced pressure. Silica gel chromatography, eluting with 0-50% ethyl acetate in hexanes, gave the desired 2-(4-(((3-bromo-4-fluorophenyl)sulfonyl)methyl)phenyl)-1,1,1,3,3,3-hexafluoropropan-2-ol (130 mg, 53% yield over 2 steps). LC/MS (M−1): 495.0; LC retention time: 1.40 min (analytical HPLC Method F); $^1$H NMR (400 MHz, CDCl$_3$) δ 7.77 (m, 1H), 7.68 (d, J=8.1 Hz, 2H), 7.52 (m, 1H), 7.32-7.19 (m, 2H), 7.15 (t, J=8.3 Hz, 1H), 4.35 (s, 2H).

Step D: 2-(((2-(4-(((3-bromo-4-fluorophenyl)sulfonyl)methyl)phenyl)-1,1,1,3,3,3-hexafluoropropan-2-yl)oxy)methyl)-1,3-difluorobenzene

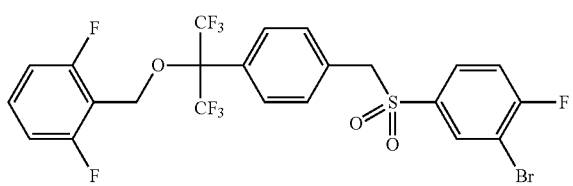 [SMILES: O=S(=O)(Cc1ccc(C(OCc2c(F)cccc2F)(C(F)(F)F)C(F)(F)F)cc1)c1ccc(F)c(Br)c1]

Potassium carbonate (109 mg, 0.788 mmol) was added to a solution of 2-(4-(((3-bromo-4-fluorophenyl)sulfonyl)methyl)phenyl)-1,1,1,3,3,3-hexafluoropropan-2-ol (130 mg, 0.263 mmol) and 2-(bromomethyl)-1,3-difluorobenzene (65.2 mg, 0.315 mmol) in N,N-dimethylformamide (2 mL). After 5 h at ambient temperature, the mixture was diluted with ethyl acetate (100 mL), washed with water (10 mL), brine (10 mL), dried (magnesium sulfate), filtered and concentrated under reduced pressure. Silica gel chromatography, eluting with 0-30% ethyl acetate in hexanes, gave the desired 2-(((2-(4-(((3-bromo-4-fluorophenyl)sulfonyl)methyl)phenyl)-1,1,1,3,3,3-hexafluoropropan-2-yl)oxy)methyl)-1,3-difluorobenzene (130 mg, 80% yield). LC/MS (M−1): 621.1; LC retention time: 1.75 min (analytical HPLC Method F); $^1$H NMR (400 MHz, CDCl$_3$) δ 7.78 (dd, J=6.4, 2.2 Hz, 1H), 7.64 (d, J=8.1 Hz, 2H), 7.57 (m, 1H), 7.43-7.33 (m, 1H), 7.29-7.24 (m, 2H), 7.17 (t, J=8.1 Hz, 1H), 7.10-6.90 (m, 2H), 4.68 (s, 2H), 4.40 (s, 2H).

Step E: (E)-2-(((2-(4-(2-((3-bromo-4-fluorophenyl)sulfonyl)vinyl)phenyl)-1,1,1,3,3,3-hexafluoropropan-2-yl)oxy)methyl)-1,3-difluorobenzene & 2-(((2-(4-(1-((3-bromo-4-fluorophenyl)sulfonyl)vinyl)phenyl)-1,1,1,3,3,3-hexafluoropropan-2-yl)oxy)methyl)-1,3-difluorobenzene

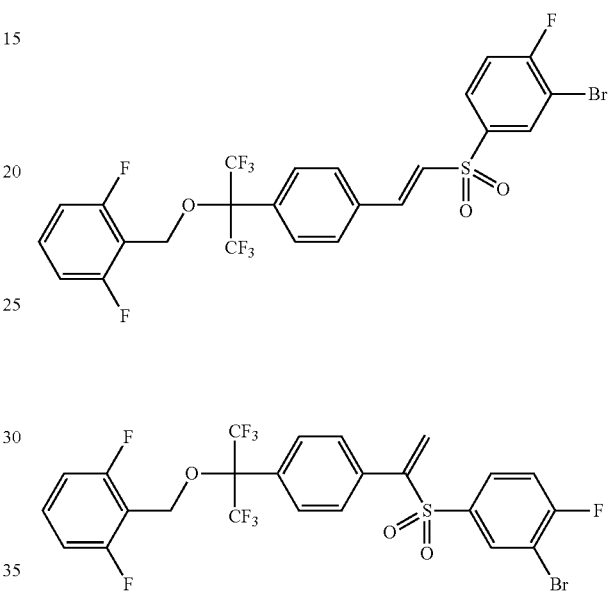

N,N,N',N'-tetramethylmethanediamine (128 mg, 1.26 mmol) and acetic anhydride (0.118 mL, 1.26 mmol) were added to a solution of 2-(((2-(4-(((3-bromo-4-fluorophenyl)sulfonyl)methyl)phenyl)-1,1,1,3,3,3-hexafluoropropan-2-yl)oxy)methyl)-1,3-difluorobenzene (130 mg, 0.209 mmol) in N,N-dimethylformamide (1 mL) at room temperature. The mixture was stirred at room temperature in a sealed viral for 1 h and heated to 65° C. for 15 h. The mixture was cooled to room temperature, diluted with ethyl acetate (100 mL), washed with saturated sodium bicarbonate (1 mL), water (10 mL), brine (10 mL), dried (magnesium sulfate), filtered and concentrated under reduced pressure. Silica gel chromatography, eluting with 0-20% ethyl acetate in hexanes, gave the desired (E)-2-(((2-(4-(2-((3-bromo-4-fluorophenyl)sulfonyl)vinyl)phenyl)-1,1,1,3,3,3-hexafluoropropan-2-yl)oxy)methyl)-1,3-difluorobenzene (60 mg, 45% yield). $^1$H NMR (400 MHz, CDCl$_3$) δ 8.18 (dd, J=6.2, 2.2 Hz, 1H), 7.91 (ddd, J=8.7, 4.4, 2.3 Hz, 1H), 7.82-7.65 (m, 3H), 7.69-7.60 (m, 2H), 7.44-7.34 (m, 1H), 7.34-7.21 (m, 2H), 7.06-6.89 (m, 2H), 4.71 (s, 2H). A byproduct corresponding to 2-(((2-(4-(1-((3-bromo-4-fluorophenyl)sulfonyl)vinyl)phenyl)-1,1,1,3,3,3-hexafluoropropan-2-yl)oxy)methyl)-1,3-difluorobenzene was also observed. $^1$H NMR (400 MHz, CDCl$_3$) δ 7.86 (dd, J=6.2, 2.3 Hz, 1H), 7.67-7.59 (m, 1H), 7.52-7.42 (m, 2H), 7.42-7.29 (m, 1H), 7.15-7.07 (m, 1H), 6.99-6.89 (m, 4H), 6.71 (s, 2H), 6.09 (s, 2H).

Step F: (3R,4S)-1-benzyl-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine & (3S,4R)-1-benzyl-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine

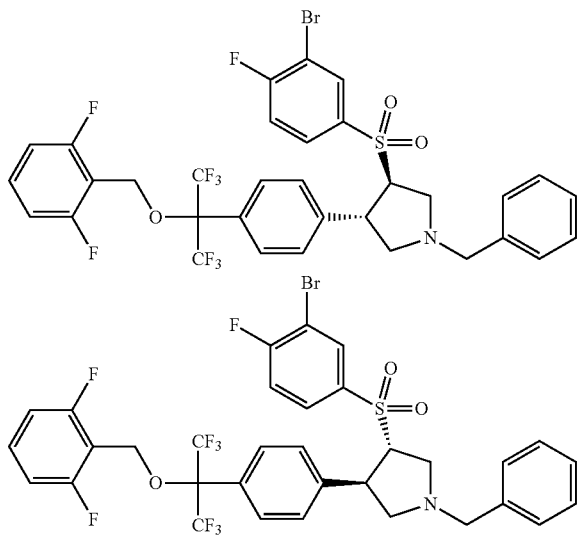

A 0.2 M dichloromethane solution of trifluoroacetic acid (0.98 mL, 0.196 mmol) was added dropwise to a solution of (E)-2-(((2-(4-(2-((3-bromo-4-fluorophenyl)sulfonyl)vinyl)phenyl)-1,1,1,3,3,3-hexafluoropropan-2-yl)oxy)methyl)-1,3-difluorobenzene (3.1 g, 4.89 mmol) and N-benzyl-1-methoxy-N-((trimethylsilyl)methyl)methanamine (3.49 g, 14.68 mmol) in dichloromethane (30 mL) at 0° C. After stirring under nitrogen at 0° C. for 10 min and at room temperature for 1 h, the resulting mixture was diluted with ethyl acetate (300 mL), washed with saturated sodium bicarbonate (2×50 mL) and brine (50 mL), dried (magnesium sulfate), filtered and concentrated under reduced pressure. Silica gel chromatography, eluting with 0-30% ethyl acetate in hexanes, gave the desired product as racemic material (2.50 g). It was separated into its homochiral components using a chiral Lux Cellulose-4 (3×25 cm, 5 μm), CO$_2$/methanol (65/35), 40° C., 100 bars to afford the desired (3R,4S)-1-benzyl-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine as the first eluent off the column (1.05 g, 46.3% yield). LC/MS (M+1): 766.5; LC retention time: 4.24 min (analytical HPLC Method D); $^1$H NMR (400 MHz, CD3OD) δ 8.10 (dd, J=6.4, 2.2 Hz, 1H), 7.91-7.81 (m, 1H), 7.59-7.41 (m, 3H), 7.41-7.30 (m, 6H), 7.30-7.22 (m, 2H), 7.15-6.95 (m, 2H), 4.64 (s, 2H), 4.31-4.15 (m, 1H), 3.90-3.72 (m, 2H), 3.66 (d, J=12.8 Hz, 1H), 3.42-3.35 (m, 1H), 3.23-2.99 (m, 2H), 2.65 (dd, J=9.2, 7.9 Hz, 1H). It also afforded the desired (3S,4R)-1-benzyl-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine as the second eluent off the column (1.02 g, 45.5% yield). LC/MS (M+1): 766.5; LC retention time: 4.24 min (analytical HPLC Method D); $^1$H NMR (400 MHz, CD3OD) δ 8.10 (dd, J=6.4, 2.2 Hz, 1H), 7.91-7.81 (m, 1H), 7.59-7.41 (m, 3H), 7.41-7.30 (m, 6H), 7.30-7.22 (m, 2H), 7.15-6.95 (m, 2H), 4.64 (s, 2H), 4.31-4.15 (m, 1H), 3.90-3.72 (m, 2H), 3.66 (d, J=12.8 Hz, 1H), 3.42-3.35 (m, 1H), 3.23-2.99 (m, 2H), 2.65 (dd, J=9.2, 7.9 Hz, 1H).

Step G: (3S,4R)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine

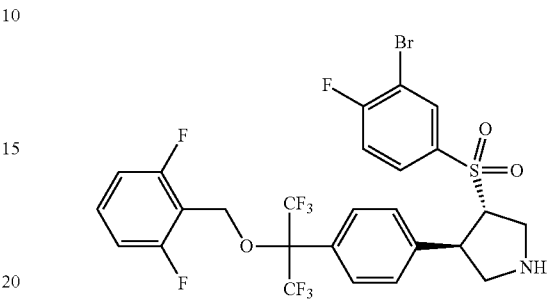

Sodium iodide (14.96 mg, 0.100 mmol) was added to a solution of (3S,4R)-1-benzyl-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine (51 mg, 0.067 mmol), 1-chloroethyl carbonochloridate (14.27 mg, 0.100 mmol) in 1,2-dichloroethane (1 mL) in a sealed vial. After 15 h at reflux, the mixture was concentrated under reduced pressure. The residue was treated with methanol (1 mL) and heated to reflux for 1 h. The mixture was cooled to room temperature, diluted with ethyl acetate (100 mL), washed with water (10 mL), brine (10 mL), dried (magnesium sulfate), filtered and concentrated under reduced pressure to provide the desired (3S,4R)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine as crude material (42 mg). LC/MS (M+1): 676.3; LC retention time: 0.95 min (analytical HPLC Method G). It was used without further purification.

Step H: 1-(4-((3S,4R)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone

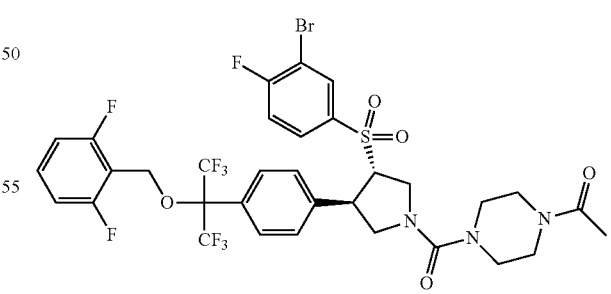

Hunig's base (0.046 mL, 0.266 mmol) was added to a mixture of crude (3S,4R)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine (45 mg) from Step G and 4-acetylpiperazine-1-carbonyl chloride (25.4 mg, 0.133 mmol) in dichloromethane (1 mL). After 3 h at room temperature, the mixture was diluted with ethyl acetate (100 mL), washed with water (10 mL), brine (10 mL), dried (magnesium sulfate), filtered and concentrated under reduced pressure. Silica gel chromatography, eluting with 0-10% methanol in dichloromethane, gave Example 168 (26 mg, 47% yield over 2 steps). LC/MS (M+1): 832.5; LC retention time: 4.51 min (analytical HPLC Method D); $^1$H NMR (400 MHz, CD3OD) δ 8.06 (m, 1H), 7.78 (m, 1H), 7.62-7.46 (m, 3H), 7.34 (d, J=8.6 Hz, 2H), 7.17 (t, J=8.5 Hz, 1H), 7.14-6.91 (m, 2H), 4.72-4.50 (m, 3H), 4.26 (m, 1H), 4.08-3.94 (m, 2H), 3.87-3.70 (m, 1H), 3.68-3.51 (m, 4H), 3.51-3.35 (m, 6H), 2.02 (s, 3H).

Step I: 1-(4-((3R,4S)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone

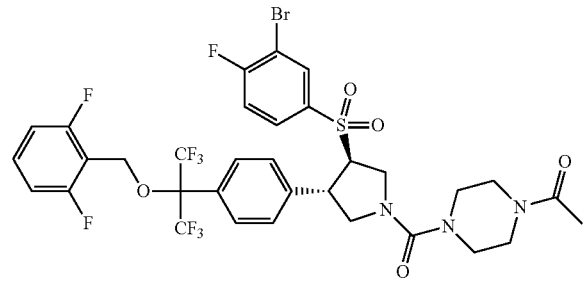 [SMILES: CC(=O)N1CCN(C(=O)N2C[C@H](c3ccc(C(OCc4c(F)cccc4F)(C(F)(F)F)C(F)(F)F)cc3)[C@@H](S(=O)(=O)c3ccc(F)c(Br)c3)C2)CC1]

Following similar procedures from Steps G and H, (3R,4S)-1-benzyl-3-((3-bromo-4-fluorophenyl)sulfonyl)-4-(4-((R)-1-((2,6-difluorobenzyl)oxy)-2,2,2-trifluoro-1-silylethyl)phenyl)pyrrolidine (51 mg, 0.070 mmol) was converted to Example 169 (28 mg, 51% yield over 2 steps). LC/MS (M+1): 832.5; LC retention time: 4.51 min (analytical HPLC Method D); $^1$H NMR (400 MHz, CD3OD) δ 8.06 (m, 1H), 7.78 (m, 1H), 7.62-7.46 (m, 3H), 7.34 (d, J=8.6 Hz, 2H), 7.17 (t, J=8.5 Hz, 1H), 7.14-6.91 (m, 2H), 4.72-4.50 (m, 3H), 4.26 (m, 1H), 4.08-3.94 (m, 2H), 3.87-3.70 (m, 1H), 3.68-3.51 (m, 4H), 3.51-3.35 (m, 6H), 2.02 (s, 3H).

Example 170

1-(4-((3S,4R)-3-(4-(2-((2,6-difluorobenzyl)oxy)-1,1,1,3,3,3-hexafluoropropan-2-yl)phenyl)-4-((4-fluorophenyl)sulfonyl)pyrrolidine-1-carbonyl)piperazin-1-yl)ethanone

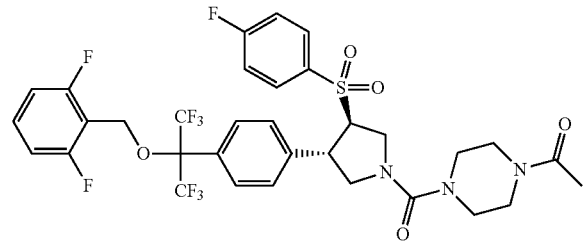 [SMILES: CC(=O)N1CCN(C(=O)N2C[C@H](c3ccc(C(OCc4c(F)cccc4F)(C(F)(F)F)C(F)(F)F)cc3)[C@@H](S(=O)(=O)c3ccc(F)cc3)C2)CC1]

A mixture of i-(4-((3R,4)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone (12 mg, 0.014 mmol) and 10% palladium on carbon (4.61 mg, 0.0043 mmol) in methanol (5 mL) was hydrogenated under a hydrogen balloon for 2 h. The mixture was filtered to remove the catalyst. The filtrate was concentrated to give Example 170 (8.7 mg, 80% yield). LC/MS (M+1): 752.6; LC retention time: 2.09 min (analytical HPLC Method C); $^1$H NMR (400 MHz, CD3OD) δ 7.94-7.73 (m, 2H), 7.56-7.38 (m, 3H), 7.24 (d, J=8.5 Hz, 2H), 7.12-6.93 (m, 4H), 4.31 (q, J=8.3 Hz, 1H), 4.26-4.15 (m, 1H), 4.02 (td, J=11.7, 8.2 Hz, 2H), 3.93-3.77 (m, 1H), 3.73-3.54 (m, 4H), 3.54-3.35 (m, 7H), 2.14 (s, 3H).

Example 171

1-(4-((3R,4S)-3-(4-(2-((2,6-difluorobenzyl)oxy)-1,1,1,3,3,3-hexafluoropropan-2-yl)phenyl)-4-((4-fluorophenyl)sulfonyl)pyrrolidine-1-carbonyl)piperazin-1-yl)ethanone

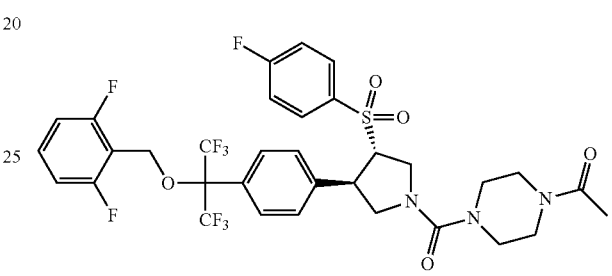

A mixture of 1-(4-((3S,4R)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone (8.0 mg, 0.0096 mmol) and 10% palladium on carbon (4.61 mg, 0.0043 mmol) in methanol (5 mL) was hydrogenated under a hydrogen balloon for 2 h. The mixture was filtered to remove the catalyst. The filtrate was concentrated to give Example 171 (3.1 mg, 40% yield). LC/MS (M+1): 752.6; LC retention time: 4.34 min (analytical HPLC Method D); $^1$H NMR (400 MHz, CD3OD) δ 7.91-7.74 (m, 2H), 7.55-7.37 (m, 3H), 7.24 (d, J=8.4 Hz, 2H), 7.15-6.90 (m, 4H), 4.64-4.52 (m, 2H), 4.36-4.12 (m, 2H), 4.12-3.95 (m, 2H), 3.95-3.74 (m, 1H), 3.70-3.39 (m, 10H), 2.14 (s, 3H).

Example 172

1-(4-((3R,4S)-3-(4-(2-((2,6-difluorobenzyl)oxy)-1,1,1,1,3,3,3-hexafluoropropan-2-yl)phenyl)-4-((4-fluoro-3-vinylphenyl)sulfonyl)pyrrolidine-1-carbonyl)piperazin-1-yl)ethanone

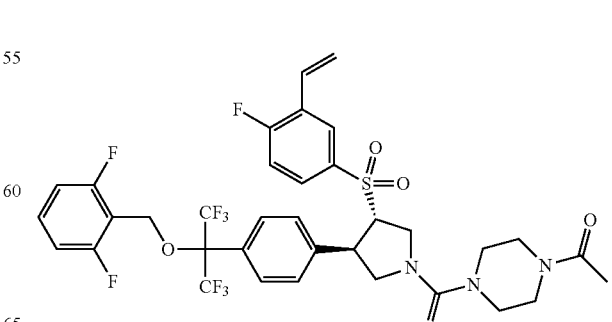

A mixture of 1-(4-((3S,4R)-3-((3-bromo-4-fluorophenyl) sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone (12 mg, 0.014 mmol), potassium trifluoro(vinyl)borate (3.87 mg, 0.029 mmol), [1,1'-bis(diphenylphosphino)ferrocene]dichloropalladium(II) (2.12 mg, 2.89 μmol) and 2.0 M aqueous potassium phosphate tribasic (0.022 mL, 0.043 mmol) in N,N-dimethylformamide (0.5 mL) was degassed with nitrogen in a sealed vial and heated to 90° C. for 2 h. The mixture was cooled to room temperature and purified via preparative LC/MS with the following conditions: Column: Waters XBridge C18, 19×200 mm, 5-m particles; Mobile Phase A: 5:95 acetonitrile: water with 10-mM ammonium acetate; Mobile Phase B: 95:5 acetonitrile: water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 172 (5.0 mg, 45% yield). LC/MS (M+1): 778.5; HPLC RT=2.27 min (analytical HPLC Method C). $^1$H NMR (400 MHz, DMSO-d6) δ 7.93 (d, J=5.4 Hz, 1H), 7.69-7.53 (m, 2H), 7.40 (d, J=8.1 Hz, 2H), 7.31 (d, J=7.7 Hz, 2H), 7.23 (t, J=7.9 Hz, 2H), 7.15 (t, J=9.6 Hz, 1H), 6.63 (dd, J=17.7, 11.3 Hz, 1H), 5.95 (d, J=17.5 Hz, 1H), 5.46 (d, J=11.4 Hz, 1H), 4.80 (q, J=8.9 Hz, 1H), 4.52 (q, J=10.0 Hz, 2H), 4.25-4.05 (m, 1H), 3.98-3.83 (m, 2H), 3.71-3.51 (m, 2H), 3.48-3.03 (m, 8H), 2.03 (s, 3H).

Example 173

1-(4-((3S,4R)-3-((3-allyl-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone

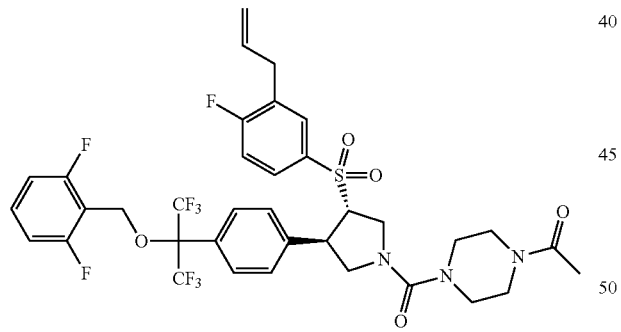

Following similar procedure as Example 172, i-(4-((3S,4)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone (12 mg, 0.014 mmol) was treated with potassium allyltrifluoroborate (4.28 mg, 0.029 mmol) to provide Example 173 (5.6 mg, 49% yield). LC/MS (M+1): 792.6; HPLC RT=2.31 min (analytical HPLC Method C); $^1$H NMR (400 MHz, DMSO-d6) δ 7.69 (d, J=5.0 Hz, 1H), 7.63-7.49 (m, 2H), 7.46-7.28 (m, 4H), 7.23 (t, J=7.9 Hz, 2H), 7.08 (t, J=8.9 Hz, 1H), 5.87 (ddt, J=16.9, 10.1, 6.7 Hz, 1H), 5.27-4.94 (m, 2H), 4.70 (q, J=8.5 Hz, 1H), 4.64-4.49 (m, 2H), 4.10 (dd, J=11.3, 7.9 Hz, 1H), 3.96-3.87 (m, 1H), 3.87-3.75 (m, 1H), 3.50-3.04 (m, 10H), 2.01 (s, 3H).

Example 174

1-(4-((3S,4R)-3-((3-cyclopropyl-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone

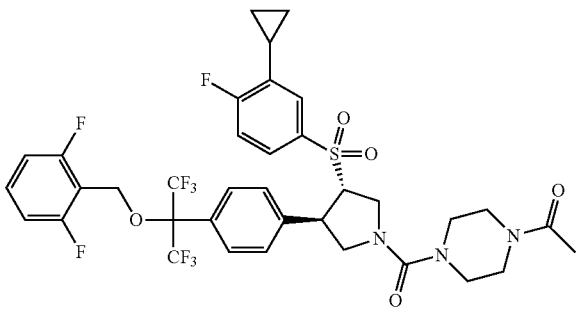 [SMILES: CC(=O)N1CCN(C(=O)N2C[C@@H](S(=O)(=O)c3ccc(F)c(C4CC4)c3)[C@H](c3ccc(C(OCc4c(F)cccc4F)(C(F)(F)F)C(F)(F)F)cc3)C2)CC1]

Following similar procedure as Example 172, 1-(4-((3S,4R)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone (12 mg, 0.014 mmol) was treated with cyclopropylboronic acid (2.48 mg, 0.029 mmol) to provide Example 174 (3.4 mg, 30% yield). LC/MS (M+1): 792.6; HPLC RT=2.31 min (analytical HPLC Method C); $^1$H NMR (400 MHz, DMSO-d6) δ 7.60 (t, J=7.6 Hz, 1H), 7.48 (br. s., 1H), 7.42-7.28 (m, 4H), 7.28-7.15 (m, 3H), 7.05 (t, J=9.3 Hz, 1H), 4.80 (q, J=8.5 Hz, 1H), 4.65-4.42 (m, 2H), 4.27-4.03 (m, 1H), 3.95-3.75 (m, 2H), 3.71-3.58 (m, 1H), 3.42 (m, 3H), 3.34-3.07 (m, 6H), 2.90 (s, 3H), 2.01 (s, 3H), 1.88 (m, 1H), 0.97 (m, 2H), 0.79-0.41 (m, 2H).

Example 175

1-(4-((3R,4S)-3-(4-(2-((2,6-difluorobenzyl)oxy)-1,1,1,3,3,3-hexafluoropropan-2-yl)phenyl)-4-((6-fluoro-[1,1'-biphenyl]-3-yl)sulfonyl)pyrrolidine-1-carbonyl)piperazin-1-yl)ethanone

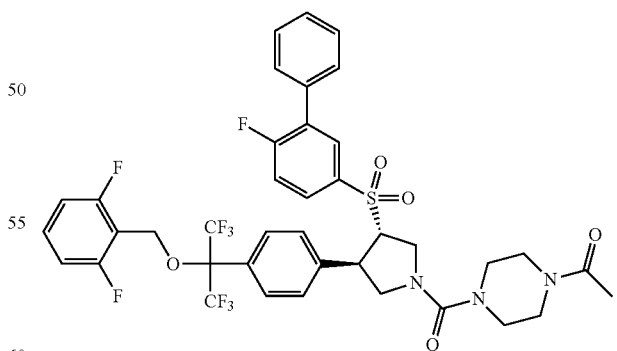

A mixture of 1-(4-((3S,4R)-3-((3-bromo-4-fluorophenyl) sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone (12 mg, 0.014 mmol), phenylboronic acid (3.52 mg, 0.029 mmol), palladium tetrakis(triphenylphosphine) (1.67 mg, 1.45 μmol) and 2.0 M aqueous potassium phosphate tribasic (0.014 mL, 0.029 mmol) in N,N-dimethylformamide (0.5 mL) was degassed with nitrogen in a sealed vial and heated to 90° C. for 2 h. The mixture was cooled to room temperature and purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 175 (3.0 mg, 25% yield). LC/MS (M+1): 828.5; HPLC RT=2.36 min (analytical HPLC Method C); $^1$H NMR (400 MHz, DMSO-d6) δ 8.05-7.82 (m, 1H), 7.72 (dd, J=7.0, 4.0 Hz, 1H), 7.64-7.55 (m, 1H), 7.55-7.42 (m, 6H), 7.42-7.30 (m, 3H), 7.30-7.12 (m, 3H), 4.93 (q, J=8.5 Hz, 1H), 4.53-4.34 (m, 2H), 4.16 (dd, J=11.6, 7.9 Hz, 1H), 4.05-3.90 (m, 1H), 3.85 (dd, J=11.6, 9.2 Hz, 1H), 3.77-3.69 (m, 1H), 3.41-3.29 (m, 5H), 3.32-3.04 (m, 4H), 2.00 (s, 3H).

Example 176

1-(4-((3S,4R)-3-(4-(2-((2,6-difluorobenzyl)oxy)-1,1,1,3,3,3-hexafluoropropan-2-yl)phenyl)-4-((6-fluoro-[1,1'-biphenyl]-3-yl)sulfonyl)pyrrolidine-1-carbonyl)piperazin-1-yl)ethanone

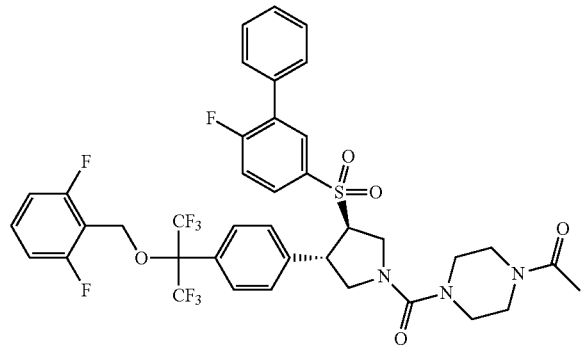 [SMILES: CC(=O)N1CCN(C(=O)N2C[C@H](c3ccc(C(OCc4c(F)cccc4F)(C(F)(F)F)C(F)(F)F)cc3)[C@@H](S(=O)(=O)c3ccc(F)c(-c4ccccc4)c3)C2)CC1]

Following similar procedure as Example 175, 1-(4-((3R,4S)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone (12 mg, 0.014 mmol) was converted to Example 176 (3.0 mg, 25% yield). LC/MS (M+1): 828.5; HPLC RT=2.36 min (analytical HPLC Method C); $^1$H NMR (400 MHz, DMSO-d6) δ 8.05-7.82 (m, 1H), 7.72 (dd, J=7.0, 4.0 Hz, 1H), 7.64-7.55 (m, 1H), 7.55-7.42 (m, 6H), 7.42-7.30 (m, 3H), 7.30-7.12 (m, 3H), 4.93 (q, J=8.5 Hz, 1H), 4.53-4.34 (m, 2H), 4.16 (dd, J=11.6, 7.9 Hz, 1H), 4.05-3.90 (m, 1H), 3.85 (dd, J=11.6, 9.2 Hz, 1H), 3.77-3.69 (m, 1H), 3.41-3.29 (m, 5H), 3.32-3.04 (m, 4H), 2.00 (s, 3H).

Example 177

1-(4-((3R,4S)-3-(4-(2-((2,6-difluorobenzyl)oxy)-1,1,1,3,3,3-hexafluoropropan-2-yl)phenyl)-4-((4-fluoro-3-(1-methyl-1H-pyrazol-4-yl)phenyl)sulfonyl)pyrrolidine-1-carbonyl)piperazin-1-yl)ethanone

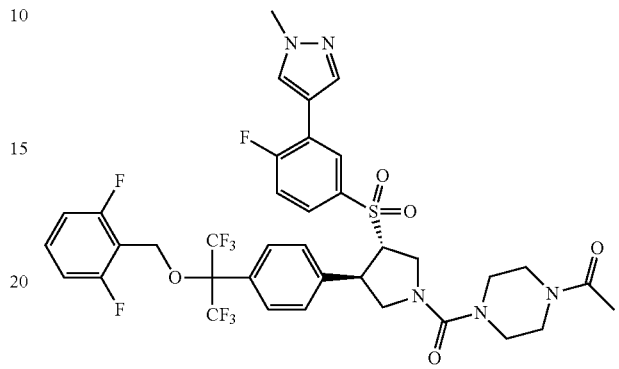

Following similar procedure as Example 175, 1-(4-((3S,4R)-3-((3-bromo-4-fluorophenyl)sulfonyl)-4-(4-(2-((2,6-difluorobenzyl)oxy)-1,1,1,3,3,3-hexafluoropropan-2-yl)phenyl)pyrrolidine-1-carbonyl)piperazin-1-yl)ethanone (12 mg, 0.014 mmol) was treated with 1-methyl-4-(4,4,5,5-tetramethyl-1,3,2-dioxaborolan-2-yl)-1H-pyrazole (6.01 mg, 0.029 mmol) to provide Example 177 (2.2 mg, 18% yield). LC/MS (M+1): 832.6; HPLC RT=2.06 min (analytical HPLC Method C); $^1$H NMR (400 MHz, DMSO-d6) δ 8.09 (s, 1H), 8.02-7.91 (m, 1H), 7.86 (s, 1H), 7.65-7.53 (m, 2H), 7.42 (d, J=8.1 Hz, 2H), 7.31-7.10 (m, 5H), 4.84 (q, J=8.8 Hz, 1H), 4.31 (q, J=9.8 Hz, 2H), 4.18 (dd, J=11.3, 7.9 Hz, 1H), 3.99-3.81 (m, 2H), 3.69-3.52 (m, 8H), 3.32-3.03 (m, 2H), 2.01 (s, 3H).

General RORγ SPA Binding Assay

The binding of potential ligands to RORγ is measured by competition with [$^3$H]25-hydroxycholesterol (Perkin Elmer NET674250UC) using a scintillation proximity assay (SPA) binding assay. The ligand binding domain of human RORγ (A262-S507) with an N-terminal His tag is expressed in E. coli and purified using nickel affinity chromatography. 15 μg/well RORγ (A262-S507) is incubated with test compound at varying concentrations in 3-fold serial dilution, with final concentrations ranging from 16.6 μM to 0.28 nM for 10 min at room temperature in PBS buffer (Invitrogen #14190-144) containing 0.5% fatty acid free BSA (Gemini Bio-Products, Cat. #700-107P) and 0.1% Glycerol (Sigma Cat # G5516). 10 nM of [$^3$H] 25-hydroxycholesterol is then added, and the reaction is incubated for 10 min. 10 mg/mL of Copper-His Tag-PVT beads (Perkin Elmer cat # RPNQ0095) are added, and the mixture is incubated for 60 min. The reaction is read on a TopCount Microplate scintillation plate reader (Perkin Elmer). The competition data of the test compound over a range of concentrations was plotted as percentage inhibition of radioligand specifically bound in the absence of test compound (percent of total signal). After correcting for non-specific binding, $IC_{50}$ values were determined. The $IC_{50}$ value is defined as the concentration of test compound needed to reduce [$^3$H] 25-hydroxycholesterol specific binding by 50% and is calculated using the four parameter logistic equation to fit the normalized data.

IC$_{50}$ values of some of the compounds of the invention in the RORγ binding assay are provided below.

| Example # | RORγ Binding IC50, uM |
|---|---|
| 1 | 0.272 |
| 2 | 0.627 |
| 3 | 1.053 |
| 4 | 0.644 |
| 5 | 0.111 |
| 6 | 0.194 |
| 7 | 0.209 |
| 8 | 0.464 |
| 9 | 0.443 |
| 10 | 0.284 |
| 11 | 1.086 |
| 12 | 0.181 |
| 13 | 0.200 |
| 14 | 0.200 |
| 15 | 3.325 |
| 16 | 0.086 |
| 17 | 0.292 |
| 18 | 0.480 |
| 19 | 4.251 |
| 20 | 4.960 |
| 21 | 2.793 |
| 22 | 0.179 |
| 23 | 0.260 |
| 24 | 0.172 |
| 25 | 0.311 |
| 26 | 0.284 |
| 27 | 0.691 |
| 28 | 0.665 |
| 29 | 0.190 |
| 30 | 0.397 |
| 31 | 0.072 |
| 32 | 0.125 |
| 33 | 1.425 |
| 34 | 0.527 |
| 35 | 3.198 |
| 36 | 0.199 |
| 37 | 2.991 |
| 38 | 0.142 |
| 39 | 0.059 |
| 40 | 0.139 |
| 41 | 0.326 |
| 42 | 3.829 |
| 43 | 0.698 |
| 44 | 3.511 |
| 45 | 0.214 |
| 46 | 0.151 |
| 47 | 0.112 |
| 48 | 3.099 |
| 49 | 0.331 |
| 50 | 0.175 |
| 51 | 0.185 |
| 52 | 0.068 |
| 53 | 0.134 |
| 54 | 0.168 |
| 55 | 0.141 |
| 56 | 0.126 |
| 57 | 0.255 |
| 58 | 0.164 |
| 59 | 0.174 |
| 60 | 0.136 |
| 61 | 0.482 |
| 62 | 0.260 |
| 63 | 0.058 |
| 64 | 0.241 |
| 65 | 0.140 |
| 66 | 0.076 |
| 67 | 0.120 |
| 68 | 0.270 |
| 69 | 0.624 |
| 70 | 0.159 |
| 71 | 0.217 |
| 72 | 0.037 |
| 73 | 1.640 |
| 74 | 0.020 |
| 75 | 0.151 |
| 76 | 0.071 |
| 77 | 0.422 |
| 78 | 0.179 |
| 79 | 0.657 |
| 80 | 0.620 |
| 81 | 1.007 |
| 82 | 0.214 |
| 83 | 0.546 |
| 84 | 0.801 |
| 85 | 2.578 |
| 86 | 0.077 |
| 87 | 0.620 |
| 88 | 0.072 |
| 89 | 0.023 |
| 90 | 0.041 |
| 91 | 0.088 |
| 92 | 0.239 |
| 93 | 1.305 |
| 94 | 0.299 |
| 95 | 0.108 |
| 96 | 0.376 |
| 97 | 0.045 |
| 98 | 0.087 |
| 99 | 0.069 |
| 100 | 0.224 |
| 101 | 0.201 |
| 102 | 0.108 |
| 103 | 0.142 |
| 104 | 1.622 |
| 105 | 0.020 |
| 106 | 0.076 |
| 107 | 0.157 |
| 108 | 0.097 |
| 109 | 0.237 |
| 110 | 0.140 |
| 111 | 0.103 |
| 112 | 0.021 |
| 113 | 1.163 |
| 114 | 0.336 |
| 115 | 0.218 |
| 116 | 0.048 |
| 117 | 0.094 |
| 118 | 0.324 |
| 119 | 0.054 |
| 120 | 0.314 |
| 121 | 0.194 |
| 122 | 0.083 |
| 123 | 0.100 |
| 124 | 0.089 |
| 125 | 0.135 |
| 126 | 0.077 |
| 127 | 0.158 |
| 128 | 0.059 |
| 129 | 0.359 |
| 130 | 0.038 |
| 131 | 0.069 |
| 132 | 0.400 |
| 133 | 0.059 |
| 134 | 0.133 |
| 135 | 0.394 |
| 136 | 0.039 |
| 137 | 0.061 |
| 138 | 0.077 |
| 139 | 4.416 |
| 140 | 4.640 |
| 141 | 0.256 |
| 142 | 0.642 |
| 143 | 1.310 |
| 144 | 0.463 |
| 145 | 0.147 |
| 146 | 0.200 |
| 147 | 0.190 |
| 148 | 1.278 |
| 149 | 0.303 |
| 150 | 1.278 |

145
-continued
| Example # | RORγ Binding IC50, uM |
|---|---|
| 151 | 3.481 |
| 152 | 0.881 |
| 153 | 4.940 |
| 154 | 0.965 |
| 155 | 0.477 |
| 156 | 0.528 |
| 157 | 3.026 |
| 158 | 1.997 |
| 159 | 2.620 |
| 160 | 0.538 |
| 161 | 0.485 |
| 162 | 0.686 |
| 163 | 1.481 |
| 164 | 3.348 |
| 165 | 2.339 |
| 166 | 1.880 |
| 167 | 0.051 |
| 168 | 0.326 |
| 169 | 1.012 |
| 170 | 0.593 |
| 171 | 0.190 |
| 172 | 0.517 |
| 173 | 0.089 |
| 174 | 0.079 |
| 175 | 0.606 |
| 176 | 0.084 |
| 177 | 0.542 |
What is claimed is:
1. A compound, or a stereoisomer or a pharmaceutically-acceptable salt thereof, wherein the compound is selected from the group consisting of:
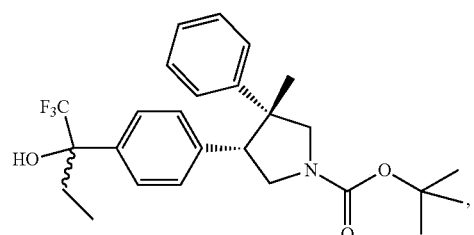
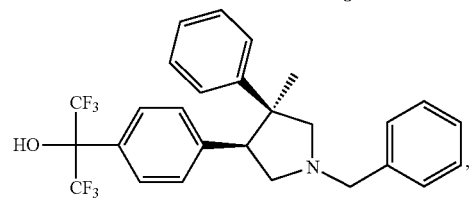
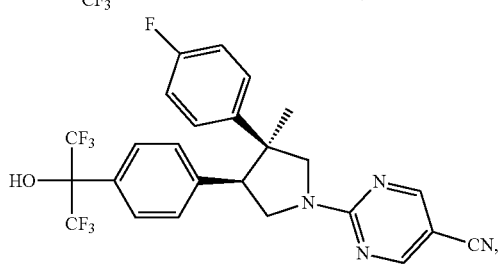
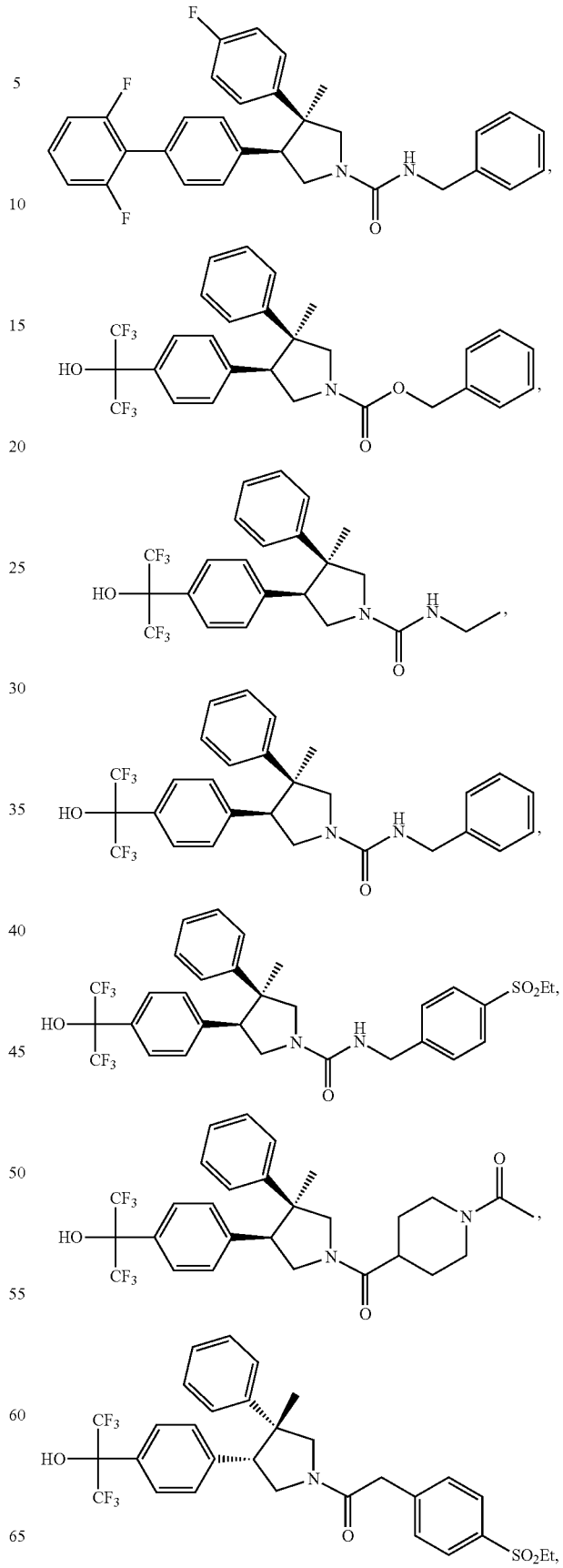

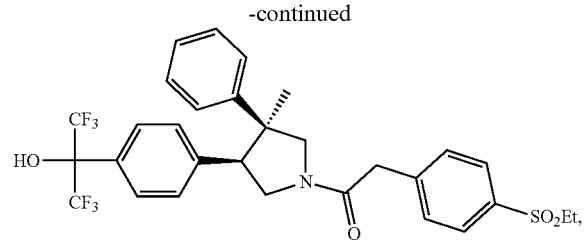
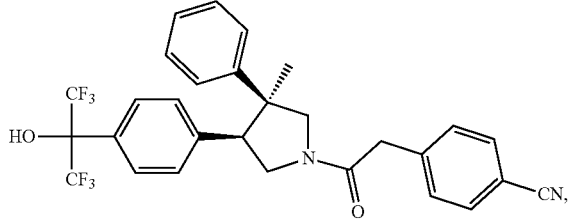
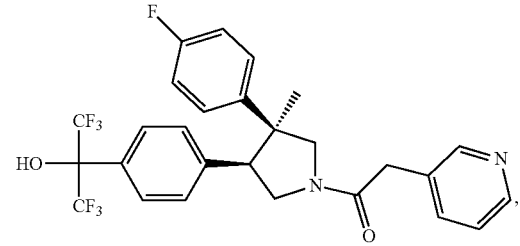
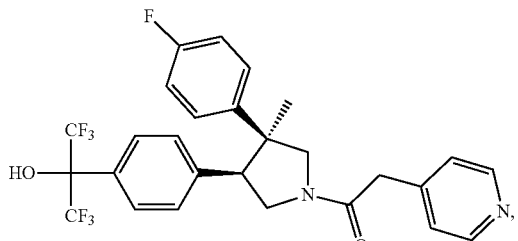
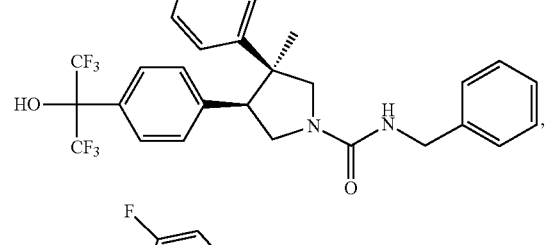
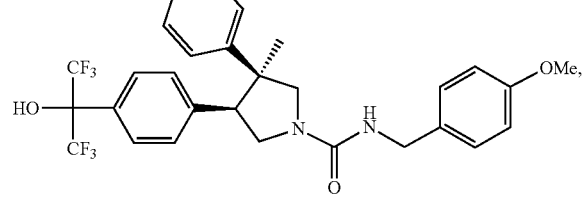
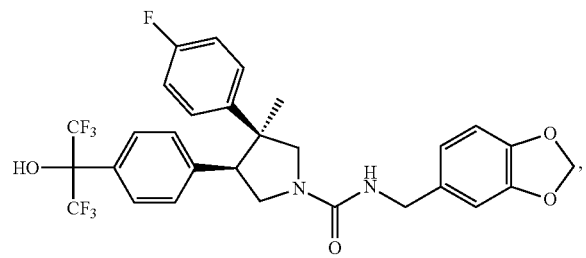
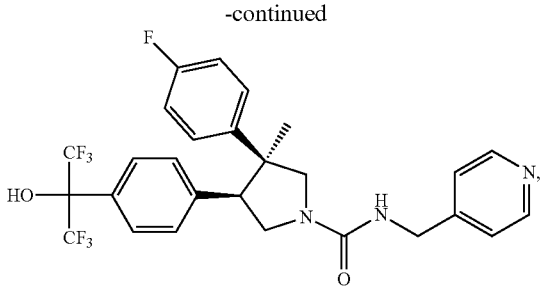
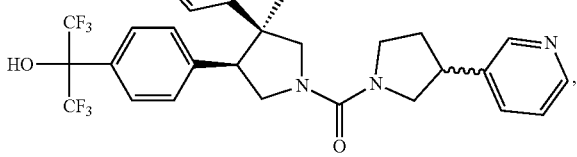
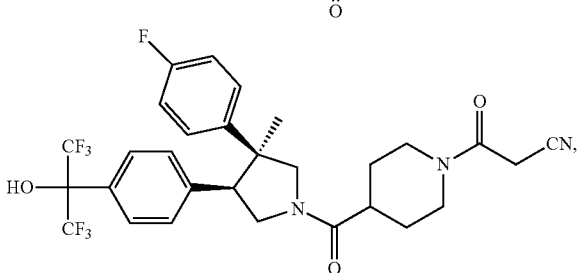
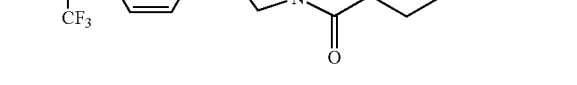
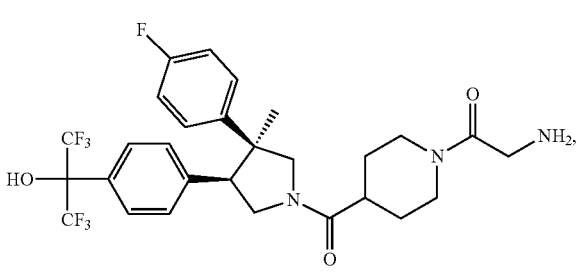
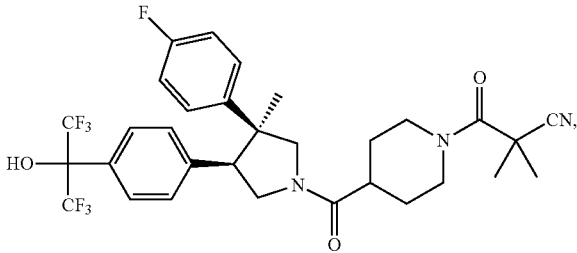

149
-continued
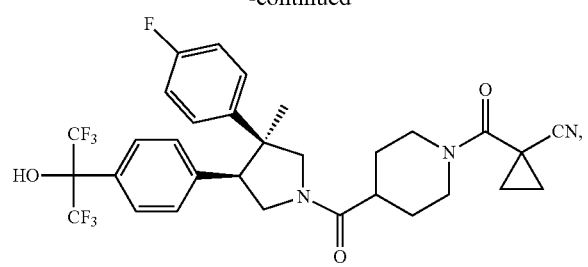
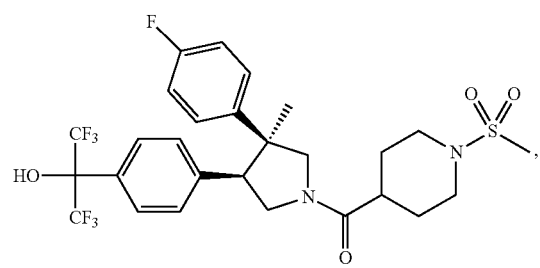
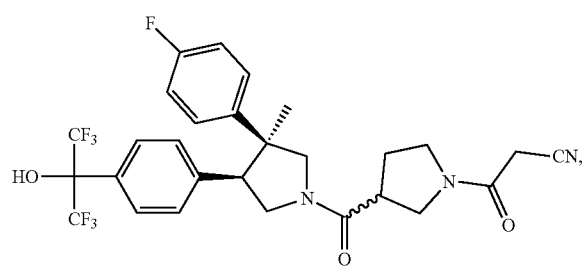
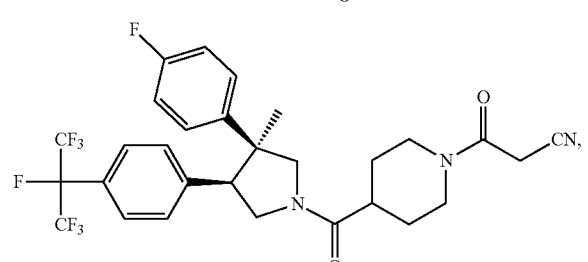
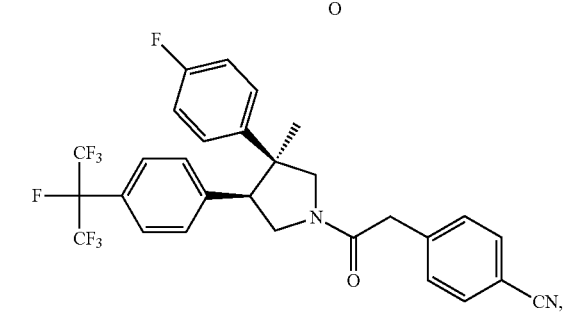
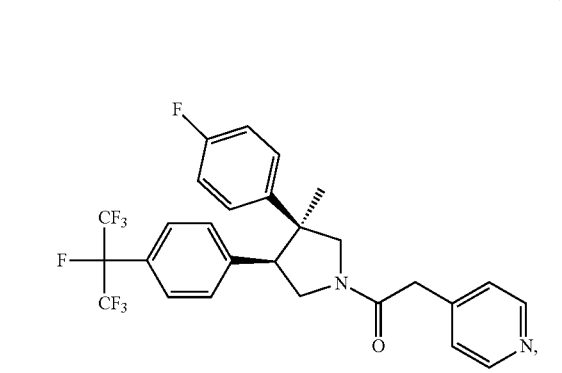
150
-continued
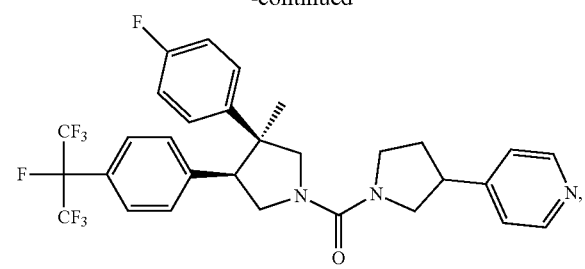
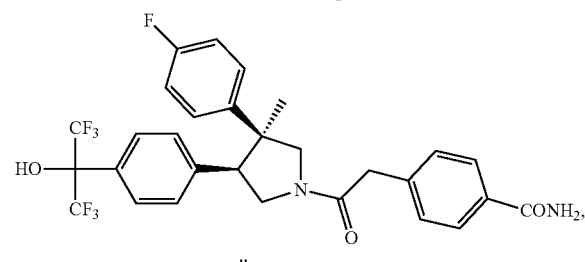
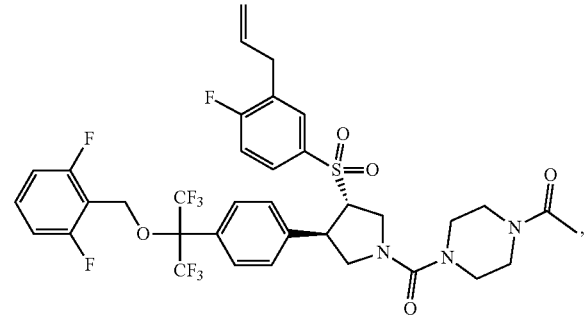
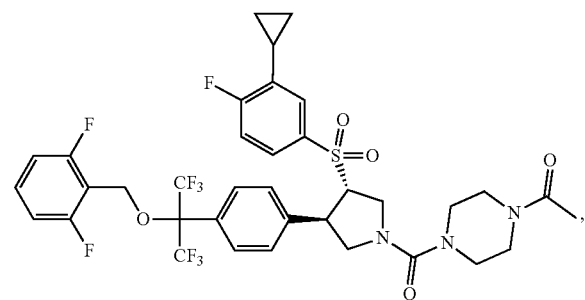
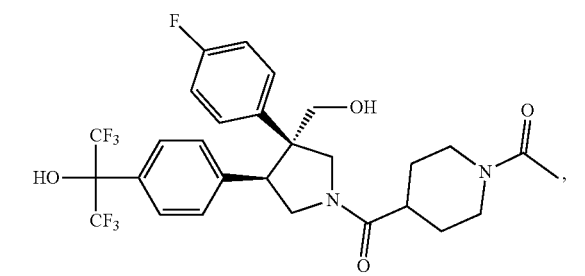
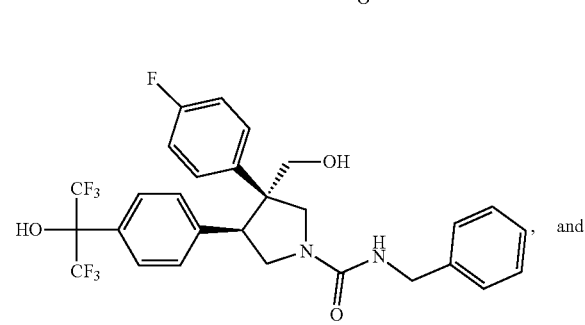, and -continued

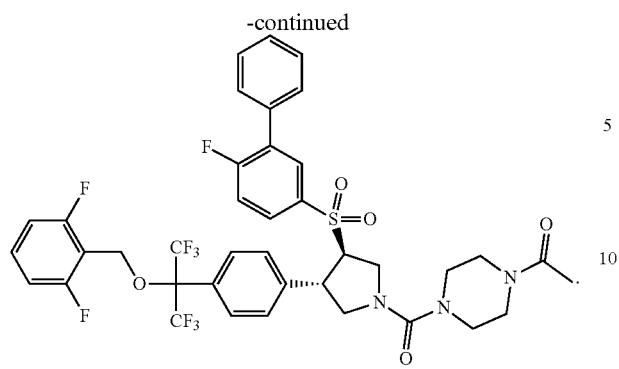

2. A pharmaceutical composition comprising one or more compounds according to claim 1, and a pharmaceutically acceptable carrier or diluent.

3. A method of treating a disease or disorder selected from an autoimmune disease or disorder, asthma, an allergic disease or disorder, a metabolic disease or disorder, and cancer in a subject, the method comprising administering to the subject a therapeutically-effective amount of a compound according to claim 1.

4. The method of claim 3 wherein the autoimmune disease or disorder is selected from psoriasis, rheumatoid arthritis, inflammatory bowel disease, Crohn's disease, ulcerative colitis, acute graft-versus-host disease, psoriatic arthritis, ankylosing spondylitis and multiple sclerosis.

* * * * *